United States Patent
Turzi et al.

(10) Patent No.: US 12,251,397 B2
(45) Date of Patent: Mar. 18, 2025

(54) CROSS-LINKED HYALURONIC ACIDS AND COMBINATIONS WITH PRP/BMC

(71) Applicant: REGEN LAB SA, Le Mont-sur-Lausanne (CH)

(72) Inventors: Antoine Turzi, Lauenen bei Gstaad (CH); Marta Mameli, Lausanne (CH)

(73) Assignee: REGEN LAB SA, Le Mont-sur-Lausanne (CH)

( * ) Notice: Subject to any disclaimer, the term of this patent is extended or adjusted under 35 U.S.C. 154(b) by 1133 days.

(21) Appl. No.: 16/966,454

(22) PCT Filed: Feb. 7, 2019

(86) PCT No.: PCT/IB2019/050973
§ 371 (c)(1),
(2) Date: Jul. 30, 2020

(87) PCT Pub. No.: WO2019/155391
PCT Pub. Date: Aug. 15, 2019

(65) Prior Publication Data
US 2022/0193116 A1 Jun. 23, 2022

Related U.S. Application Data

(60) Provisional application No. 62/626,984, filed on Feb. 6, 2018.

(51) Int. Cl.

| | |
|---|---|
| *A61K 31/728* | (2006.01) |
| *A61K 31/194* | (2006.01) |
| *A61K 31/738* | (2006.01) |
| *A61K 35/16* | (2015.01) |
| *A61K 35/19* | (2015.01) |
| *A61K 38/48* | (2006.01) |
| *C08B 37/08* | (2006.01) |

(52) U.S. Cl.
CPC .......... *A61K 31/728* (2013.01); *A61K 31/194* (2013.01); *A61K 31/738* (2013.01); *A61K 35/16* (2013.01); *A61K 35/19* (2013.01); *A61K 38/4833* (2013.01); *C08B 37/0072* (2013.01)

(58) Field of Classification Search
CPC .... A61K 31/728; A61K 31/738; A61K 35/16; A61K 31/194; A61K 35/19; A61K 38/4833; C08B 37/0072
See application file for complete search history.

(56) References Cited

U.S. PATENT DOCUMENTS

| | | | |
|---|---|---|---|
| 2006/0105022 A1 | 5/2006 | Yokokawa et al. | |
| 2014/0315828 A1 | 10/2014 | Pavlovic et al. | |

FOREIGN PATENT DOCUMENTS

| | | | | |
|---|---|---|---|---|
| WO | WO-2011110948 A2 * | 9/2011 | ........... | A61K 31/728 |
| WO | 2013185934 A1 | 12/2013 | | |
| WO | 2014055895 A1 | 4/2014 | | |
| WO | 2014121067 A1 | 8/2014 | | |
| WO | 2014198406 A1 | 12/2014 | | |
| WO | 2017136935 A1 | 8/2017 | | |
| WO | 2019155391 A1 | 8/2019 | | |

OTHER PUBLICATIONS

Falcone et al., J. Biomed. Mater. Res., 2006, 76A, p. 721-728. (Year: 2006).*

* cited by examiner

*Primary Examiner* — Jonathan S Lau
(74) *Attorney, Agent, or Firm* — Rahman LLC

(57) ABSTRACT

The invention provides a new method of synthesizing cross-linked hyaluronic acids, compositions thereof, tubes and syringes containing such compositions alone or in combination with PRP/BMC, new devices for PRP/BMC preparation, and uses thereof in cell culture, skincare and joint preservation. The invention provides a method for the production of a crosslinked gel (preferably of desired molecular weight and/or concentration) from at least one first polymer (preferably hyaluronic acid), comprising the steps of: homogenizing said first polymer, hydrating said first polymer in a basic solution, crosslinking said basic solution by adding at the least one crosslinking agent at a higher temperature than room temperature, neutralizing said basic solution in an acidic solution, homogenizing said solution, mixing said solution with a supplemental quantity of a second polymer (preferably a second polymer of substantially the same molecular weight and/or concentration as said first polymer), and purifying said solution.

19 Claims, 30 Drawing Sheets

CROSS-LINKED HYALURONIC ACIDS AND COMBINATIONS WITH PRP/BMC

FIELD OF THE INVENTION

The invention provides a new method of synthesizing cross-linked hyaluronic acids, compositions thereof, tubes and syringes containing such compositions alone or in combination with PRP/BMC, new devices for PRP/BMC preparation, and uses thereof in cell culture, skincare and joint preservation.

BACKGROUND

Crosslinked hyaluronic acid (herein also referred to as XLHA) has been produced by many companies with different processes. Gel obtained are mostly used for the preparation of syringes used for dermatological treatments. In general, depending on the quantity of BDDE used and/or the physical parameter adopted for the synthesis, the percentage of cross-linking can be modulated and gels with different viscoelastic properties and residence time can be produced.

In general, all the reported methods have some steps in common such as:
1) Initial hydration step during which the polymer under the physical form of powder or fibers is solubilized into a buffer media;
2) A crosslinking step where a cross-linking agent is added and the reaction carried on for a certain time at a certain temperature at specific pH conditions;
3) A phase of neutralization necessary in view that typically the application environment is the human body
4) And a last necessary phase of purification for eliminating the unreacted crosslinker.

Some intermediate phases are included such as swelling or addition of another polymer or anesthetic depending on the final formulation required and the properties aimed (viscosity, residence time, intended use, etc.) Analyzing these methods, it is clear that a lot of manipulations are involved.

Considering the important number of manipulations performed, the length of the synthetic procedure (time-consuming processes) and explosion of the products, alternative methods of preparing cross-linked hyaluronic acid is being proposed with compositions obtained having features enabling mixing with platelet rich plasma and bone marrow concentrate.

Further, cell therapy and regenerative therapy research implies in vitro cultures and proliferation of stem cells, progenitor cells, or differentiated cells for autologous therapy.

Fetal bovine serum (FBS), which is currently used as the main source of nutrients and growth factors for in vitro cultures, raises several ethical concerns (blood withdrawal from the living animals), safety concerns (viral, mycoplasma, protein contamination), results reproducibility concern (variations of the composition between the batches) and financial concern (major cost). For these reasons, sanitary authorities wish to get rid of FBS in cell therapy in human clinical protocols settings. Alternative media than FBS with medical devices enabling preparation of such media is therefore warranted.

Finally, hyaluronic acid compositions particularly adapted to be mixed with a platelet concentrate (PC) or bone marrow concentrate (BMC) are warranted.

BRIEF DESCRIPTION OF THE DRAWINGS

FIG. 20(A) shows migrating fibroblasts narrowed the width of the scratch zone as evidenced after 8 h with an immunofluorescence staining with phalloidin. The cell migration front is equally distributed along the in FBS 10% while it is less homogeneous in PRP 10%-treated cells. FIG. 20(B) are zoom in pictures showing isolated cell migration in FBS 10% cultures and collective cell migration in PRP 10% cultures. FIG. 20(C) shows an effect of 8 h treatment with increasing concentrations of PRP on NHDF migration in a wound healing assay.

FIG. 21(A) is an example of comparable homozygous deletion on chromosome 4 in q13.2 region, and FIG. 21(B) is a comparable benign heterozygous deletion on chromosome 3 in q29 region.

DESCRIPTION OF THE INVENTION

Figure 1:
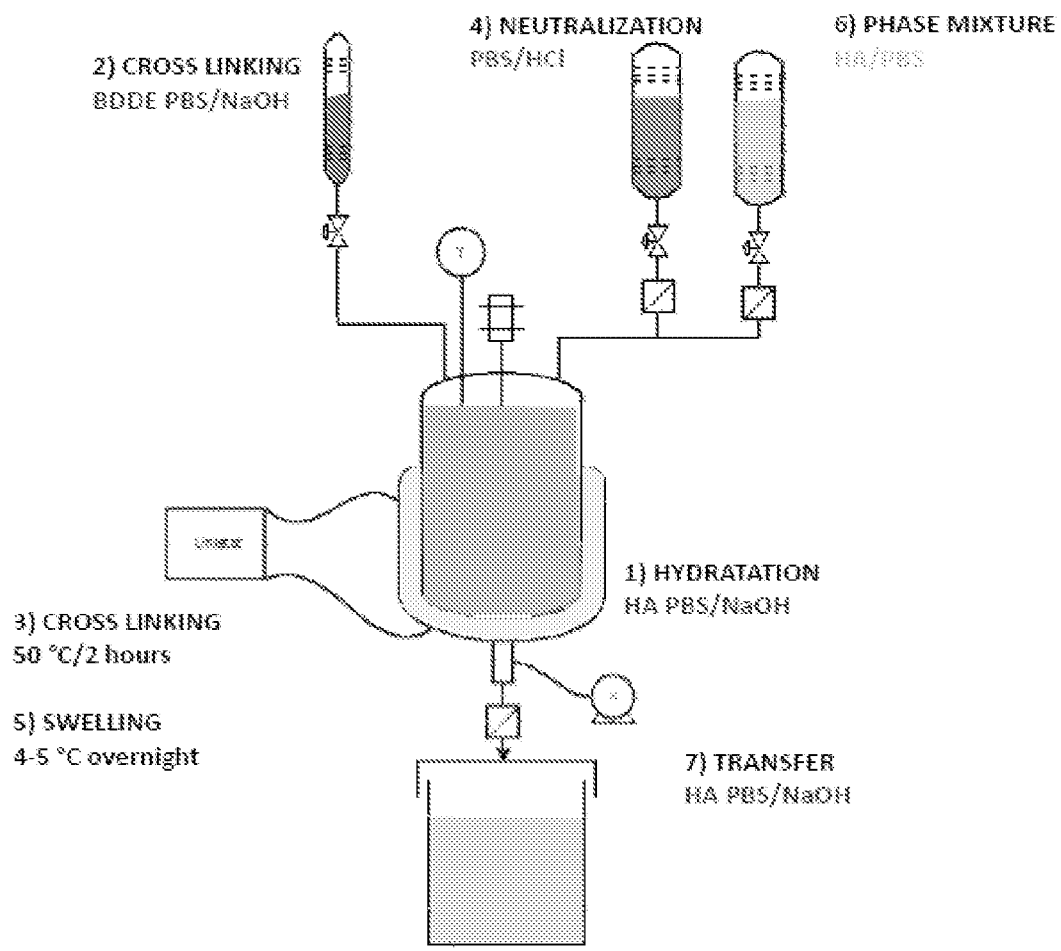
FIG. 1 and FIG. 2 shows a process vessel which can be used e.g. in the crosslinking of HA to form XLHA.

1. Crosslinked Hyaluronic Acid (XLHA); XL=Crosslinked; HA=Hyaluronic Acid

When HA is chemically modified to obtain a polymer, whose chains are connected between them, a cross linked hyaluronic acid is obtained (herein also referred to as XLHA).

XLHA is a hydrogel (hydrophilic gel) with an amorphous network, which can be crosslinked using a large number of agents. The preferred crosslinking agent according to the invention is 1,4-butanediol diglycidyl ether (BDDE) thanks to his less toxic nature.

The invention provides a container, preferably a tube, containing an anticoagulant, a thixotropic gel and a crosslinked HA. Such tubes (medical devices) are useful for the preparation of injections for the treatment of articular pain symptoms and joint mobility improvement as well as to prepare injection into mid to deep dermis for correction and modification of atrophic scars of traumatic or post-operative origin and for skin dehydration and correction of moderate to severe facial wrinkles and folds anatomy, such as nasolabial folds.

A crucial point for the preparation of such medical device is the mixture between PRP and HA. The gel must have a suitable viscosity to obtain a perfect and homogenous mixture of PRP and HA within 20 tube inversions, even though XLHA has a higher viscosity. Further, the XLHA shall be also be suitable for the preparation of syringes used in the main fields and for similar treatment, suitable for the gel to pass trough a 27 G needle.

The XLHA shall have a residence time longer than the 30 days of the non-XL gel, e.g. a residence time of approximately 3 months, with the XLHA completely absorbed in a period of 3 months yet leaving permanent therapeutic effects.

By modulating the % of cross-linking, the residence time will be changed always keeping in mind the viscosity restrictions. In fact, the higher is the % of cross linking, the higher is the residence time but the higher the viscosity might become.

It has been demonstrated through experiments that the hyaluronic acid compositions obtained advantageously display the above-mentioned characteristics.

Development of a Streamlined Method for the Synthesis of XLHA.

The method may be referred herein to a "one pot" method. A "one-pot" synthesis is defined as a strategy to improve the efficiency of a chemical reaction, whereby a reactant is subjected to successive chemical reactions in just one reactor. As long as a particular sequence of reactions is carried out in the same reactor, it is herein considered to be "one-pot".

The first aspect of the invention is a method of synthesis described in the Example section. The methods according to the invention may be conducted in an oxygen free atmosphere. Preferably, the method is conducted with a low humidity level. Preferably, the method is conducted under airflow, preferably continuous airflow. Alternatively to air, any inert gas may be used such as nitrogen or argon. Alternatively to a continuous gasflow, the method is conducted under vacuum or air aspiration. The method is performed in a single reaction vessel as a continuous process.

The invention provides also a method for the preparation of an injectable hydrogel, the process comprising the steps of homogenizing one or more polymers, hydrating the polymers, crosslinking the polymers to form a gel, neutralizing the gel, homogenizing the gel, adding one or more polymers to the gel to produce the hydrogel and purifying the hydrogel, and wherein the process is carried out in a single reaction vessel as a continuous process. Preferably, the method is conducted under airflow and using an anchor-stirrer vessel. Preferably, the crosslinking step is less than 4 hours, preferably about 2 hours. Preferably, the neutralization step is performed at pH 7 during about 12 hours. Preferably, following the neutralization step, the gel is left overnight at about 4° C. Preferably, the one or more polymers that are added to the gel are added at room temperature. Preferably, the one or more polymers that are added to the gel are of the same molecular weight and concentration as the initial polymers.

The polymer may have one or more reactive groups selected from hydroxyl groups, carboxyl groups and amine groups. The polymer may be a polysaccharide, a protein, or a synthetic polymer selected from the group consisting of poly(acrylic acid) and poly(vinyl alcohol). The polysaccharide may be selected among hyaluronic acid, chitosan, alginate acid, starch, dextran, or salts or water soluble derivatives thereof. Preferably, the method is carried out at neutral pH. Preferably, the crosslinking reaction is carried out at a temperature of about 50° C., for about 2 hours. Preferably, the crosslinking reaction is carried out for a period of time of less than 4 hours, less than 3 and half hours, less than 3 hours, or less than 2 hours and a half. Preferably, no impellers are used in the reaction vessel. Instead, an anchored-stirred vessel is used.

Herein reference to "about" can alternatively mean+−10 percent. Dynamic viscosity may herein be referred to a zero shear viscosity.

The start of starting crosslinking is carried out by the addition of a quantity of crosslinking agent which is a bi- or polyfunctional molecule selected from the compounds of the group consisting of epoxys, epihalohydrins and divinylsulfone. The preferred epoxys are compounds selected from the group consisting of: 1,4 butanediol diglycidyl ether (also called 1,4-bis(2,3-epoxypropoxy)butane), 1-(2,3-epoxypropyl) 2,3-epoxy cyclohexane and 1,2-ethanediol diglycidyl ether.

An epoxy based cross-linking agent having at least two epoxy functional groups in an aqueous alkaline solution may be used in a method of the invention.

The epoxy-based cross-linking agent having at least two epoxy functional groups may be selected from the group consisting of 1,4-butanediol diglycidyl ether (BDDE), ethylene glycol diglycidyl ether (EGDGE), 1,6-hexanediol diglycidyl ether, propylene glycol diglycidyl ether, polypropylene glycol diglycidyl ether, polytetramethylene glycol diglycidyl ether, neopentyl glycol diglycidyl ether, polyglycerol polyglycidyl ether, diglycerol polyglycidyl ether, glycerol polyglycidyl ether, trimethylpropane polyglycidyl ether, 1,2-(bis(2,3-epoxypropoxy)ethylene, pentaerythritol polyglycidyl ether, sorbitol polyglycidyl ether, and any combinations thereof.

The ethanol-containing aqueous alkaline solution may contain about 5 to about 13% w/w of ethanol. The ethanol-containing aqueous alkaline solution may be an aqueous sodium hydroxide solution of about 0.7 to 1.3% w/w containing about 5 to about 13% w/w of ethanol.

According to a particular embodiment of the invention, the step of starting crosslinking is carried out in a basic medium. The crosslinking reaction carried out in basic medium is characterized by the formation of ether bonds which are very solid. The crosslinking by etherification permits a longer remainance in vivo.

The crosslinking reaction is the reaction which ensures the bridging of the chains of each polymer with each other. It can be quantified by the determination of the amount of crosslinking.

The crosslinking can take place with a single polymer or with a mixture of polymers.

Alternatively to hyaluronic acid, other polymers may be used. Preferably, the polymers are of natural origin. The use of polymer of natural origin permits better biocompatibility, which is to say that such a use give rise to less risk of inflammatory reaction.

Preferably, the polymer of natural origin are compounds selected from the group consisting of: hyaluronic acid, chondroitine sulfate, keratan, keratan sulfate, heparin, heparin sulfate, cellulose and its derivatives, alginates, xanthane, carraghenin, proteins or nucleic acids.

Even more desirably, at least one polymer of natural origin is a polymer not naturally present in the human body, selected from the group consisting of: cellulose and its derivatives, alginates, xanthane, carraghenin, a polymer which is crosslinked with at least one polymer naturally present in the human body selected from the group consisting of: hyaluronic acid, chondroitine sulfate, keratan, keratan sulfate, heparin, heparin sulfate, proteins or nucleic acids.

The polymers taking part in the crosslinking reaction can be synthetic but are preferably of natural origin. The use of polymers of natural origin permits better biocompatibility, which is to say that such use gives rise to less risk of inflammatory reaction.

Preferably, there are used the above-mentioned polymers of natural origin.

It is however obvious that the invention is not limited to the above-mentioned polymers but can use polymers of different type and size.

Addition of supplemental polymers may take place at any level of progress of the initial crosslinking reaction, preferably at 75% of the initial crosslinking reaction. This step can be carried out by the addition of polymer in a continuous or discontinuous manner. The supplemental polymers may have a molecular weight greater than 500,000 Da.

They can also be synthetic or natural. They can be added in the form of a mixture of polymers. They can be of a nature or size identical to or different from those used in the initial crosslinkage step. Desirably, the added supplemental polymers are constituted by longer chains than the polymers initially present. This gives to the gel an improvement of its external mechanical structure, the long chains being more difficultly degraded than the short ones.

The hyaluronic acid may be obtained by fermentation with a microorganism. The hyaluronic acid includes hyaluronic acid, a salt of hyaluronic acid, or any mixtures thereof.

The salt of hyaluronic acid is selected from the group consisting of sodium hyaluronate, potassium hyaluronate, magnesium hyaluronate, zinc hyaluronate, cobalt hyaluronate, tetrabutylammonium hyaluronate, and any combinations thereof.

Alternatively to homogenizing/hydrating steps, the polymer or hyaluronic acid substrate is dissolved in a first liquid medium, which is an aqueous solution, without any cross-linking; Alternatively to homogenizing/hydrating steps, precipitating the polymer or hyaluronic acid substrate by subjecting it to a second liquid medium comprising an amount of one or more first water-soluble organic solvent(s) giving precipitating conditions for hyaluronic acid without any cross-linking.

Advantageously, no organic solvents are used in the present invention.

Method according to any of the preceding claims, wherein said method or part thereof is performed under inert atmosphere, under vacuum.

The invention has for its object to propose a biocompatible crosslinked gel which avoids known drawbacks, which has the advantages simultaneously of easy use in its clinical utilization and of a lifetime such that the biocompatible crosslinked gel disappears when its function is no longer desired, but sufficient to limit the number of administrations by medical or surgical intervention.

The step of stopping crosslinking may also be carried out by dialysis, simultaneously to the step of stopping crosslinking according to the invention, previously or subsequently to such step.

This process permits obtaining a biocompatible crosslinked gel having simultaneously the characteristics of being biphasic, polydensified, cohesive, injectable and with long remainance.

By cohesive, there is meant a tendency of the gel to regroup and not to spread out or break apart. The cohesive character thus contributes to obtaining a high compatibility and long remainance in vivo of the gel.

By polydensification, there is meant a variation of the degree of crosslinking even within the gel itself. The polydensified character of the gel permits the composition to acquire advantages of injectability through a needle of small diameter, and all remainance in vivo of the gel.

The effect of long remainance of the gel permits spacing the medical interventions and hence improving the quality of life of the patients.

Such a cohesive polydensified monophasic gel obtained according to the practice of the present invention is characterized by facilitated injectability and remainance in vivo longer than that of a monophasic gel of the same composition, whose amount of crosslinking is homogeneous within the gel.

The invention also has for its object a gel prepared by the above-mentioned process.

In one embodiment, the gel constitutes a matrix comprising at least one dispersed active ingredient. The gel will then be used as a vector permitting progressive release of said active ingredient from the liquid or the biological tissue in which it is injected. The active ingredient is a pharmacologically active agent that can for example be an antioxidant agent. The active ingredient can also be of a different nature. A mixture of active ingredients of different nature can also be dispersed in the gel.

This gel is preferably injected.

Further, the invention has for its object the use of this gel to separate, replace or fill a biological tissue or to increase the volume of said tissue for example in the case of therapeutic applications (increase in the volume of the vocal cords, of the esophagus, of the sphincter, of the urethra or other organs), for cosmetic purposes for the filling of wrinkles, the masking of scars, or the increase of the volume of the lip or else to supplement or replace a biological fluid. It can also supplement or replace a biological fluid, for example the natural synovial liquid.

The invention also provides a combination of cross-linked hyaluronic acids according to the invention.

The compositions of the present invention may be combined with chitosan, e.g. chitosan microbeads or unmodified macroporous chitosan microbeads. Such chitosan microbeads may be dispersed uniformly in a hyaluronic acid composition of the present invention, or combination of cross-linked and non-crosslinked hyaluronic acid.

The cross-linked hyaluronic acid compositions of the present invention may be combined with non-crosslinked composition. Further, such compositions may be combined with a platelet concentrate or bone marrow concentrate.

Additional components may be included to the compositions of the present invention, selected from a local anesthetic for control of injection pain, of the amide type, including lidocaine, prilocaine, bupivacaine, mepivacaine and articaine.

In another aspect, the invention provides:
i) a method for correcting facial imperfections, by injection with a 27 G or 30 G fine needle of the compositions of the present invention into the deep dermis or subcutaneously. The purpose is to soften the appearance of facial creases and wrinkles, such as nasolabial folds and marionette lines, to enhance shallow contours, to plump thin lips, or improve the appearance of recessed scars.
ii) a method for treating volume loss in the face due to a wasting condition such as lipoatrophy, by injecting a sufficient quantity of the compositions (herein also referred to as fillers) of the present invention, subcutaneously in the cheeks for example, to improve the appearance of the patient.

As mentioned, the present invention relates also new methods and medical devices enabling the preparation of Platelet Concentrates (PC) or Bone Marrow Concentrates (BMC) alone or in combination with biomaterials such as hyaluronic acid according to the invention, preferably in large volumes. It also relates to new formulations of hyaluronic acid particularly suitable in combination with PC and BMC: Such HA may be characterized as follows:
Dynamic viscosity of approx. max. 5 Pa·s (pascal second).
1500 Kda (between 500 KDa and 2000 KDa),
2% concentration (between 1% et 2.5%),
degree of crosslinking of about 3%
Further, HA suitable for syringes and similar devices where flow of said HA is important are characterized by an elasticity of up to 60 Pa·s, in order for the HA to flow correctly in a 27 G needle.

Dynamic viscosity and elasticity depends on % of concentration, degree of crosslinking and molecular weight. In order to get suitable viscosity, one can modulate these two factors.

A tube is herein characterized by a distal end and proximal end, with the proximal end having an aperture for the collection of material, substance or composition, e.g. whole blood, bone marrow.

In another aspect, the invention provides a composition or a device, preferably a tube or syringe, comprising or prefilled with a cell selector gel (e.g. thixotropic gel) and an anticoagulant. Preferably, the thixotropic gel is layered beneath the anticoagulant at the distal end of the tube. Tube may be characterized by a first layer of thixotropic gel followed by a second layer of anticoagulant followed with open space for the collection of a substance (e.g. whole blood, bone marrow or other substance). Such device being particularly adapted for the preparation of PRP or BMC: Thrombin (e.g. autologous thrombin serum) may be collected in the tube before or after collection of substance (e.g. whole blood, bone marrow or other substance). Adding thrombin enables jellification of substance (e.g. of PRP or BMC). Density of the thixotropic gel (herein also referred to as cell selector gel or CSG) is between 1.04 and 1.09 g/cm3, preferably between 1.045 g/cm3 and 1.075 g/cm3. Density of the gel may be 1.075 g/cm3, 1.07 g/cm3, 1.065 g/cm3, 1.06 g/cm3, 1.055 g/cm3, 1.05 g/cm3, 1.045 g/cm3 or 1.04 g/cm3.

In another aspect, the invention provides a composition or a device, preferably a tube or syringe, comprising or prefilled with a biomaterial and an anticoagulant. Preferably, the biomaterial is layered beneath the anticoagulant at the distal end of the tube. Tube may be characterized by a first layer of biomaterial followed by a second layer of anticoagulant followed with open space for the collection of a substance (e.g. whole blood, bone marrow or other substance). Biomaterial shall have a density lower than erythrocytes (1.09 to 1.1 g/cm3), i.e. lower than 1.09 g/cm3, lower than 1.085 g/cm3, lower than 1.08 g/cm3, lower than 1.075 g/cm3, lower than 1.07 g/cm3, lower than 1.065 g/cm3, lower than 1.06 g/cm3, lower than 1.055 g/cm3, lower than 1.05 g/cm3, lower than 1.045 g/cm3 or lower than 1.04 g/cm3. Advantageously, such configuration enables use of a biomaterial with an important density range, ranging from approx. 1 g/cm3 to a density lower than erythrocytes, i.e. lower than 1.09 g/cm3 and >=1 g/cm3. Such device is adapted for the preparation of PRP or BMC in combination with a biomaterial. In order to avoid mixing of anticoagulant with biomaterial, a suitable biomaterial may be used which is inert or hydrophobic. Alternatively, a substance or barrier is layered/positioned between the anticoagulant and biomaterial. Thrombin (e.g. autologous thrombin serum) may be collected in the tube before or after collection of substance (e.g. whole blood, bone marrow or other substance).

In one aspect, the invention provides a composition or a device, preferably a tube or syringe, comprising or prefilled with hyaluronic acid, preferably a HA composition of the present invention, chitosan and an anticoagulant. Preferably, the HA and chitosan are layered beneath the anticoagulant at the distal end of the tube. Tube may be characterized by a first layer of HA or chitosan followed by a second layer of HA or chitosan and a third layer of anticoagulant followed with open space for the collection of a substance (e.g. whole blood, bone marrow or other substance).

The invention therefore relates to sterile and non-pyrogenic containers, preferably tubes allowing the mix of a PC (for example Platelet Rich Plasma (PRP)) or BMC, with biomaterials, for example Hyaluronic Acid (HA) advantageously in the same proportion (e.g. 4 mL of PRP for 4 mL of HA), advantageously optionally in large volumes. In one embodiment, the invention relates to a medical device consisting of or comprising one tube for the preparation of PC or BMC and one tube prefilled with hyaluronic acid preferably connected through means of a device enabling transfer of PC or BMC into the tube prefilled with the biomaterial. Preferably such transfer occurs automatically, for example due to vacuum in the tube containing the biomaterial. The aspects and embodiments of the present invention enable the preparation of a combination of a Platelet Concentrate (PC) or Bone Marrow Concentrate (BMC) with a biomaterial or cell extract at a volume of at the least 3 ml, 4 ml, 5 ml, 6 ml, 7 ml, 8 ml, 9 ml, 10 ml or more.

The PC/BMC tube (tube allowing the preparation of PC and/or BMC) may allow the preparation of 4 mL of PRP/BMC and may contain an inert polyester cell-selector gel and a liquid anticoagulant. The HA tube is dedicated to the direct transfer of PRP/BMC from the PRP/BMC tube and its mix with Hyaluronic Acid. The HA tube may contain only a gel of hyaluronic acid, at about 4 mL. Both tubes are preferably for single use only and are designed to be used with sterile and single-use phlebotomy material provided in the same kit.

In another aspect, the invention provides a container for the preparation of Bone Marrow Concentrate (BMC) and/or Plasma Concentrate (PC), characterized in that:

a) said container comprises or is prefilled with:
  i) at the least one anticoagulant, and/or
  ii) at the least one filter and/or composition allowing separation of red blood cells (RBCs), preferably or optionally a cell selector gel (CSG), preferably or optionally a thixotropic gel, preferably or optionally an inert polyester CSG, and
  iii) optionally at the least one biomaterial preferably or optionally selected from hyaluronic acid, chitosan, silk protein or fibroin or any combination thereof, and
  iv) optionally at the least one blood, bone marrow, cells and/or platelet preservation and/or stimulating solution, preferably or optionally plasmalyte-A, and
b) optionally a collection device, optionally or preferably comprising or consisting of a collection holder with accessories, preferably or optionally a safety lock and butterfly needle, may be affixed to said container for collection of blood and/or bone marrow into said container and wherein said collection preferably or optionally occurs in closed circuit, preferably or optionally automatically, preferably or optionally by vacuum, and
c) optionally a collection device may be affixed to said container for collection of thrombin serum, preferably or optionally autologous thrombin serum, into said container and wherein said collection preferably or optionally occurs in closed circuit, preferably or optionally automatically, and
d) optionally a transfer device can be affixed to said container for the transfer of said PC and/or said BMC into another container, wherein said container is preferably or optionally a tube or syringe, preferably or optionally under vacuum, wherein said transfer preferably or optionally occurs in closed circuit, preferably or optionally automatically, preferably or optionally by vacuum, preferably or optionally either by direct contact between the two containers or through means of a device, and
e) optionally further comprises at least one filter or substance for the separation of other blood components and/or bone marrow components, optionally or preferably for lymphocytes,
f) said container optionally is under vacuum,
and may be suitable:
i) for collection of bone marrow and/or whole blood into said container, and
ii) for centrifugation, and
iii) optionally for vacuum and/or mixing and/or inversion of said container,
and may be suitable for either or both:
iv) collection of said PC and/or BMC from said container, and/or
v) transfer of said PC and/or BMC into another container.

"Suitable for" may herein (in any aspect or embodiment of the invention) be substituted by "when used in".

In accordance with this aspect of the invention, the container may contain either:
  i) at least one anticoagulant, or
  ii) at the least one filter and/or composition allowing separation of red blood cells (RBCs), preferably or optionally a cell selector gel (CSG), or
  iii) a combination of at least one anticoagulant and:
    a. at the least one filter, or
    b. composition allowing separation of red blood cells (RBCs), preferably or optionally a cell selector gel (CSG), or c. a combination of at the least one filter and a composition allowing separation of red blood cells (RBCs), preferably or optionally a cell selector gel (CSG).

In another aspect, the invention provides a container for the preparation of PC and/or BMC in combination with at the least one biomaterial preferably or optionally selected from hyaluronic acid, chitosan, silk protein or fibroin, cell extract or any combination thereof, characterized in that:
  a) said container comprises or is prefilled with a biomaterial preferably or optionally selected from hyaluronic acid, chitosan, silk protein or fibroin, cell extract or any combination thereof, and
  b) optionally a collection device, preferably or optionally comprising a collection holder, may be affixed to said container for the collection of PC and/or BMC into said container, and
  c) optionally said PC and/or BMC in combination with at the least one biomaterial can be collected, preferably or optionally in closed circuit, and
  d) said container optionally further comprises or is prefilled with a coagulation activator, preferably or optionally selected from thrombin serum, calcium gluconate and/or calcium chloride, and
  e) said container optionally is under vacuum,
  f) said container optionally contains two or more chambers wherein each chamber may contain a composition selected from a substance, biomaterial, cell extract, PC or BMC and/or coagulation activator, wherein said compositions are isolated from each other in their respective chamber and wherein said compositions may optionally enter into contact with each other or be mixed together inside and or outside said container, wherein said chambers are separated by a chemical or biological substance, membrane or any other means of separation, wherein such means of separation may optionally disintegrate over time or is biodegradable,
and may be suitable for:
  i) collection of PC and/or BMC from a PC and/or BMC container, preferably or optionally from the container of the first aspect, wherein said transfer optionally occurs in closed circuit, preferably or optionally automatically, preferably or optionally by vacuum, preferably or optionally either by direct contact between the two containers or through means of a collection device, and
  ii) optionally centrifugation, and
  iii) collection or transfer of said PC and/or BMC in combination with at the least one biomaterial into another device, preferably or optionally syringe, preferably or optionally in closed circuit, preferably or optionally automatically, and
  iv) optionally mixing and/or inversion.

In another aspect, the invention provides a syringe for the preparation of PC and/or BMC in combination with at the least one biomaterial preferably or optionally selected from hyaluronic acid, chitosan, silk protein or fibroin, cell extract or any combination thereof, characterized in that:
  a) said syringe comprises or is prefilled with a biomaterial preferably or optionally selected from hyaluronic acid, chitosan, silk protein or fibroin, cell extract or any combination thereof,
  b) optionally a collection device, preferably or optionally a collection holder, can be affixed to said syringe for the collection of PC and/or BMC into said syringe,
  c) optionally said syringe comprises or is prefilled with a coagulation activator, preferably or optionally selected from thrombin serum, calcium gluconate and/or calcium chloride,
  d) said syringe optionally contains two or more chambers wherein each chamber may contain a composition selected from a substance, biomaterial, cell extract, PC or BMC and/or coagulation activator, wherein said compositions are isolated from each other in their respective chamber and wherein said compositions may optionally enter into contact with each other or be mixed together inside and or outside said syringe, wherein said chambers are separated by a chemical or biological substance, membrane or any other means of separation, wherein such means of separation may optionally disintegrate over time or is biodegradable,
and may be suitable for:
  i) collection of PC and/or BMC from a PC and/or BMC container, preferably or optionally from the container of the first aspect of the invention, wherein said collection preferably or optionally occurs in closed circuit, either by direct contact between said syringe and said container or through means of a collection device, preferably or optionally automatically, and
  ii) optionally inversion, and
  iii) optionally application or injection of said PC and/or BMC in combination with at the least one biomaterial on or into a human or animal, preferably or optionally in closed circuit, preferably or optionally automatically.

In further embodiments, the invention provides a container or syringe according to any of the previous aspects further prefilled with or comprising:
  i) at the least one anticoagulant, and/or
  ii) at the least one filter and/or composition allowing separation of red blood cells (RBCs), preferably or optionally a cell selector gel (CSG), preferably or optionally a thixotropic gel, preferably or optionally an inert polyester CSG, and/or
  iii) optionally at the least one biomaterial preferably or optionally selected from hyaluronic acid, chitosan, silk protein or fibroin or any combination thereof, and/or
  iv) optionally at the least one PC or BMC preservation solution, optionally or preferably plasmalyte-A, and/or
  v) optionally at the least one coagulation activator, thrombin serum, tricalcium phosphate (TCP), a bone substitute, hyaluronic acid composition, calcium gluconate, calcium saccharate, chitosan, fibroin, fibroin-silk protein or fibroin proteins, growth factors, mannitol, collagen, albumin, ascorbic acid, cream, fat cells, fat tissue, bone marrow concentrate, lubricin, cd-gelatin, botulinum toxin and/or one or more cell extracts, preferably an autologous cell extract, selected from an extract of keratinocytes, bone marrow, fibroblasts, periosteum or corneal cells, melanocytes and Langerhans cells, fat cells, muscle cells such as myoblasts and satellite cells, osteoblasts, chondrocytes, umbilical cord cells, stem cells, mesenchymal stem cells (MSCs), preadipocytes, adipocytes, pre-endhotelial cells, Schwann cells or Achilles tendon cells.

In further embodiments, the invention provides the container or syringe according to any of the previous aspects or embodiments further characterized in that:
  a) at the least two containers, at the least one container and one syringe or at the least two syringes may be connected together through means of a connecting device enabling transfer of any substance, material, PC, BMC, cell extract or composition from one container or syringe to the other container or syringe,
b) said container is a tube, and/or
c) said tube or syringe allows the withdrawal of about 1 ml to about 20 ml of whole blood, bone marrow, PC or BMC, preferably or optionally about 2 ml to about 10 ml, preferably or optionally about 4 ml.
d) said container and/or syringe is sterile and/or non-pyrogenic, and/or
e) said container is suitable for the preparation of PRP, autologous PRP, PC, autologous PC and/or autologous BMC, and/or
f) said container is suitable for the preparation of about 2 ml to about 10 ml, preferably or optionally about 3 ml to about 6 ml, preferably or optionally about 4 ml of PRP, autologous PRP, autologous PC and/or autologous BMC, and/or
g) said syringe is prefilled with or comprises from about 0.5 ml to about 5 ml of biomaterial, preferably or optionally about 2 ml of biomaterial, and/or
h) said container is prefilled with or comprises from about 1 ml to about 4 ml of cell-selector gel, preferably or optionally from about 1.5 ml to about 3.5 ml, preferably or optionally about 1.5 ml, about 2 ml, about 2.5 ml or about 3 ml of cell-selector gel, and/or
i) said container comprises or is prefilled with about 0.2 ml to about 1 ml of anticoagulant, preferably or optionally about 0.6 ml of anticoagulant, preferably or optionally sodium citrate, from about 2% to about 6%, preferably or optionally about 4%, and/or
j) said container or syringe contains from about 1 ml to about 5 ml of hyaluronic acid, preferably or optionally about 2 ml of hyaluronic acid, and/or
k) said hyaluronic acid is in the form of a gel, and/or
l) said hyaluronic acid resides in a buffer, preferably or optionally phosphate buffer, preferably or optionally comprising or consisting of sodium chloride, dipotassium hydrogenphosphate, potassium dihydrogenphosphate, potassium chloride and water, and/or
m) said hyaluronic acid is suitable for injection, mesotherapy, and/or application, and/or
n) said hyaluronic acid is present from about 40 mg to about 200 mg per container, preferably or optionally about 80 mg per container, and/or
o) said hyaluronic acid has a molecular weight of about 1000 KDa to about 2000 KDa, preferably or optionally about 1550 KDa, and/or
p) said hyaluronic acid is at about 0.1% to about 3%, preferably about 1% to about 2%, and/or
q) said hyaluronic acid is obtained by fermentation, and/or
r) said container is prefilled:
  1. during the manufacturing process and/or
  2. before centrifugation, either before and/or after collection of blood or bone marrow into said container, and/or
  3. with at the least one substance, biomaterial, gel and/or anticoagulant or any combination thereof and is contained in a kit or medical device.

In another aspect, the invention provides a medical device or kit consisting of or comprising either:
a) at the least one container and/or at the least one syringe according to any of the aspects or embodiments.
b) at the least one container of the first aspect of the invention, at the least one container of the second aspect of the invention and/or at the least one syringe of the third aspect of the invention or any combination thereof,
c) at the least one container of the first aspect of the invention and at the least one container of the second aspect of the invention,
d) at the least one container of the first aspect of the invention and at the least one syringe of the third aspect of the invention,
e) at the least one container of the first aspect of the invention, at the least one container of the second aspect of the invention and at the least one syringe of the third aspect of the invention,
f) at the least one container of the second aspect of the invention and at the least one syringe of the third aspect of the invention,
g) at the least one container of the first aspect of the invention for the preparation of PC and at the least one container of the first aspect of the invention for the preparation of BMC,
h) at the least one container of the first aspect of the invention for the preparation of PC and/or at the least one container of the first aspect of the invention for the preparation of BMC, and at the least one container of the second aspect of the invention comprising or prefilled with a cell extract and at the least one container of the second aspect of the invention comprising or prefilled with hyaluronic acid, chitosan, silk protein or fibroin or any combination thereof,
i) at the least one container of the first aspect of the invention for the preparation of PC and/or at the least one container of the first aspect of the invention for the preparation of BMC, and at the least one container of the second aspect of the invention comprising or prefilled with a cell extract and at the least one syringe of the third aspect of the invention comprising or prefilled with hyaluronic acid, chitosan, silk protein or fibroin or any combination thereof,
j) at the least one container of the first aspect of the invention for the preparation of PC and/or at the least one container of the first aspect of the invention for the preparation of BMC, and at the least one syringe of the third aspect of the invention comprising or prefilled with a cell extract and at the least one container of the second aspect of the invention comprising or prefilled with hyaluronic acid, chitosan, silk protein or fibroin or any combination thereof,
wherein said medical device or kit optionally further comprises:
k) a the least one container of the first aspect of the invention, a container of the second aspect of the invention and/or a syringe of the third aspect of the invention or any combination thereof, and/or
l) a the least one container for the preparation of thrombin serum, preferably autologous thrombin serum, and/or
m) a connecting device enabling transfer of any substance, material, PC, BMC, cell extract or composition from one container or syringe to another container or syringe.

In further embodiments, the invention provides a medical device or kit comprising:
a) the container according to the first aspect of the invention, and
b) the container of the first aspect of the invention, the container of the second aspect of the invention or the syringe of the third aspect of the invention, and c) optionally a collection device for collecting blood or bone marrow preferably or optionally comprising or consisting of a collection holder with preferably or optionally a safety lock and butterfly needle, and
d) optionally a collection device preferably or optionally comprising or consisting of a collection holder and transfer device for collecting PC and/or BMC into said container of the first aspect of the invention, said container of the second aspect of the invention and/or said syringe of the third aspect of the invention, and
e) optionally accessories and/or single use phlebotomy material.

In further embodiments, the invention provides a medical device or kit comprising:
a) a tube for the preparation of PRP or BMC under vacuum allowing the withdrawal of about 4 mL of blood or bone marrow which contains:
 ii. about 2.5 mL of inert cell-selector gel
 iii. about 0.6 mL of anticoagulant, preferably or optionally sodium citrate at about 4%,
b) a tube under vacuum allowing the withdrawal of about 4 mL of PRP or BMC from said tube a), which contains about 2 mL of hyaluronic acid gel in phosphate buffer, preferably or optionally sodium chloride, dipotassium hydrogenphosphate, potassium dihydrogenphospate, potassium chloride and water for injection,
c) a collection device for collecting blood and/or bone marrow consisting of a collection holder with a safety lock and butterfly needle,
d) a collection device preferably or optionally consisting of a collection holder and transfer device for collecting PC and/or BMC from said tube a) into said tube b).

In further embodiments, the invention provides a medical device or kit comprising:
a) a tube for the preparation of PRP or BMC under vacuum allowing the withdrawal of about 4 mL of blood or bone marrow which contains:
 i. about 2.5 mL of inert cell-selector gel
 ii. about 0.6 mL of anticoagulant, preferably or optionally sodium citrate at about 4%,
b) a syringe allowing the withdrawal of about 4 mL of PRP or BMC from said tube a), which contains about 2 mL of hyaluronic acid gel in phosphate buffer, preferably or optionally sodium chloride, dipotassium hydrogenphosphate, potassium dihydrogenphospate, potassium chloride and water for injection,
c) a collection device for collecting blood and/or bone marrow consisting of a collection holder with a safety lock and butterfly needle,
d) a collection device preferably or optionally consisting of a collection holder and transfer device for collecting PC and/or BMC from said tube a) into said syringe b).

In further embodiments, the invention provides a medical device or kit according to any of the previous aspects or embodiments, further comprising a tissue harvesting cannula, preferably or optionally a fat-tissue harvesting cannula, a cannula for injection preferably or optionally straight or concave, a piston stopper, at the least one self-adhesive disc, a luer connector, anesthetic solution, injection accessories such as needles and/or syringes, syringes for tissue harvesting and mixing preferably or optionally luer-lock syringes, at the least one transfer cannula, a clip device, a container with dispenser for dispensing PC and/or BMC, a trocar, ampoule of coagulation activator such as calcium chloride or calcium gluconate, a paper mask, a device for the simultaneous release of PC and thrombin serum or any other combination of PC, BMC, substance, biomaterial or coagulation activator, wherein such device comprises at least one syringe, a nozzle for spray application, a double piston stopper, an applicator syringe holder and/or a connector, or any combination thereof.

In another aspect, the invention provides at least one, two, three, four, five, six, seven, eight, nine, ten or more container(s) and/or syringe(s) according to any of the previous aspects or embodiments, for use in therapy, dermatology, dentistry, orthopedics, sports medicine, cosmetics, esthetics, surgery, ophthalmology, mesotherapy, injections, infiltrations, subcutaneous applications, wound care, volume enhancement, volume corrections, mechanical support and/or visco-supplementation.

In another aspect, the invention provides a composition, preferably PC and/or BMC optionally in combination with at the least one biomaterial preferably selected from hyaluronic acid, chitosan, silk protein or fibroin or any combination thereof, obtained using at least one, two, three, four, five, six, seven, eight, nine, ten or more container(s) and/or syringe(s) according to any of the previous aspects or embodiments or obtained by using a method according to any of the previous aspects or embodiments, said composition optionally further combined with a coagulation activator, thrombin serum, tricalcium phosphate (TCP), a bone substitute, hyaluronic acid composition, calcium gluconate, calcium saccharate, chitosan, fibroin, fibroin-silk protein or fibroin proteins, growth factors, mannitol, collagen, albumin, ascorbic acid, cream, fat cells, fat tissue, bone marrow concentrate, lubricin, cd-gelatin, botulinum toxin and/or one or more cell extracts, optionally or preferably an autologous cell extract, selected from an extract of keratinocytes, bone marrow, fibroblasts, periosteum or corneal cells, melanocytes and Langerhans cell, fat cells, muscle cells such as myoblasts and satellite cells, osteoblasts, chondrocytes, umbilical cord cells, stem cells, mesenchymal stem cells (MSCs), preadipocytes, pre-endhotelial cells, Schwann cells or Achilles tendon cells, wherein said composition is preferably or optionally for use in therapy, dermatology, dentistry, orthopedics, sports medicine, cosmetics, esthetics, surgery, ophthalmology, mesotherapy, injections, infiltrations, subcutaneous applications, wound care, volume enhancement, volume corrections, mechanical support and/or visco-supplementation.

In another aspect, the invention provides a method of treatment for healing of wounds or tissues or for promoting bone or periodontium growth and/or bone and/or tissue regeneration such as skin, cartilage, muscle, tendon, ligament, adipose tissue, cornea, peripheral nerves, spine or bone using at least one, two, three, four, five, six, seven, eight, nine, ten or more container(s) and/or syringe(s) according to any of the previous aspects or embodiments.

In another aspect, the invention provides for the use of a composition, method, medical device, kit, container or syringe according to any of the previous aspects or embodiments in therapy, dermatology, dentistry, orthopedics, sports medicine, cosmetics, esthetics, surgery, ophthalmology, mesotherapy, injections, infiltrations, subcutaneous applications, wound care, volume enhancement, volume corrections, mechanical support and/or visco-supplementation, on/for a wound, a damaged tissue, damaged bone or periodontal defect or cavity, for cellular regeneration, for tissue adhesion, for promoting wound healing or tissue healing and/or sealing and/or regeneration of a tissue and/or a cartilage and/or a bone and/or a nerve in a wound or tissue of a human or animal, or for inducing periodontal regeneration in a wound or a periodontal defect of a mammal with periodontal disease or other condition requiring periodontal regeneration, or for ligament and/or cartilage reconstitution, or for promoting skin regeneration in a scar or a wrinkle, or for increasing adipose tissue volume in a mammal with a dermal fat graft or other condition requiring adipose tissue regeneration, or for inducing myocardial regeneration in a mammal with myocardial deficiency or other condition requiring myocardial regeneration tissue regeneration, or for inducing corneal regeneration in a mammal with corneal deficiency or other condition requiring corneal regeneration, or for inducing articular or cartilage regeneration in a mammal with articular or cartilage deficiency or other condition requiring articular or cartilage tissue regeneration, or for promoting skin regeneration in a scar, a wrinkle or a fat deficiency from human or lower animal, or for inducing peripheral nerve regeneration in a mammal with peripheral nerve damage, nerve suture or spinal cord injury or other condition requiring peripheral nerve regeneration, or for inducing bone regeneration in a mammal with bone damage, bone deficiency or other condition requiring bone regeneration, or for injections for orthopedic and injections for esthetic, or for regeneration and/or rejuvenation of skin tissues, particularly in promoting and/or initiating skin regeneration such as reducing skin wrinkles, deep wrinkles, acne, burns, rubella or small pox scars, vitiligo and lipoatrophy, amelioration of nasolabial lines and treatment of skin damages or disorders such as skin burns, Kaposi's sarcoma, skin skeloids or Dupuytren's palmar fibromatosis and in the reduction of pain associated with skin and tissue regeneration, or for wound or tissue healing or regeneration treatments, especially the treatment of traumatic or surgical wounds such in the fitting and/or holding and/or sealing of native or prosthetic grafts; treatment of vasculitis; ulcers such as diabetic neuropathic ulcers or decubitus sores, diabetic ulcer, perforating ulcer or diabetic perforating ulcer, arthritis, osteoarthritis, pseudo-arthritis, radio dermatitis and closing fistulas, fistulas or for cardiac disorders, cardiac regeneration such as in the treatment of heart failure, chronic cardiac failure, ischemic and non-ischemiccardiac failure and cardiomyopathy, or for bone, cartilage and articular disorders such as chondral damage, cartilage and/or bone injury such as deep cartilage damage and/or erosion and/or arthroscopy, tendon torn and rotator cuff in shoulder, or for corneal disorders such as dry eye syndrome; corneal opacity such as those caused by chemical burns, affliction by Steven's Johnson syndrome; scarring of the cornea and corneal ulcers, or for peripheral nerve damage, nerve suture and spinal cord injury, diabetic wounds, large vascular wounds, deep injections, intra dermal injections, intra-articular infiltrations, ophthalmic collyre, eyewash, for articulations, muscular lesions, as a mask post laser, post peeling, monotherapy, for glitter, gloss, brilliance or brightness.

In one embodiment, the invention relates to a medical device comprising or consisting of:
a. a safety-Lock Butterfly needle assembled with collection holder,
b. a preassembled transfer device
c. a tube under vacuum allowing the withdrawal of blood, which contains:
  i) about 2.5 mL of inert cell-selector gel,
  ii) about 0.6 mL of anticoagulant (e.g., sodium citrate 4%),
d. a tube under vacuum allowing the withdrawal of PRP, which contains about 2 mL of hyaluronic acid gel in phosphate buffer (Sodium chloride, Dipotassium hydrogenphosphate, Potassium dihydrogenphosphate, Potassium chloride and water for injection), with Hyaluronic Acid preferably at about 80 mg per tube, at about 1550 KDa and preferably obtained from fermentation.

All hyaluronic acid mentioned herein may relate to a hyaluronic acid obtained from any method according to the invention or to any hyaluronic acid composition according to the invention.

The containers and syringes of the present invention may be applied on large or deep wounds, or as biological glue.

The containers and syringes of the present invention containing a biomaterial are preferably sterilized by moist steam and preferably packaged under low germ atmosphere. Other containers, syringes or components of the present invention, e.g., tubes for the preparation of PC, basic phlebotomy material are preferably sterilized by exposure to a minimum dose of about 25 kGy gamma irradiation after preferably double blister packaging.

A cell selector gel may herein be referred to as a polymer or thixotropic gel.

Other substances described herein may be combined during one or more of the steps of a manufacturing method of the invention.

In another aspect, the invention provides a method of automatically manufacturing containers or hematology tubes by means of a filling machine comprising controlled vacuum and clogging of the containers or hematology tubes.

In one embodiment, the containers or syringes according to any aspects or embodiments of the present invention are prefilled with a substance selected from agar, gelose, collagen, chitosan, growth factors, ascorbic acid, albumin, fibroin, silk protein or fibroin-fibroin proteins or hyaluronic acid.

Agar, gelose, collagen, ascorbic acid, albumin, silk protein or fibroin-fibroin proteins may all display stabilizing and/or viscosity properties useful for a composition of the present invention. In one embodiment, hyaluronic acid or chitosan may be substituted by or combined with agar, gelose, collagen, ascorbic acid, albumin, fibroin and/or silk protein or fibroin-fibroin proteins. Preferably, hyaluronic acid or chitosan may be substituted by or combined with fibroin or silk protein or fibroin-fibroin proteins. In one embodiment, fibroin or silk protein or fibroin-fibroin proteins may be combined with PC and/or BMC. In another embodiment, fibroin or silk protein or fibroin-fibroin proteins may be combined with chitosan and/or HA in combination with PC and/or BMC. In another embodiment, albumin may be combined with PC and/or BMC. In another embodiment, albumin may be combined with chitosan and/or HA in combination with PC and/or BMC. In another embodiment, albumin may be combined with chitosan and/or HA, silk protein or fibroin-fibroin proteins, and further combined with PC and/or BMC.

In one embodiment, a substance selected from agar, gelose, collagen, chitosan, growth factors, ascorbic acid, albumin, fibroin, silk protein or fibroin-fibroin proteins or hyaluronic acid, and/or any combination thereof may be prefilled in containers or syringes according to any aspects or embodiments of the present invention.

In one embodiment, instead of or in combination with hyaluronic acid, a similar substance may be used or combined, for example gelose, agar, collagen chitosan, albumin and/or silk protein or fibroin-fibroin proteins, and/or any combinations thereof.

Preferably, the anticoagulant is citrate or sodium citrate.
Preferably, the polymer is a thixotropic gel.
Preferably, the container, tube, syringe, kit or device is for human use or human treatment. In one embodiment, the container, tube, syringe, kit or device may be used for animals, or adapted for veterinary use or animal treatment.

Preferably, the method of manufacturing according to any of the previous aspects is performed under laminar flow and/or bioburden controlled.

The containers, tubes or syringes may be of different shapes and made of crystal, glass, plastic or metal. Preferably, the containers, tubes or syringes are made of plastic, preferably COP or COC, preferably without phtalates.

In another embodiment, the invention provides hyaluronic acid (HA) of about 1000 KDa to about 2000 KDa at about 1.5% to about 2.5% concentration, of about 1400 KDa to about 1600 KDa at about 1.8% to about 2.2% concentration, of about 1550 KDa at about 1.8% to about 2.2% concentration, more preferably from about 1.7% to about 2% concentration. Such HA are particularly adapted for injections or infiltrations, intra dermal injections, subcutaneous applications, intra-articular infiltrations, fistulas and/or as a biological glue.

Such compositions of hyaluronic acid of are also adapted for a combination with a platelet concentrate, preferably a platelet rich plasma (PRP). Further suitable characteristics of HA compositions are described herein for combination with PC and BMC.

In one embodiment, the present invention encompasses a combination of at least two hyaluronic acids differing in molecular weight and in concentration.

In another aspect, the invention provides medical devices comprising tubes with different thixotropic gels having different densities.

In another aspect, the invention provides tubes with thixotropic gels having new densities useful for separating blood components in a targeted manner for new uses and applications.

In another aspect, the invention provides medical devices particularly adapted for cell culture.

Definitions and Formulae

Some definitions as used in/in respect of the present specification and/or the present invention

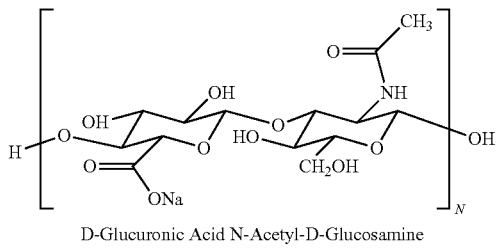

D-Glucuronic Acid N-Acetyl-D-Glucosamine

Structure 1A1 (above): Typical structure of the hyaluronic acid (HA) monomer (N=1) and/or of the HA polymer (N>1) (reproduced from Ahmet Tezel & Glenn H. Fredrickson, *Journal of Cosmetic and Laser Therapy*, 2008; 10: 35-42). "Polymer" as defined herein includes within its scope "oligomer"; and independently "poly-" includes within its scope "oligo-"; unless the context clearly indicates otherwise. HA polymers are preferred (N>1, preferably N=2 to 25000 or more); HA monomers are less preferred. In the chemical structure shown above, the HA is shown in the form of the sodium salt of the deprotonated carboxylate or polycarboxylate form of HA, but this is not the only structure covered by the term "HA".

"Hyaluronic acid" ("HA") as defined herein includes a or the carboxylic acid form(s) and/or polycarboxylic acid form(s) of the above-shown Structure 1A1 and, independently, includes any salt form(s), in particular any anionic (preferably polyanionic) salt form(s), of the above-shown Structure 1A1 (in particular any pharmaceutically-acceptable metal and/or ammonium and/or organoammonium salt(s) of the above-shown Structure 1A1, preferably any pharmaceutically-acceptable alkali metal salt(s) and/or alkaline earth metal salt(s) of the above-shown Structure 1A1, more preferably any lithium, sodium, potassium, calcium and/or magnesium salt(s) of the above-shown Structure 1A1).

Preferably, "hyaluronic acid" ("HA") as defined herein includes a or the carboxylic acid form(s) and/or polycarboxylic acid form(s) of the above-shown Structure 1A1, and, independently, includes any salt(s) (e.g. any of those salt(s) listed above, more preferably any lithium, sodium, potassium, calcium and/or magnesium salt(s)) of a or the carboxylate form(s) and/or polycarboxylate form(s) and/or polyanionic form(s) of the above-shown Structure 1A1.

In an analogous manner, as defined herein, "cross-linked hyaluronic acid" ("XLHA" or "XL HA") includes a or the carboxylic acid form(s) and/or polycarboxylic acid form(s) of the XLHA structure e.g. as defined in general terms herein (e.g. see Structures 1A4(A) and/or 1A4(B) hereinbefore and/or hereinafter) and, independently, includes any any salt form(s), in particular any anionic (preferably polyanionic) salt form(s), of the XLHA structure e.g. as defined in general terms herein (e.g. see Structures 1A4(A) and/or 1A4(B) herein) (e.g. any of those salt(s) listed above for HA).

Preferably, "XLHA" as defined herein includes a or the carboxylic acid form(s) and/or polycarboxylic acid form(s) of the XLHA structure e.g. as defined in general terms herein, and, independently, includes any salt(s) (in particular any pharmaceutically-acceptable metal and/or ammonium and/or organoammonium salt(s), preferably any pharmaceutically-acceptable alkali metal salt(s) and/or alkaline earth metal salt(s), more preferably any lithium, sodium, potassium, calcium and/or magnesium salt(s)) of a or the carboxylate form(s) and/or polycarboxylate form(s) and/or polyanionic form(s) of the XLHA structure e.g. as defined in general terms herein (e.g. see Structures 1A4(A) and/or 1A4(B) herein).

HA can be crosslinked to form XLHA using a large number of crosslinking agents, preferably with a di-epoxide crosslinking agent. The most used crosslinking agent for biomedical applications is the 1,4-butanediol diglycidyl ether (BDDE) thanks to its less toxic nature (see e.g. Jeon, O., et al., *Carbohydrate Polymers*, 70, (2007), 251-257). The structure of BDDE is shown below; most importantly, the structure contains two epoxide groups, one at each end of the linear organic molecule:

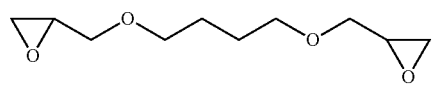

Structure of 1,4-butanediol diglycidyl ether (BDDE) (above)

A preferred generalized structure of a di-epoxide cross-linking agent (crosslinker), preferably suitable for use in cross-linking HA, is shown below:

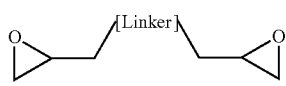
[Structue 1A3]

In the above generalized di-epoxide crosslinking agent (crosslinker) [Structure 1A3], the illustrated linker, shown as "[linker]", is preferably an organic linker moiety and/or preferably is of a length and/or structure suitable for cross-linking HA polymers e.g. suitable for cross-linking HA polymers at their —OH groups. Preferably, the [linker] comprises a chain of 2 to 20 atoms (preferably of 3 to 12 atoms e.g. 4 to 8 atoms e.g. 6 atoms) in length. (The chain is preferably linear, but optionally it can be branched.) More preferably, the [linker] comprises a chain (preferably linear chain) of 2 to 20 (or 3 to 12, or 4 to 8, e.g. 6) atoms in length wherein the chain atoms comprise chain carbon atoms (e.g. as —CH$_2$— or —CHMe- or —CMe$_2$— groups (Me=methyl)); and wherein optionally the chain atoms also comprise 1, 2, 3 or 4 chain oxygen, chain sulfur and/or chain nitrogen atoms (preferably the chain atoms also comprise 1, 2, 3 or 4, preferably 1 or 2, chain oxygen atoms).

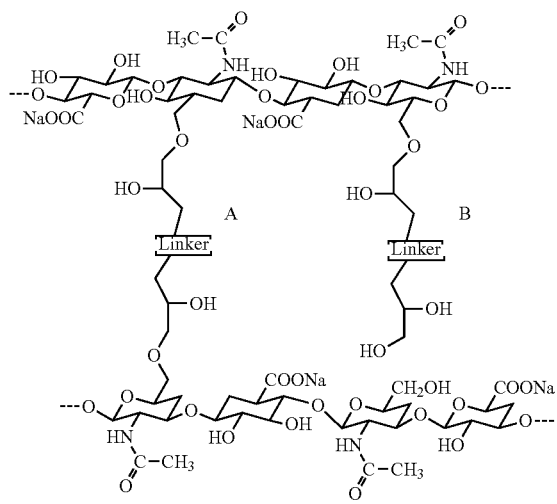

Structures 1A4(A) and 1A4(B) (above): Preferable generalized structure(s) of cross-linked HA (XLHA).

Partial Structure 1A4(A), on the left, illustrates in general terms a generalized crosslinking chain (A), which is formed by reaction of generalized di-epoxide cross-linker (cross-linking agent) (Structure 1A3) with the —OH groups of two HA polymer chains.

Partial Structure 1A4(B), on the right, illustrates in general terms a generalized pendant chain or group (B), which is attached to one HA or XLHA polymer chain only, which is formed by i) reaction of one epoxide group of a or the generalized di-epoxide crosslinking agent (Structure 1A3) with the —OH group of one HA polymer chain, plus ii) hydrolysis (eg by water or hydroxide) of the second epoxide group of the mono-HA-linked linker.

For convenience, Partial Structures 1A4(A) and 1A4(B) are shown to be both present at adjacent positions on two crosslinked HA chains—however, this is for illustrative purposes only, and the structure(s) of XLHA can include 1A4(A) only, or 1A4(B) only, or both, and the relative distance between A and B type linkers/groups, and the relative proportion of A and B type linkers/groups, and the % crosslinking and the % of pendant groups, are all variable.

In the above generalized Structures 1A4(A) and 1A4(B) of cross-linked HA, the illustrated linker, shown as "[linker]", is preferably an organic linker moiety and/or preferably is of a length and/or structure suitable for cross-linking HA polymers e.g. suitable for cross-linking HA polymers at their —OH groups. Preferably, the [linker] comprises a chain of 2 to 20 atoms (preferably of 3 to 12 atoms e.g. 4 to 8 atoms e.g. 6 atoms) in length. (The chain is preferably linear, but optionally it can be branched.) More preferably, the [linker] comprises a chain (preferably linear chain) of 2 to 20 (or 3 to 12, or 4 to 8, e.g. 6) atoms in length wherein the chain atoms comprise chain carbon atoms (e.g. as —CH$_2$— or —CHMe- or —CMe$_2$— groups (Me=methyl)); and wherein optionally the chain atoms also comprise 1, 2, 3 or 4 chain oxygen, chain sulfur and/or chain nitrogen atoms (preferably the chain atoms also comprise 1, 2, 3 or 4, preferably 1 or 2, chain oxygen atoms).

Note: The exact form of XLHA, and/or the salt form (if any) of XLHA, and/or the positions (within the XLHA polymer) and/or the proportions or percentages of any crosslinking chains (e.g. in Structure 1A4(A) above) and optionally any pendant chains (e.g. in Structure 1A4(B) above), can be varied considerably from what is shown in the structure above, which is an example structure only for illustrative purposes. The pendant chains (e.g. of the type shown in Structure 1A4(B) above) are optional—they may or may not be present in XLHA. The crosslinking chains (preferably of the type shown in Structure 1A4(A) above) are present in crosslinked hyaluronic acid (XLHA). The XLHA is shown above in the polyanionic (polycarboxylate) form, and as the sodium salt; however, in the present invention, any form (e.g. polyanionic or acidic or otherwise) of XLHA and/or any salt form of XLHA is possible.

In the present invention & specification, "residence time" is preferably defined and/or is preferably measured according to the method disclosed in ISO_10993-6_2016 (i.e. or preferably, linear HA is completely degraded after 1 month). In particular in the present invention(s), e.g. because of the cross-linked network of the XLHA, the gel and/or the XLHA preferably has a residence time longer than the residence time (usually about 30 days residence time) of a non-crosslinked (non-XL) HA gel (e.g. a corresponding and/or typical and/or conventional non-XL HA gel).

$$\text{Soluble Fraction } (w/w \text{ \%}) = \frac{HA \text{ concentration in the permeate (mg/ml)}}{\text{total } HA \text{ concentration}} * 100$$

$$( = 4 \text{ mg/ml})$$

Number average molecular weight $M_n$: is the statistical average Molecular weight of all the polymer chains in the sample, and is defined by:

$$Mn = \frac{\Sigma \, NiMi}{\Sigma \, N_i}$$

where $M_i$ is the molecular weight of a chain and Ni is the number of chains of that molecular weight. If $M_n$ is quoted for a molecular weight distribution, there are equal numbers of molecules on either side of $M_n$ in the distribution.

Weight average molecular weight $M_w$: is defined by $$Mn = \frac{\sum N_i M_i^2}{\sum N_i M_i}$$

Compared to $M_n$, $M_w$ takes into account the molecular weight of a chain in determining contributions to the molecular weight average. The more massive the chain, the more the chain contributes to $M_w$. If $M_w$ is quoted for a molecular weight distribution, there is an equal weight of molecules on either side of $M_w$ in the distribution.

For all synthetic polydisperse polymers: $M_n < M_w$

The polydispersity index is used as a measure of the broadness of a molecular weight distribution of a polymer, and is defined by:

$$Polydispersity\,index = \frac{Mw}{M_n}$$

The larger the polydispersity index, the broader the molecular weight. A monodisperse polymer where all the chain lengths are equal (such as a protein) has an $M_w/M_n=1$. The best controlled synthetic polymers (narrow polymers used for calibrations) have $M_w/M_n$ of 1.02 to 1.10. Step polymerization reactions typically yield values of $M_w/M_n$ of around 2.0, whereas chain reactions yield $M_w/M_n$ values between 1.5 and 20.

Note: Whenever "molecular weight" is referred to herein and/or in respect of the present invention(s), then, unless stated otherwise, it refers to Weight average molecular weight $M_w$ and/or Number average molecular weight $M_n$; and preferably refers to Weight average molecular weight $M_w$.

Intrinsic Viscosity: reflects the capability of a polymer in solution to enhance the viscosity of the solution.

Refractive index increment dn/dc: The refractive index increment applies to the sample under a specific condition. For example, temperature, laser wavelength, conformation of the molecule, or additives influence the absolute value of dn/dc. Thus, for a perfect static light scattering experiment the exact dn/dc at the conditions under consideration should be determined. In many practical examples, the value can be taken from prior datasets taken under similar conditions (or from literature references).

Hydrodynamic radius $R_h$: as measured by dynamic light scattering, is defined as the radius of an equivalent hard sphere diffusing at the same rate as the molecule under observation. In reality, solutions of proteins and their complexes do not exist as hard spheres and so, the determined hydrodynamic radius more closely reflects the apparent size adopted by the solvated, tumbling molecule.

Mark-Houwink-Sakurada relation MHS: empirical relationship that works well for correlating intrinsic viscosities and molecular weights of fractionated samples. It is used for completing a conformational analysis of a given polymer.

Complex Viscosity: Complex shear Modulus. The overall resistance to deformation of a material, regardless of whether that deformation is recoverable (elastic) or non-recoverable (viscous). Symbol G* complex viscosity=viscosity−i×elasticity Share Modulus: (resulting from changing strain) is the ratio of the shear stress to the shear strain. It follows from the complex relationship similar to the above that:

$G^* = G' + iG''$ where

G* is the complex shear modulus,

G' is the in-phase storage modulus and

G" is the out-of-phase similarly-directed loss modulus; $G^* = \sqrt{(G'^2 + G''^2)}$ Crossover frequency: The frequency where these parameters cross over corresponds to a relaxation time (T) specific for the material.

Tan Delta: tan(5)=G"/G' quantifies the balance between energy loss and storage. As tan(45°)=1, a value for tan(b) greater than unity indicates more "liquid" properties, whereas one lower than unity means more "solid" properties, regardless of the viscosity.

Swelling degree: Extent of swelling in polymers that can be determined via changes in linear dimensions or through volumetric changes. Most polymers swell by solvent (including water) absorption (hydration)

II. Cell Culture

Further, the present invention provides a highly innovative, efficient, quick and reproducible GMP medical devices to produce standardized preparations of platelet-rich-plasma, serum or mononuclear cells from a patient's own blood or bone marrow to be used as a substitute of fetal bovine serum (FBS) for culturing the patient's own cells for regenerative purposes (cell therapy, immunotherapies, neurodegenerative therapies, . . . ).

The present invention provides medical devices for the preparation of autologous platelet rich plasma (PRP), or serum, to be used as cell culture media supplement in replacement of FBS for cellular therapy applications in xenofree conditions.

Cell culture for therapeutic applications should be done in GLP laboratories with certified devices manufactured in GMP conditions. Medical devices of the present invention fulfill these conditions. They allow the rapid preparation, by a single step centrifugation in closed circuit system, of autologous platelet rich plasma or serum. Around 5.5 ml of PRP or 4 ml of serum are obtained from 10 ml of venous blood, thus the number of blood tubes collected can be adapted to reach the desired volume of final product.

Advantageously, the PRP or BMC obtained from the medical devices of the invention may be used in immunotherapy. Immunotherapy is a treatment that uses cells of a patient's immune system to fight diseases such as cancer. Immunotherapy includes treatments that work in different ways. Some boost the body's immune system in a very general way. Others help train the immune system to attack cancer cells specifically. A rapidly emerging immunotherapy approach is called adoptive cell transfer (ACT): collecting and using patients' own immune cells to treat their cancer. There are several types of ACT but the one that is closest to producing a treatment approved by the Food and Drug Administration (FDA) is called CART-cell therapy and brings hope in leukemia and lymphoma therapy. Concerning the methodology, T cells are collected from a patient and then reengineered in a laboratory.

Classically, for isolating mononuclear cells from patient's blood, laboratories use a Ficoll-Paque density gradient media. This methodology is time-consuming, requires several long centrifugations and thus implies a lot of steps were the cells can be damaged.

The specific medical devices of the present invention allow a specific and quick separation of blood mononuclear cells from the patient's blood or bone marrow.

This system allows the preparation of PRP together with the patient's mononuclear white blood cells (MNC).

Stem cells and neurodegenerative diseases is another application field for our innovation.

In this context, a lot of effort is put in regenerative medicine to amplify neuronal stem cells before grafting them into the patients. Defined culture media are available but a lot of questions remained on their in vivo fate and their differentiation. In vitro cultures of these cells are achieved either in neurospheres either in monolayers. Neurospheres display necrosis and spontaneous differentiation problems but they don't need a matrix for the cells to adhere as it is the case for monolayers cultures. For these two drawbacks, devices for cell culture of the present invention may act as a replacement matrix for monolayer culture or as a trophic support for neurospheres tri-dimensional cultures.

The present invention comprises methods and kits intended for rapid, efficient, reliable and standardized preparation of PRP, serum or MNC from a patient's blood or bone marrow.

These devices are also suitable for animal research and therapy.

The devices particularly suitable for cell culture (but still may be used for PC or BMC preparation) have the following common features:
  i) Container, e.g. a tube or syringe. Preferably, the tube is made of borosilicate. Preferably, the tube contains silicone, and is depyrogenated. Preferably, the tube is under vacuum with a stopper.
  ii) A complex Newtonian polymer as additive for cellular separation by gravity. Preferably, the complex Newtonian polymer is a thixotropic gel. Preferably, the thixotropic gel is a large polymer complex with mode of action dependent on the viscosity and density. Preferably, the thixotropic gel is an oligomer, preferably a polyolefin hydrocarbon oligomer or an acrylic resin mixture. The thixotropic gel may be a PEG-Silica Gel.

The thixotropic gel may contain additional substances as, or equivalent thereof, Tris(2-ethylhexyl)benzene-1,2,4-tricarboxylate, silicon dioxide, silane, dichlorodimethyl-reaction products, and/or silica. The thixotropic gel may be further characterized by: unsoluble in water, partially soluble in acetone, and easily soluble in hexane. Further, the thixotropic gel may be characterized by a viscosity of approx. 400 to 700 Pa·s at 15° C., approx. 100 to 250 Pa·s at 25° C., 30 to 100 Pa·s at 45° C. and 10 to 80 Pa·s at 65° C.

For the purpose of cell culture, it has been determined through experiments that the following devices are particularly adapted and providing unexpected and effective results.
  i) A device containing as additive a thixotropic gel with a density of about 1.03 to about 1.05 g/cm3, herein referred to as CC-PRP. Such a device enables the collection of a "pure" PRP. Preferably, the density is of about 1.04 to about 1.05 g/cm3. The device further contains as additive an anticoagulant, preferably sodium citrate, preferably at a concentration of 0.1 M. Preferably, the device contains only these two additives, i.e. the thixotropic gel and the anticoagulant. The thixotropic gel is preferably present as a first layer in the device, e.g. from the closed end of the tube, followed by a second layer consisting of the anticoagulant. Advantageously, such device enables the quick preparation of a PC or BMC except RBCs and polynucleated cells, a PC or BMC without mononuclear white blood cells (MNC), a leukocyte-depleted PRP, PC or BMC.
  ii) A device containing as additive a thixotropic gel with a density of about 1.05 to about 1.095 g/cm3, herein referred to as MC-PRP. Advantageously, such device enables the specific and quick separation of blood mononuclear cells from the patient's blood or bone marrow. Advantageously, such device allows the preparation of PRP, PC or BMC together with the patient's mononuclear white blood cells (MNC), a leukocyte-rich PC, BMC or PRP. Preferably, the density is of about 1.08 to about 1.09 g/cm3, or 1.075 to about 1.09 g/cm3. Most preferably, the density is of about 1.075 to about 1.08 g/cm3. The device further contains as additive an anticoagulant, preferably sodium citrate, preferably at a concentration of 0.1 M. Preferably, the device contains only these two additives, i.e. the thixotropic gel and the anticoagulant. The thixotropic gel is preferably present as a first layer in the device, e.g. from the closed end of the tube, followed by a second layer consisting of the anticoagulant.
  iii) A device containing as additive only a thixotropic gel with a density of about 1.03 to about 1.05 g/cm3, herein referred to as CC-S. Advantageously, such device enables the quick preparation of a thrombin serum.
  iv) A device herein referred to as CC-HA containing as additives:
    a. a thixotropic gel with a density of about 1.03 to about 1.05 g/cm3 or as mentioned under point i) supra,
    b. an anticoagulant, preferably sodium citrate, preferably at a concentration of 0.1 M, and
    c. hyaluronic acid. The hyaluronic acid may non-crosslinked or crosslinked. Preferably, the hyaluronic acid has a molecular weight of about 1500 Kda and at about 1.5% to about 2%, preferably about 2%. The hyaluronic acid may be a crosslinked hyaluronic acid obtained from a method herein described. The molecular weight might range from 500 KDa to 9000 KDa.

Preferably, the device contains only these three additives, i.e. hyaluronic acid, the thixotropic gel and the anticoagulant. The hyaluronic acid is preferably present as a first layer in the device, e.g. from the closed end of the tube, followed by a second layer consisting of the thixotropic gel followed by a third layer consisting of the anticoagulant. Advantageously, such device enables the quick preparation of a PC or BMC in combination with HA. HA may be substituted by another biomaterial.
  v) A device herein referred to as MC-HA containing as additives:
    d. a thixotropic gel with a density of about 1.05 to about 1.09 g/cm3 cm3 or as mentioned under point ii) supra,
    e. an anticoagulant, preferably sodium citrate, preferably at a concentration of 0.1 M, and
    f. hyaluronic acid. The hyaluronic acid may non-crosslinked or crosslinked. Preferably, the hyaluronic acid has a molecular weight of about 1500 Kda and at about 1.5% to about 2%, preferably about 2%. The hyaluronic acid may be a crosslinked hyaluronic acid obtained from a method herein described. The molecular weight might range from 500 KDa to 9000 KDa. Preferably, the device contains only these three additives, i.e. hyaluronic acid, the thixotropic gel and the anticoagulant. The hyaluronic acid is preferably present as a first layer in the device, e.g. from the closed end of the tube, followed by a second layer consisting of the thixotropic gel followed by a third layer consisting of the anticoagulant. Advantageously, such device enables the quick preparation of a PC or BMC in combination with HA. HA may be substituted by another biomaterial.

The anticoagulant may be at a concentration different than 0.1 M, ranging from 0.05 to 0.15M, or preferably from 0.08M to 0.14M, or greater than 0.08M, preferably greater than 0.09M.

The densities provided (may be referred to as gravity) have been measured at a temperature of about 25° C.

The blood preparations issued from these devices can be used alone or in combination: The products, compositions may be used in cell therapy research/therapy.

Combinations of the above devices in cell culture have provided unexpected results with specific advantages:

CC-S+CC-PRP: the autologous thrombin present in the CC-S will re-activate the coagulation in the PRP preparation and allows the formation of a fibrin matrix where the platelets are entrapped.

CC-S+MC-PRP: PRP: the autologous thrombin present in the CC-S will re-activate the coagulation in the PRP preparation and allows the formation of a fibrin matrix where the mononuclear cells and the platelets are entrapped.

CC-PRP+ MC-PRP: To combine the PRP from two different preparations and to maximize its growth effects together with the mononuclear cells specifically isolated thanks to the MC-PRP device.

CC-HA: a single device that allows the combination of PRP and hyaluronic acid in the same preparation with given density appropriate for cell culture.

The invention encompasses platelet lysates obtained from any device or combination thereof.

From the preparations issued from CC-PRP, platelet lysates may be generated by following this protocol: immediately after preparation, freeze the PRP preparations down to at least −20° C. in the without further manipulation. For utilization, thaw human platelet lysate, herein called HPL at 37° C. (water bath) until the ice clots disappear. Do not warm the HPL.

The invention encompasses CC-PRP, MC-PRP, CC-S, CC-HA or any combination thereof obtained from blood or bone marrow.

Combinations of the Technologies

The invention encompasses the following combinations, but not limited to:
CC-PRP+MC-PRP from blood
CC-PRP+MC-PRP from bone marrow
CC-PRP+isolated cells from the same patient (keratinocytes, fibroblasts, bone marrow, periosteum or corneal cells, melanocytes and Langerhans cells, fat cells, muscle cells (myoblasts, satellite cells), osteoblasts, chondrocytes, umbilical cord cells, Schwann cells, tenocytes, mesenchymal stem cells from different origins)
HPL obtained from CC-PRP+MC-PRP from blood
HPL obtained from CC-PRP+MC-PRP from bone marrow
HPL obtained from CC-PRP+isolated cells from the same patient (keratinocytes, fibroblasts, bone marrow, periosteum or corneal cells, melanocytes and Langerhans cells, fat cells, muscle cells (myoblasts, satellite cells), osteoblasts, chondrocytes, umbilical cord cells, Schwann cells, tenocytes, mesenchymal stem cells from different origins)
CC-S+MC-PRP from blood
CC-S+MC-PRP from bone marrow
CC-S+isolated cells from the same patient (keratinocytes, fibroblasts, bone marrow, periosteum or corneal cells, melanocytes and Langerhans cells, fat cells, muscle cells (myoblasts, satellite cells), osteoblasts, chondrocytes, umbilical cord cells, Schwann cells, tenocytes, mesenchymal stem cells from different origins)
CC-S+CC-PRP+MC-PRP from blood
CC-S+CC-PRP+MC-PRP from bone marrow
CC-S+CC-PRP+isolated cells from the same patient (keratinocytes, fibroblasts, bone marrow, periosteum or corneal cells, melanocytes and Langerhans cells, fat cells, muscle cells (myoblasts, satellite cells), osteoblasts, chondrocytes, umbilical cord cells, Schwann cells, tenocytes, mesenchymal stem cells from different origins)
CC-HA+MC-PRP from blood
CC-HA+MC-PRP from bone marrow
CC-HA+isolated cells from the same patient (keratinocytes, fibroblasts, bone marrow, periosteum or corneal cells, melanocytes and Langerhans cells, fat cells, muscle cells (myoblasts, satellite cells), osteoblasts, chondrocytes, umbilical cord cells, Schwann cells, tenocytes, mesenchymal stem cells from different origins)
MC-HA+MC-PRP from blood
MC-HA+MC-PRP from bone marrow
MC-HA+isolated cells from the same patient (keratinocytes, fibroblasts, bone marrow, periosteum or corneal cells, melanocytes and Langerhans cells, fat cells, muscle cells (myoblasts, satellite cells), osteoblasts, chondrocytes, umbilical cord cells, Schwann cells, tenocytes, mesenchymal stem cells from different origins)

Autologous or allogenic PRP may be used for the cell culture.

Further, an albumin gel may be used as support or matrix for the cell culture. The albumin gel may be used in a single layer or dual layers with the cell culture medium in the middle (sandwich like).

Summary of the therapeutic fields where these preparations alone or in combinations can be used:
CELL THERAPY: The use of stem cells, pluripotent cells or reprogramming adult cells in cell therapy for treatment of diseases requires to grow cells in ex vivo conditions. CC-PRP and CC-S are an efficient product to replace FBS in autologous cell therapy. Therapeutical fields include, but are not limited to, regenerative medicine, skin, wound healing, woundcare, tissue regeneration, as a dermal filler in esthetic and plastic surgery procedures, skincare, MusculoSkeletal (MSK), liver regeneration, uro-gynecology and angiogenesis.
TISSUE ENGINEERING: the regeneration of damaged tissue requires the creation of a scaffold in which the patient's own cells can proliferate and maintain the biological function of each tissue type. The Cell culture products (CC-PRP combined with CC-S) form a three-dimensional fibrin scaffold rich in growth factors supporting cell proliferation and tissue regeneration.
IMMUNOTHERAPY: The use of lymphocytes to fight against cancer requires that they are taken from the patient's own body. The lymphocytes are then activated ex vivo, before being reinjected into the patient. The MC-PRP allows for the quick and easy isolation of lymphocytes to be used in immunotherapy.

Advantageously, the devices for cell culture of the invention allow a specific and quick separation of blood mononuclear cells from the patient's blood or bone marrow: the Cell culture tube technology.

The invention provides also medical devices (may be referred to as kits) which may comprise the following components:
i) For CC-PRP:
  kit is 6×CC-PRP tubes (10 ml)
  Tube contents
    Separator Gel
    Sodium Citrate (Anticoagulant)
ii) For MC-PRP:
  6×MC-PRP tubes (10 ml)
iii) For CC-S:
  kit comprises 6×CC-S tubes (10 ml)
Kits may comprise the following additional material:
Blood collection accessory set
Horizontal head (swinging bucket) or a fixed 45° angle rotor centrifuge.

Advantageously, the following results are obtained with the devices of the invention:
CC-PRP: platelet recovery: 80%, Platelet concentration factor: 1.6×
MC-PRP: platelet recovery: 95%, Platelet concentration factor: 1.7× with recovery of mononuclear cells.

Advantageously, the devices of the invention do not induce an inflammatory reaction.

Advantageously with CC-S is that it brings nutritive factors and brings as well autologous thrombin to make a platelet gel. Combination with CC-S enables surprisingly a matrix for 3D cultures of the cells or a matrix to coat the dishes for 2D cultures, with improvement of cell attachment and cell type differentiation.

The devices of the invention are particularly suitable for 3D culture with formation e.g. of matrixes, supports for culture or scaffold material.

The devices may be substitute and/or combine with synthetic copolymers, ceramic and glass-ceramics, bioartificial blends of natural and synthetic materials.

Examples are proposed so as to illustrate the invention but are in no way limiting of the invention.

EXAMPLES

Example 1—Hyaluronic Acid

Using the methods described herein, cross-linked Hyaluronic Acid (herein also referred to as XLHA) has been synthesized starting from bacteria fermented HA to obtain a product having the following specifications:
1. 2% maximum content of HA
2. 20% maximum degree of cross-linking
3. 60 Pa·s as highest value of complex viscosity
4. 2 ppm maximum concentration of residual BDDE
5. Easily injectable with cannula 22G1/2 or 27G1/2

Several experiments have been conducted in order to get hyaluronic acid with little BDDE contamination. Surprisingly, the method of the invention provide little BDDE contamination even though it involves fewer steps, much faster and cost effective than previous known methods.

Advantageously, crosslinked HA with the following specifications were also obtained:
Cross-linked hyaluronic acid from HA obtained by fermentation.
Cross-linking percentage: 10-50%
Cross-linking agents: BDDE in basic conditions
Cross-linked HA reabsorption time: 3-4 months (range of absorbable product=3-6 months)
HA concentration: 2%
BDDE residue: <2 ppm
Homogeneous gel
Viscoelastic gel
Easily injectable with cannula 22G1/2 or 27G1/2
Complex Viscosity: maximum 60 Pa·s for syringes
Elasticity: max 50%
Free of "glitter" of local over-cross-linking
Density of crosslinked HA should be lower than separator gel's in order to migrate over the latter after centrifugation
Usable in tubes for the preparation of PRP+HA or BMC+HA (HA should be easy to mix with PRP or BMC) and in syringes 2 ml and 35 ml.
Biocompatible according to ISO 10993
Sterilisation by steam
Non-pyrogenic
Manufacturing process reproducible and stable HA fibers and powder have both been used for the production of non-XLHA and their different hydration quality.

For each batch produced the quantity of residual BDDE has been determined while the analysis for the calculation of the percentage of cross-linking have been requested.

Two different synthesis implying two different quantities of BDDE hence two different final % of cross linked have been performed. Rotation/revolution mixing as well as pouch are used for the preparation of the XL products.

A continuous one-pot method, suitable for process automatization, to produce XLHA is herein disclosed. Advantageously, the method enables tunable viscosity. Advantageously, the molecular weight is chosen at the beginning of the process according to the final applications, same for the concentration that needs to reach a certain final value so that all the process is planned in advanced in order to reach the wanted value.

Several batches have been produced using this process. As shown in FIG. 1, the first phase is the hydration of the fibers/powder:
1) polymer fibers/powder will be transferred in a reactor that then will be closed. Solvent will be then added while filtered (220 μm), under stirring through a feeding vessel. As alternative, with the reactor already closed, powder will be added using the solid port then solvent as described above.
2) After homogenization of the mixture a basic solution containing a crosslinking agent will be added, the pH measured
3) The temperature is then raised up to 50° C. After 2 hours, the mixture will be taken back to room temperature.

4) A neutralization step is performed by addition of an acid. A solution of HCl in PBS will be added though a feeding vessel while filtered. The pH will be checked to assure that the physiological conditions have been reached. Neutral pH will already reduce the reactivity of HA as the hydroxyl groups will be less protonated hence less reactive.
5) The mixture will be kept stirring at 4 C° overnight and the pH checked again at the end of this phase. The low temperature will also reduce the reactivity of the system and allow complete homogenization without further cross-linking.
6) Finally, the mixture will be taken back to room temperature and a certain quantity of uncrosslinked HA will be added to obtain the viscosity necessary to hold the separating gel and allow the mixture with PRP. The polymer will be added through a feeding vessel and left stirring until complete homogenization.
7) The gel will be at this point collected while filtered (280 μm)

See FIG. 1.

In this way, the entire synthetic process will be performed in a closed environment without exposing the gel to possible contamination, the continuous process will allow better homogenizations of the synthetic mixture during the whole process, the manipulations will be reduced to zero hence the time consistently shorter.

The final phase of the process is the purification by dialysis. This method is largely used because allows to separate molecules of different size and both soluble in the same solvent. During purification, the unreacted BDDE will be eliminated by passing through the dialysis membrane while water will enter allowing further swelling of the polymer. The final concentration will be reached and residual BDDE will be already present in traces and will be further reduced after sterilization.

In fact, quantity of residual BDDE has been tested for all the batches produced and purified with different membranes at different temperatures and further sterilized or degassed.

The obtained XLHA may advantageously be used for the production of a medical device for the preparation of A-PRP in combination with hyaluronic acid.

Below is one embodiment of the method of preparing a cross-linked HA according to the invention:

| Method of the present invention | Comments |
| --- | --- |
| 18 g of hyaluronic acid (MW: $1.5 \times 10^6$ Da) is diluted in 192 ml of a 1% NaOH solution (ethanol-containing aqueous alkaline solution) The whole is homogenized in a mixture until a transparent solution is obtained. | Concentration 9% |
| The crosslinking reaction is triggered by the addition of 110 μl of 1,4-butanediol diglycidal ether (BDDE) in basic PBS and the whole is mixed for 2 h at 50° C. | 2 hours synthesis |
| The pH is readjusted to physiological pH with 0.08 HCl and the volume is adjusted to obtain a 2.15% solution (w/w) | 12 hours but actually until homogenization Advantage: the concentration of HA is already the final one so that we can tune the viscosity according to necessity |
| Then a supplemental polymer (MW: $1.5 \times 10^6$ Da). with the same concentration whilst adjusting the viscosity. | Until homogenization The viscosity can be tuned to allow mixing with PRP and passage through a 27 G needle |
| The whole is homogenized. So as to purify the obtained gel, it is then dialyzed for 24 h (regenerated cellulose, limit of separation: MW: 25 kDa). This will allow a further swelling This gel has a total hyaluronic acid content of 2% by weight. Gel is finally sterilized by vapor | 50 and 25 have be tried but no differences have been observed. 12-14 might be good |

Figure 2:
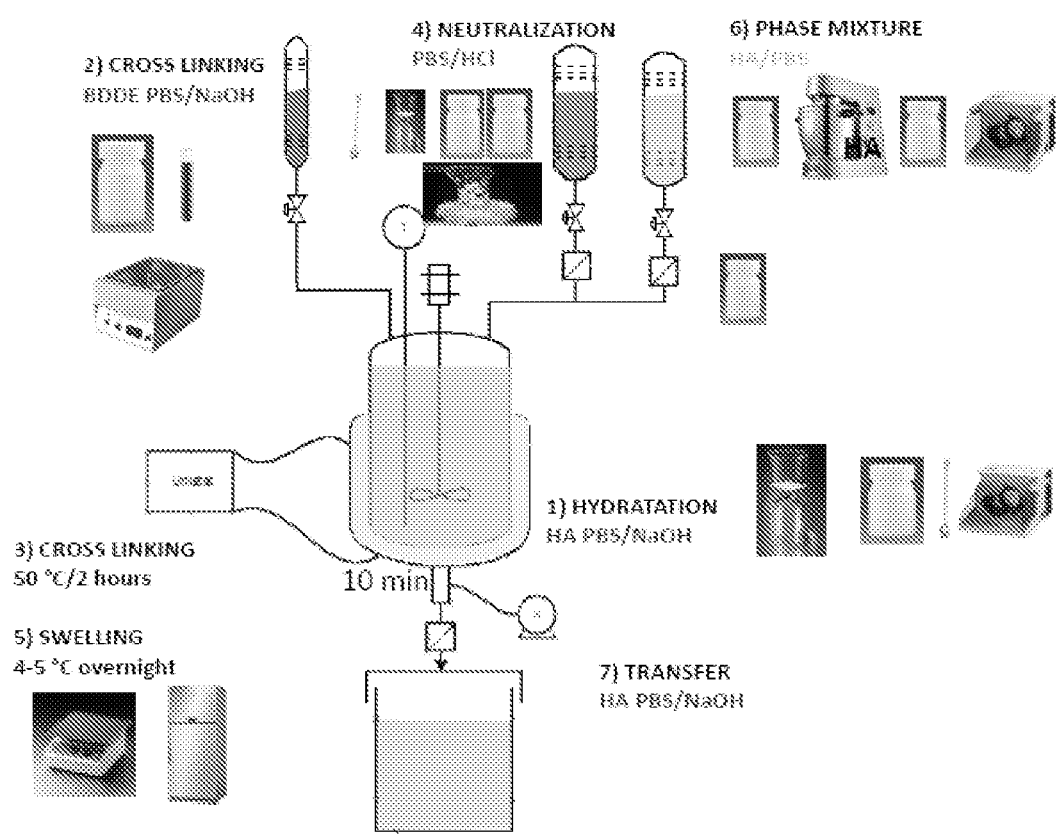

Material used for the preparation of cross-linked HA according to the invention is shown in FIG. 2, in summary:

| SYNTHESIS | EQUIPMENT |
|---|---|
| Reagents (type and quantity) | Reactor |
| Solvent | Stirrer |
| Temperature | Turbula |
| pH | Stirrer |
| Time (reaction) | Filter |
| Light | Cryostat |

In a preferred embodiment, the invention uses a "one pot" system instead of turbula. Further, an anchor-stirrer device or vessel is preferably used instead of impellers. An anchor-stirrer vessel results in improved properties of the HA compositions. It has been surprisingly found that the "one pot" solution provides the following numerous advantages when used in the preparation of hyaluronic acid:

| | | TURBULA | ONE POT |
|---|---|---|---|
| 1 | Hydratation | 1 h 30 min/2 manipulations | 1 h 30 min/0 manipulations |
| 2 | Cross linking | 2 h/2 manipulations | 2 b/0 manipulations |
| 3 | Neutralisation/ Swelling | 60-68 hours/3 manipulations XLHA in HCl | 12-20 hours/0 manipulations HCl in XLHA |
| 4 | Phase mixture | 14 hours/1 manipulation XLHA in HA 3.5 days/8 manipulations | 4 hours/0 manipulations HA in XLHA 1.5 days/0 manipulations |

NOTE: time and manipulation considered refer to the profess per se excluding the solutions' preparation and the time for heating and cooling down that for simplicity are considered equal

| TUBULA | ONE POT |
|---|---|
| Good mixing | Good mixing |
| Stop at every step | Continue process |
| Low control over the cross-linking reaction (static on original synthesis up to 2% crosslinking in patents) | Easier scale up |

| TUBULA | ONE POT |
|---|---|
| All pieces are autoclavable | All pieces are detachable and autoclavable Reactor to be cleaned with validate cleaning procedure (resistant to acids, bases and temperatures) |

Example 1A-Synthesis of Crosslinked (XL) Hyaluronic Acid (HA), Starting from Non-Crosslinked HA and BDDE as Crosslinking Agent Subject: Synthesis and Development of Regen Matrix™ Products, as a successor to the Cellular Matrix™ (HA+PRP) Products. Development of Regen Matrix™ tubes (and/or syringes) containing XLHA synthetized in a ONE POT reaction, for the preparation of [PRP+XLHA] mixtures (e.g. solutions), for use in skin care and joint preservation.

Example 1A: Summary

Cross-linked hyaluronic acid (XLHA) has been synthesized starting from bacteria-fermented hyaluronic acid (HA) (in this specific synthesis, HA is in polyanionic form and is present as a sodium salt), to obtain a product having particular specifications, as follows:

2% maximum content of HA (see e.g. WO 2004/014399 A1, "Process for preparing a sterile high molecular weight hyaluronic acid formulation");

20% maximum degree of cross-linking (see e.g. Jeon, O., et al., *Carbohydrate Polymers*, 70, (2007), 251-257);

60 Pa·s as highest value of complex viscosity (see e.g. http://www.rheosense.com/applications/viscosity/ drug-injectability, and/or see e.g. Nicholls, M. et al, Clinical Medicine Insights: Arthritis and Musculoskeletal Disorders, (2018), 11, 1-5);

2 ppm maximum concentration of residual BDDE (see e.g. De Boulle, K., et al, Dermatol. Surg., 2013; 39: 1758-1766);

Easily injectable with a cannula (needle) of type/gauge 22G1/2 or 27G1/2.

The parameters chosen for the formulation are based on the Cellular Matrix™ tubes already produced by Regen-Lab™ on the data already reported in literature and on the production of non-XLHA already performed within Regen-lab™.

In this Example 1A, we report the activities performed during research & development, concerning the literature consulted, the synthetic apparatus proposed and the synthetic experiments and/or tests planned and performed.

HA fibers and HA powder have both been used as starting materials because they have already been chosen by Regen Lab™ for the production of non-XL HA and their different hydration quality. From the point of view of the synthesis it is believed that there is no or little difference between HA fibers and HA powder (except that HA powder preferably requires a longer hydration time), because it is believed that the reactivity and the ratio between reagents does not change if the M.W. is substantially in the same range.

While proceeding in the development, HA fibers have been more frequently used for the synthesis due to their availability. For the purpose of the synthesis it has been determined that the HA used should not influence the results as soon as the molecular weight falls substantially in the same range (preferably, approximately 1500 KDa) and the hydration phase is completed.

For each batch of XL HA produced, the quantity (concentration) of residual BDDE in the XL HA product can be or has been determined. Also, an analysis enabling the calculation of the percentage of cross-linking in the XL HA product can be or has been done.

Example 1A: Introduction

Hyaluronic acid ("HA", also known as hyaluronan) is a saccharide (specifically a glycosaminoglycan) comprising repeating (1, 2, 3 or more) disaccharide units of [D-glucuronic acid and N-acetyl-D-glucosamine](see e.g. Structure 1A1 below).

At physiological pH, HA is normally present as a polyanionic polymer (e.g. oligomer) in which some or all (typically most or all, more typically substantially all) of the carboxylic acid (—COOH) groups, within the D-glucuronic acid moiety(ies), are deprotonated (i.e. are present as carboxylate groups). Preferably and/or usually, e.g. under physiological pH and/or conditions, the HA is at least partly (typically mostly) present as a or the sodium salt, typically a or the sodium salt of a or the carboxylate/polycarboxylate form(s) of HA. This preferred and/or common anionic/polyanionic (e.g. carboxylate/polycarboxylate) form of HA, and its sodium salt, is/are represented as the disaccharide structure(s) shown in Structure 1A1 below (reproduced from Ahmet Tezel & Glenn H. Fredrickson, *Journal of Cosmetic and Laser Therapy*, 2008; 10: 35-42).

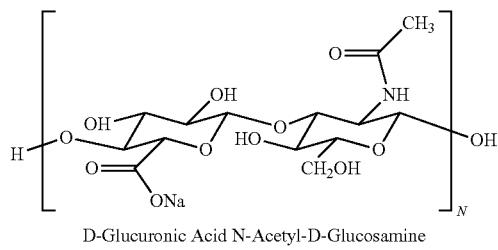

D-Glucuronic Acid N-Acetyl-D-Glucosamine

Structure 1A1: Typical structure of the hyaluronic acid (HA) monomer (N=1) and/or of the HA polymer (N>1) (reproduced from Ahmet Tezel & Glenn H. Fredrickson, *Journal of Cosmetic and Laser Therapy*, 2008; 10: 35-42). "Polymer" as defined herein includes within its scope "oligomer"; and independently "poly-" includes within its scope "oligo-"; unless the context clearly indicates otherwise. HA polymers are preferred (N>1, preferably N=2 to 25000 or more); HA monomers are less preferred. In the chemical structure shown above, the HA is shown in the form of the sodium salt of the deprotonated carboxylate or polycarboxylate form of HA, but this is not the only structure covered by the term "HA".

"Hyaluronic acid" ("HA") as defined herein includes a or the carboxylic acid form(s) and/or polycarboxylic acid form(s) of the above-shown Structure 1A1 and, independently, includes any salt form(s), in particular any anionic (preferably polyanionic) salt form(s), of the above-shown Structure 1A1 (in particular any pharmaceutically-acceptable metal and/or ammonium and/or organoammonium salt(s) of the above-shown Structure 1A1, preferably any pharmaceutically-acceptable alkali metal salt(s) and/or alkaline earth metal salt(s) of the above-shown Structure 1A1, more preferably any lithium, sodium, potassium, calcium and/or magnesium salt(s) of the above-shown Structure 1A1).

Preferably, "hyaluronic acid" ("HA") as defined herein includes a or the carboxylic acid form(s) and/or polycarboxylic acid form(s) of the above-shown Structure 1A1, and, independently, includes any salt(s) (e.g. any of those salt(s) listed above, more preferably any lithium, sodium, potassium, calcium and/or magnesium salt(s)) of a or the carboxylate form(s) and/or polycarboxylate form(s) and/or polyanionic form(s) of the above-shown Structure 1A1.

In an analogous manner, as defined herein, "cross-linked hyaluronic acid" ("XLHA" or "XL HA") includes a or the carboxylic acid form(s) and/or polycarboxylic acid form(s) of the XLHA structure e.g. as defined in general terms herein (hereinbefore and/or hereinafter, e.g. see Structures 1A4(A) and/or 1A4(B) herein) and, independently, includes any any salt form(s), in particular any anionic (preferably polyanionic) salt form(s), of the XLHA structure e.g. as defined in general terms herein (e.g. any of those salt(s) listed above for HA).

Preferably, "XLHA" as defined herein includes a or the carboxylic acid form(s) and/or polycarboxylic acid form(s) of the XLHA structure e.g. as defined in general terms herein (e.g. see Structures 1A4(A) and/or 1A4(B) herein), and, independently, includes any salt(s) (in particular any pharmaceutically-acceptable metal and/or ammonium and/or organoammonium salt(s), preferably any pharmaceutically-acceptable alkali metal salt(s) and/or alkaline earth metal salt(s), more preferably any lithium, sodium, potassium, calcium and/or magnesium salt(s)) of a or the carboxylate form(s) and/or polycarboxylate form(s) and/or polyanionic form(s) of the XLHA structure e.g. as defined in general terms herein (e.g. see Structures 1A4(A) and/or 1A4(B) herein).

In vivo, HA is produced, and hence is present, in various part of the human body such as skin, synovial fluid of joints vitreous fluid of the eye, and scaffolding within cartilage.

HA is a polyanionic polymer at physiological pH and therefore highly charged. It is exactly for this reason that it is very soluble and it can extensively bind water (see e.g. Kablik, J., et al., *Dermatol. Surg.*, 2009; 35: 302-312). The average amount of HA present, in a human being of 70 kg body weight, is about 15 g, one third of which is degraded and/or synthesized every day. The degradation process is very important and is performed by a class of enzymes called Hyalurohydrase, in particular HYAL 1 and/or HYAL 2, which are respectively attached to the cell membranes and to the lysosomes. Firstly, HYAL 2 breaks polymers of normally over 1 MDa to a 20 KDa fragment, then HYAL 1 cleaves the fragment(s) into tetrasaccharides, which are further hydrolyzed to monomers before being eliminated (see e.g. Jeon, O., et al., *Carbohydrate Polymers*, 70, (2007), 251-257).

When HA is chemically modified to obtain a polymer, whose chains are connected between themselves (interconnected), then this chemically modified polymer is named "cross-linked hyaluronic acid" (XLHA) (see e.g. Ahmed, E. M., *Journal of Advanced Research*, (2015), 6, 105-121).i XLHA is a hydrogel (hydrophilic gel) with an amorphous network, which can be crosslinked using a large number of agents. The most used for biomedical applications is the 1,4-butanediol diglycidyl ether (BDDE) thanks to its less toxic nature (see e.g. Jeon, O., et al., *Carbohydrate Poly-* mers, 70, (2007), 251-257). The structure of BDDE is shown below; most importantly, the structure contains two epoxide groups, one at each end of the linear organic molecule:

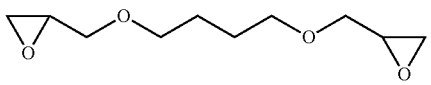

Structure of 1,4-butanediol diglycidyl ether (BDDE)

A preferred generalized structure of a di-epoxide cross-linking agent (crosslinker), preferably suitable for use in cross-linking HA, is shown below:

[Structure 1A3]

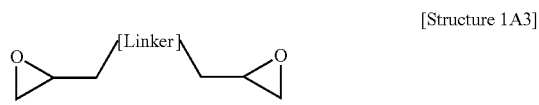

In the above generalized di-epoxide crosslinking agent (crosslinker) [Structure 1A3], the illustrated linker, shown as "[linker]", is preferably an organic linker moiety and/or preferably is of a length and/or structure suitable for cross-linking HA polymers e.g. suitable for cross-linking HA polymers at their —OH groups. Preferably, the [linker] comprises a chain of 2 to 20 atoms (preferably of 3 to 12 atoms e.g. 4 to 8 atoms e.g. 6 atoms) in length. (The chain is preferably linear, but optionally it can be branched.) More preferably, the [linker] comprises a chain (preferably linear chain) of 2 to 20 (or 3 to 12, or 4 to 8, e.g. 6) atoms in length wherein the chain atoms comprise chain carbon atoms (e.g. as —$CH_2$— or —CHMe- or —$CMe_2$— groups (Me=methyl)); and wherein optionally the chain atoms also comprise 1, 2, 3 or 4 chain oxygen, chain sulfur and/or chain nitrogen atoms (preferably the chain atoms also comprise 1, 2, 3 or 4, preferably 1 or 2, chain oxygen atoms).

In general, epoxides are alkylating agents (and are electrophiles) which can react with nucleophilic groups such as hydroxyl (—OH, alcohol) groups, especially under suitable alkylating conditions.

Depending on the pH conditions, the HA molecules display different behavior. In general, BDDE prefers to react with the alcohol groups of HA rather than with the carboxylic acid groups of HA (see e.g. L. Kenne et al., *Carbohydrate Polymers*, 91, (2013), 410-418), depending on the pH, as follows:

When HA is subjected to high pH values, specifically pH values (preferably about pH>13) which are above (preferably 1 or more, or 2 or more, or 2.5 or more or 3 or more, pH units above) the pKa value of the hydroxyl groups of HA (whose pKa's are approximately 10), the latter are almost all deprotonated and thus are more nucleophilic than the deprotonated carboxylate groups of HA which also exist at such pHs.

Therefore, at such high pH values, the epoxide groups of the cross-linking agent, preferably of BDDE, react preferentially with the hydroxyl groups of HA to form ether bonds.

When the pH is lower than the pKa value of the hydroxyl group, a smaller quantity or percentage of hydroxyl groups of HA is or are deprotonated, and the anionic carboxylate groups of HA are the more predominant anion on HA. These conditions promote ester bond formation, by reaction of the epoxide groups of the cross-linking agent with (mostly) anionic carboxylate groups of the HA.

After the crosslinking reaction, BDDE can be present in different chemical states. As illustrated in Structural Scheme 1A2 hereinbelow, especially at high pH, the cross-linking agent (here, BDDE) preferentially reacts with the primary alcohol groups (i.e. —$CH_2$—OH) in the HA backbone. The different states in which BDDE can be present in the final cross-linked HA product are summarized below (see also, e.g., Jeon, O., et al., *Carbohydrate Polymers*, 70, (2007), 251-257):

Fully reacted crosslinker: a BDDE molecule that has reacted with HA on both ends yielding disubstituted BDPE (structure A in Structural Scheme 1A2) (see e.g. Jeon, O., et al., *Carbohydrate Polymers*, 70, (2007), 251-257 and/or Kablik, J., et al., *Dermatol. Surg.*, 2009; 35:302-312).

Pendant crosslinker: a BDDE molecule that has reacted with HA on one end only, i.e. only one epoxide group has reacted with (alkylated) one HA chain.

The second epoxide group, at the other end of the BDDE, generally reacts with water or hydroxide. In this way, mono-linked BDPE is formed (structure B in Structural Scheme 1A2) (see e.g. Jeon, O., et al., *Carbohydrate Polymers*, 70, (2007), 251-257 and/or Kablik, J., et al., *Dermatol. Surg.*, 2009; 35: 302-312).

Deactivated crosslinker: a BDDE molecule that has reacted at both ends with water or hydroxide forming free BDPE (fully hydrolyzed BDDE) (structure C in Structural Scheme 1A2) (see e.g. Jeon, O., et al., *Carbohydrate Polymers*, 70, (2007), 251-257 and/or Kablik, J., et al., *Dermatol. Surg.*, 2009; 35: 302-312).

Residual crosslinker: a BDDE molecule that has not reacted with HA or water or hydroxide (structure D in Structural Scheme 1A2). The risk linked to the presence of residual crosslinker is almost completely eliminated through purification of the crosslinked product (see e.g. Kablik, J., et al., *Dermatol. Surg.*, 2009; 35: 302-312).

Purification of the so-obtained XLHA is an important point in the entire process, because it is strongly preferable that the residual quantity of unreacted crosslinker (e.g. unreacted BDDE) is lower than 2 ppm (i.e. or e.g. is lower than 2 mg per L of aqueous medium e.g. per L of aqueous gel) in the final (e.g. purified) XLHA product.

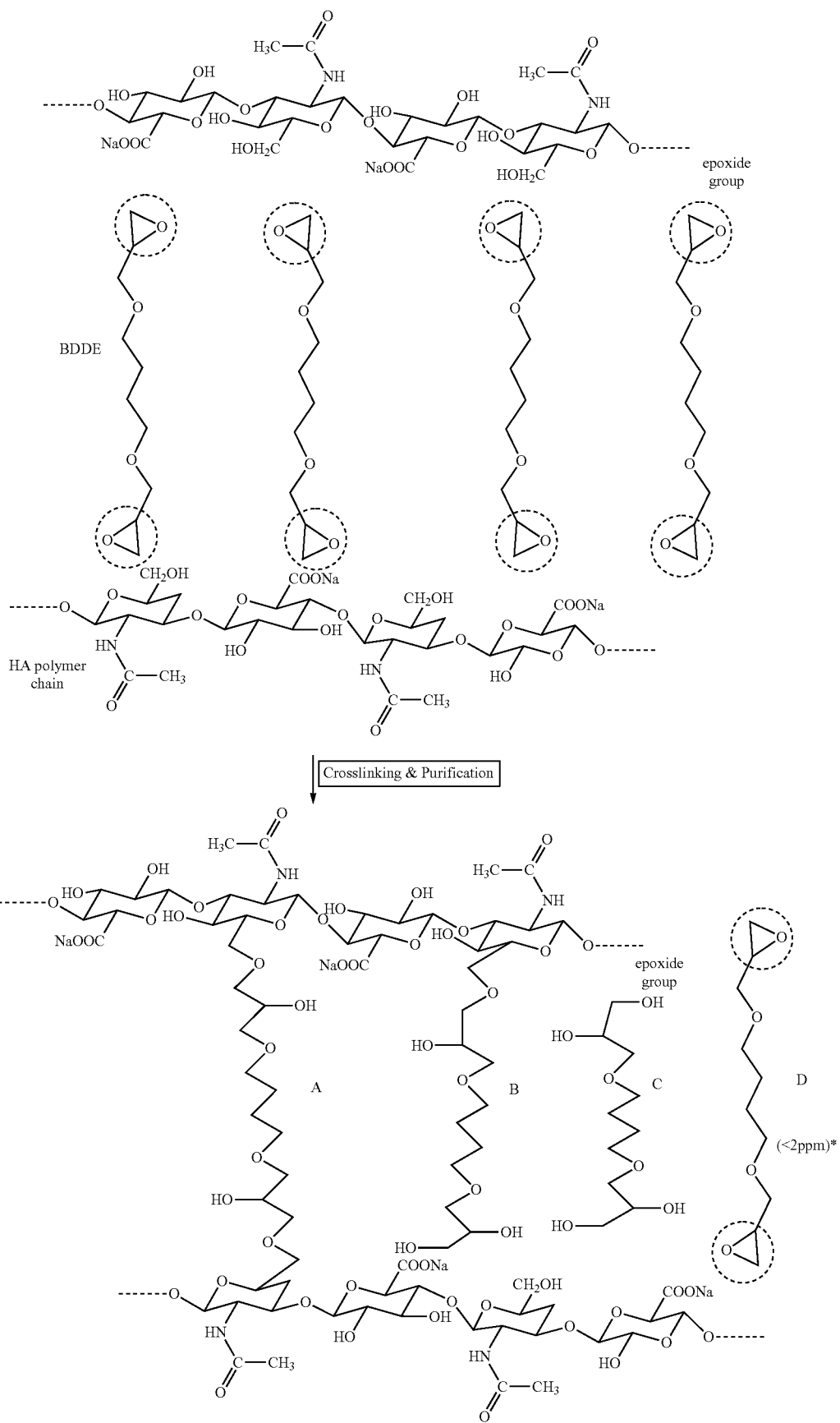

Structural Scheme 1A2: Schematic showing the crosslinking reaction of hyaluronic acid (HA) chains with the crosslinking agent BDDE. In Structural Scheme 1A2 above, the HA starting material is shown in the form of a or the sodium salt(s) of a or the polycarboxylate (deprotonated and/or polyanionic) form(s) of HA; however, any form of HA, e.g. as defined herein, can be used; and so any form(s) of crosslinked HA can be formed. Also, different (non-BDDE) di-epoxide crosslinking agents can be used instead of and/or as well as BDDE. Regarding the products A, B, C and D formed during the crosslinking reaction of HA with the di-epoxide crosslinking agent (preferably BDDE), since the sum of all four products (A to D) derived from the di-epoxide (preferably BDDE) is <5 mg/mL, or <5,000 ppm, the trace levels of the native form D of di-epoxide (preferably BDDE) (the trace levels being <2 ppm; i.e. or e.g. <2 mg per L of aqueous medium e.g. aqueous gel) represent a very small fraction of the sum of the products (A to D) of the crosslinking reaction.

One preferable generalized structure of cross-linked HA, which is capable of being prepared in a reaction wherein a generalized di-epoxide cross-linker (crosslinking agent)

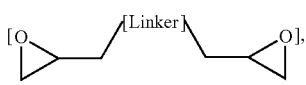

which is Structure 1A3, wherein the "[linker]" is preferably as defined herein, is used to crosslink HA polymer, to produce the generalized structure of cross-linked HA (below), is as follows:

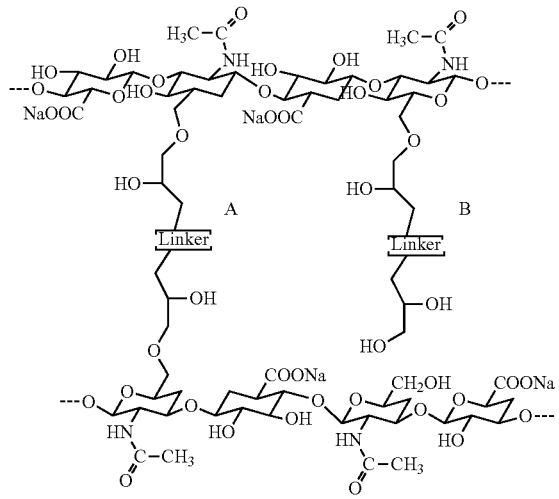

Structures 1A4(A) and 1A4(B): Preferable generalized structure(s) of cross-linked HA. Partial Structure 1A4(A), on the left, illustrates in general terms a generalized crosslinking chain (A), which is formed by reaction of generalized di-epoxide cross-linker (crosslinking agent) (Structure 1A3) with the —OH groups of two HA polymer chains. Partial Structure 1A4(B), on the right, illustrates in general terms a generalized pendant chain or group (B), which is attached to one HA or XLHA polymer chain only, which is formed by i) reaction of one epoxide group of a or the generalized di-epoxide crosslinking agent (Structure 1A3) with the —OH group of 2n HA polymer chain, plus ii) hydrolysis (eg by water or hydroxide) of the second epoxide group of the mono-HA-linked linker.

For convenience, Partial Structures 1A4(A) and 1A4(B) are shown to be both present at adjacent positions on two crosslinked HA chains—however, this is for illustrative purposes only, and the structure(s) of XLHA can include 1A4(A) only, or 1A4(B) only, or both, and the relative distance between A and B type linkers/groups, and the relative proportion of A and B type linkers/groups, and the % crosslinking and the % of pendant groups, are all variable.

In the above generalized Structures 1A4(A) and 1A4(B) of cross-linked HA, the illustrated linker, shown as "[linker]", is preferably an organic linker moiety and/or preferably is of a length and/or structure suitable for cross-linking HA polymers e.g. suitable for cross-linking HA polymers at their —OH groups. Preferably, the [linker] comprises a chain of 2 to 20 atoms (preferably of 3 to 12 atoms e.g. 4 to 8 atoms e.g. 6 atoms) in length. (The chain is preferably linear, but optionally it can be branched.) More preferably, the [linker] comprises a chain (preferably linear chain) of 2 to 20 (or 3 to 12, or 4 to 8, e.g. 6) atoms in length wherein the chain atoms comprise chain carbon atoms (e.g. as —$CH_2$— or —CHMe- or —$CMe_2$— groups (Me=methyl)); and wherein optionally the chain atoms also comprise 1, 2, 3 or 4 chain oxygen, chain sulfur and/or chain nitrogen atoms (preferably the chain atoms also comprise 1, 2, 3 or 4, preferably 1 or 2, chain oxygen atoms).

(Note: The exact form of XLHA, and/or the salt form (if any) of XLHA, and/or the positions (within the XLHA polymer) and/or the proportions or percentages of any crosslinking chains (e.g. in Structure 1A4(A) above) and optionally any pendant chains (e.g. in Structure 1A4(B) above), can be varied considerably from what is shown in the structure above, which is an example structure only for illustrative purposes. The pendant chains (e.g. of the type shown in Structure 1A4(B) above) are optional—they may or may not be present in XLHA. The crosslinking chains (preferably of the type shown in Structure 1A4(A) above) are present in crosslinked hyaluronic acid (XLHA). The XLHA is shown above in the polyanionic (polycarboxylate) form, and as the sodium salt; however, in the present invention, any form (e.g. polyanionic or acidic or otherwise) of XLHA and/or any salt form of XLHA is possible.

Example 1A: Production in Industry

XLHA has been produced by a number of companies with different processes. The XLHA gels obtained are mostly used in the preparation of syringes, for use in dermatological treatments. In general, depending on the quantity of crosslinker (preferably BDDE) used and/or the physical parameter(s) adopted for the synthesis, the percentage of crosslinking can be modulated and gels with a variety of viscoelastic properties and residence times can be produced.

Several articles and patent applications have been published describing different methods used for the synthesis of XLHA. The first synthesis of XLHA using an epoxide crosslinker was reported by Laurent, Hellsing, and Gelotte in 1964 (Laurent, T., Hellsing, K., & Gelotte, B., "Crosslinked gels of hyaluronic acid", Acta Chemica Scandinavia, (1964), 18(1), 274-275). The first patent application disclosing the use of BDDE as a cross-linker, in the name of Malson and Lindqvist, was published in 1986 (WO 86/00079, Malson, T., & Lindqvist, B., "Gels of crosslinked hyaluronic acid for use as a vitreous humor substitute"). Since then, the syntheses of XLHA have been adapted by others according to their needs, and new synthetic methods have been developed as the technology and the equipment have developed.

For example, Merz-Anteis produces a series of products based on cohesive XLHA synthesized by a method disclosed in a 2005 patent application, where the cross-linking is carried out in an oxygen-free atmosphere (WO 2005/085329, Hermitte, L. and Benoit, O., "Biocompatible cross-linked gel").

Later, the following three patent applications were published in the name of Teoxan:
  a) a patent application which describes the synthesis of a XLHA in which an extrusion step is implied (WO 2012/077054 A1; Meunier, S. and Bourdon, F.; "Process of preparing a cross linked gel");
  b) a second patent application which introduces the use of an anesthetic in the formulation (WO 2015/015407 A1; Meunier, S. and Bourdon, F.; "Composition comprising hyaluronic acid and mepivacaine"); and
  c) a third patent application disclosing a new method using a deformable pouch for homogenizing the gel (WO 2010/131175 A1; Bourdon, F.; "Process for preparing a crosslinked gel").

Finally, Shiseido disclosed a method where a rotation/revolution mixer is used (US 2011/0034684 A1, Yokokawa, Y., Oka, T., Mori, Y. and Ueno, N.; "Process For Preparing Crosslinked Hyaluronic Acid Gel").

In general, most or all of the previously-disclosed methods of synthesizing a or the cross-linked polymer (specifically, XLHA) have some steps in common such as:
  1. Initial hydration step during which the polymer (specifically, HA), in the physical form of a powder or fibers, is solubilized into a buffer media, typically a buffered aqueous media;
  2. A crosslinking step where a cross-linking agent is added and the reaction is carried out for a certain time at a certain temperature at specific pH conditions;
  3. A phase of neutralization, which is necessary in the typical case that the application (use) environment for the final XLHA product is the human body; and
  4. A last phase of purification to eliminate and/or to reduce (preferably to eliminate and/or to reduce by 50% or more or 70% or more or 90% or more or 95% or more or 99% or more) the amount (i.e. number of moles or number of molecules) of the unreacted crosslinker.

In some of the previously-disclosed methods to make XLHA, some intermediate phases are included such as swelling and/or addition of another polymer or anesthetic, e.g. depending on the final formulation required and the properties desired (with respect to viscosity, residence time, and/or intended use, et al.)

Example 1A: Synthesis of XLHA for Use in the Development of New Products

Regen Lab™ has been known, in the field(s) of medical devices and/or pharmaceutical compositions, for the production of products (pharmaceutical compositions) containing hyaluronic acid (HA), especially for use in treatments and/or prophylaxes in the fields of dermatology and/or orthopedics, preferably in humans. In particular, Cellular Matrix™ (for which see e.g. WO 2013/061309 A2, Turzi, A., "New a-prp medical device & tissue engineering composition, manufacturing machines and process") is a product which has been largely used for the contribution given by the two active products contained within it, that is PRP (platelet rich plasma) and hyaluronic acid (HA), to skin rejuvenation (e.g. see Lana J F S D, et al., *J. Stem Cells Regen Med.*, 2016; 12(2); and/or Ulusal, B. G., *Journal of Cosmetic Dermatology*, 2017; 16(1): 112-119).

From here the idea arose, according to and/or leading to the present invention(s), to attempt to develop a variant of the Cellular Matrix™ product, in which the non-crosslinked (non-XL) HA is substituted by a XL HA (Regen Matrix™)

Any such new XLHA and/or XLHA-containing product, in particular according to the present invention(s), would preferably be:
  (a) for use in the preparation of an injectable pharmaceutical composition, for use in the treatment and/or prophylaxis of articular pain symptoms and/or joint mobility improvement and/or another joint-related disorder (preferably in a human), preferably by administration by injection, more preferably by injection into a joint in need of such treatment and/or prophylaxis;
  and/or
  (b) for use in the preparation of an injectable pharmaceutical composition, for administration by injection into mid-dermis to deep dermis (preferably of a human); preferably:
  (b1) for use in the correction and/or modification of atrophic scars (preferably atrophic scars of traumatic and/or post-operative origin), preferably in a human; and/or
  (b2) for use in the treatment and/or prophylaxis of skin dehydration, preferably in a human; and/or
  (b3) for use in the correction and/or modification of facial wrinkles (preferably moderate to severe facial wrinkles) and/or of folds anatomy, such as nasolabial folds, preferably in a human.

An important point, for the properties and/or preparation of such a pharmaceutical composition (and/or medical device), in particular according to the present invention(s), is the mixture between (i) PRP and (ii) either HA (for the known Cellular Matrix™ product) or more preferably XLHA (for the present invention(s)).

In particular according to the present invention(s), it is strongly preferable that the gel (preferably a XLHA-gel and/or a XLHA-containing gel) has a viscosity which allows an effective and/or homogeneous mixture, of (i) the PRP and (ii) the gel and/or the XLHA, to be obtained, preferably within 50 tube inversions or more preferably within 20 tube inversions.

It is clear that XLHA has a high or higher viscosity, in particular compared to that of non-crosslinked (e.g. linear) HA polymer and/or gel. However, in particular according to the present invention(s), it is strongly preferable that the viscosity of the XLHA (typically of the XLHA-containing gel) is within a range that allows effective and/or homogeneous mixture with PRP to be obtained (even if, for example, an increased number (>50 or >20) of tube inversions are required to obtain the effective and/or homogeneous mixture with PRP).

XLHA (in particular according to the present invention(s)), preferably when substantially not (e.g. not) in a mixture with PRP, can also be used in the preparation of syringes, for use in the main treatment fields (preferably for use in treatments and/or prophylaxes in the fields of dermatology and/or orthopedics, preferably in humans) and for other similar and/or analogous treatments. In this case, because typically substantially no PRP (e.g. no PRP) is involved or used or admixed, the viscosity of the XLHA, in particular according to the present invention(s), can be higher than the viscosity of XLHA intended to be used in XLHA-PRP mixtures.

So XLHA, in particular according to the present invention(s), will preferably be involved in the production of pharmaceutical compositions and/or tubes (e.g. Regen Matrix™ tubes) containing XLHA and PRP. It is also likely and preferable that XLHA, in particular according to the present invention(s), will be involved in the production of syringes containing the XLHA gel but containing substantially no PRP (e.g. no PRP).

In particular in the present invention(s), e.g. because of the cross-linked network of the XLHA, the gel and/or the XLHA preferably has a residence time longer than the 30 days residence time of a non-crosslinked (non-XL) HA gel (e.g. a typical and/or conventional non-XL HA gel).

In the present invention & specification, "residence time" is preferably defined and/or is preferably measured according to the method disclosed in ISO_10993-6_2016 (i.e. or preferably, linear HA is completely degraded after 1 month).

In particular in the present invention(s), by modulating the % (percentage) of cross-linking and/or modification, preferably in a XLHA gel according to and/or as used in the present invention(s), the residence time will usually be changed. It is desirable to keep in mind the viscosity restrictions (the preferred viscosity range) which may be set by the final use/application of eg the XLHA.

In fact, it is believed that the higher the % of cross-linking and/or modification, the higher is the residence time (which is often desirable), but also the higher the viscosity might become (which may be undesirable if the viscosity is too high, depending eg on the intended use of the XLHA).

Considering all of the above facts and factors, in the present invention(s), it is preferred to use, in particular for use in tubes, a XLHA that will be substantially completely absorbed in vivo after administration (preferably substantially completely absorbed by a human body to which the XLHA has been administered) within a period of 6 months (preferably within 3 months), and more preferably leaving permanent and/or long-lasting therapeutic effects (preferably, therapeutic effects lasting longer than 3 months or longer than 6 months).

In the present invention(s), it is preferable that the gel, typically the XLHA gel and/or the XLHA-containing gel, is able to pass through a 27 G needle/cannula and/or through a 22 G needle/cannula (preferably at 0-40 degrees C., preferably at 10-30 degrees C. such as 15-25 degrees C.). This is to allow ready administration, e.g. to a human, of the XLHA-containing gel and/or the XLHA-containing pharmaceutical composition by injection through a 27 G needle and/or a 22 G needle/cannula. More preferably, the gel (typically the XLHA gel and/or the XLHA-containing gel) is able to pass through a 22G1/2 needle/cannula and/or through a 27G1/2 needle/cannula, preferably at the above-stated temperatures.

Example 1A: Development of "ONE POT" Method for the Synthesis of XLHA

In the present invention(s), two different synthesis using two different quantities (concentrations and/or molar percentages) of BDDE have been performed, which therefore resulted in two different final percentages of cross-linking.

As already proposed previously, and as discussed herein e.g. hereinabove, rotation/revolution mixing as well as a pouch are used in the syntheses of the XL products (XLHA). Analyzing these methods, it is clear that a lot of manipulations are involved. At first such methods were used, to give some baseline evidence of the procedure and of the gel, e.g. XLHA gel, obtained.

In the synthetic process, there are 5 fundamental phases that can be performed in different steps.

Considering the number of manipulations done using the previously-published methods of making XL HA, the length of the synthetic procedure using these methods, and the explosion of the products (the number of products formed), according to the present invention(s), an alternative method of making (synthesizing) crosslinked HA is now provided.

Reactors have been commonly used in laboratories for the development of new synthetic processes. Reactors are sometimes used for preparation of polymers and/or API (Active Pharmaceutical Ingredients), in particular in pilot plants e.g. of chemical and/or pharmaceutical industries.

According to one aspect of the present invention, a continuous one-pot method of producing XLHA according to the present invention(s) has been developed. The method is convenient, efficient, works well, and/or is generally suitable for process automatization. Preferably, the XLHA is produced within a chemical reactor vessel, in particular within a pilot-plant-type chemical reactor vessel.

Several batches have been produced using this continuous one-pot process/method of the present invention.

As shown in Scheme 1A5 below/herein, the first phase of the continuous one-pot process is the hydration of the HA fibers or HA powder:

Step 1. HA polymer fibers or powder is transferred into the reactor, which then is closed. Solvent is then added while being filtered (preferably filtered using a 220 μm mesh filter), or is added after having been filtered, under stirring through a feeding vessel. As alternative, with the reactor already closed, HA polymer powder is added using the solid input port, and then solvent is added e.g. as described above. The temperature at this point is preferably room temperature (typically 10-40 degrees C., preferably 15-30 degrees C., more preferably 17-25 degrees C.).

Step 2. After homogenization of the mixture by stirring, a basic (alkaline) aqueous solution containing a crosslinking agent is added, and the pH is measured.

Step 3. The temperature is raised up to 50° C., with the mixture being stirred. After 2 hours at 50° C. under stirring, the reaction mixture is cooled or allowed to cool to room temperature (typically 10-40 degrees C., preferably 15-30 degrees C., more preferably 17-25 degrees C.).

Step 4. The reaction mixture is then neutralized by addition of an acid, preferably an aqueous acid. Preferably, an aqueous solution of HCl in PBS (phosphate buffered saline solution) is added to the reaction mixture, e.g. though a feeding vessel, preferably while being filtered. The pH is checked to ensure that the physiological conditions (i.e. neutral pH, a pH of about 7) have been reached. Neutral pH will reduce the reactivity of HA and/or XLHA towards any remaining crosslinking agent, because the hydroxyl groups of HA and/or XLHA will be much less deprotonated than a thigh pH, and hence the hydroxyl groups will be less reactive.

Step 5. The mixture is cooled or allowed to cool to 4° C., and is kept stirring at about 4 to 5° C. overnight (i.e. for about 8-20 hours, preferably for about 10-16 hours). The pH of the mixture is checked again at the end of this phase. The low temperature should also reduce the reactivity of the system (e.g. of the HA and/or XLHA), and/or should allow complete homogenization, and/or a substantial degree of homogenization, without further cross-linking.

Step 6. Finally, the mixture is warmed or allowed to warm back to room temperature (typically 10-40 degrees C., preferably 15-30 degrees C., more preferably 17-25 degrees C.). A certain quantity of non-crosslinked HA (of the type/ grade which is typically used in Cellular Matrix™ tubes) (approximately the same molecular weight, M.W.) is added, in order to obtain a desired viscosity. The desired viscosity can preferably be a viscosity which is necessary to hold a or the separating gel and/or to allow formation of a mixture, preferably an effective and/or homogeneous mixture, of [the XLHA and preferably also HA] with PRP. The non-crosslinked HA polymer is added to the mixture, preferably through a feeding vessel, and the mixture is left stirring until complete and/or substantial homogenization of the reaction mixture has been achieved.

Step 7. At this point, the gel is collected from the reactor and is filtered (preferably using a 280 μm mesh filter).

Scheme 1A5: The reactor used for the reaction between HA and the crosslinking agent (BDDE). The numbered items are Steps 1 to 7 of the synthetic process, as disclosed FIG. 1.

In this way, most or all of the synthetic process (preferably substantially the entire synthetic process) is (preferably) performed in a closed environment, preferably without substantially exposing the gel to possible contamination.

Also, the continuous and/or "one-pot" process to prepare crosslinked XLHA (preferably with non-XL HA added later) generally allows better homogenizations of the synthetic mixture during the process, and the manipulations during the process are reduced compared to previously-published methods, and hence the time to perform the synthesis is generally consistently shorter.

The final phase of the process is the purification of the XLHA, preferably purification by dialysis. This dialysis method is preferably used because it enables separation of molecules of different sizes which are both soluble in the same solvent. During purification by dialysis, any unreacted BDDE, which may be present in the XLHA-containing mixture or gel, is generally eliminated (or reduced, typically greatly reduced, in its concentration) by passing through a or the dialysis membrane, while (preferably) water will enter into the XLHA-containing mixture or gel allowing further swelling of the polymer(s). The final concentration of the polymer(s) eg of the XLHA is then reached, and residual BDDE should then be present only in trace amounts, and if desired can be further reduced after a further sterilization process.

In fact, the quantity (concentration) of residual BDDE has been tested for most or all of the batches of XLHA gel produced and purified with different dialysis membranes and/or at different temperatures and/or further sterilized or degassed.

The so-obtained XLHA gel can then be used in the production of a medical device (e.g. tube or syringe), which itself can be used for the preparation of A-PRP.

WO 2011/110948 (A. Turzi) and/or WO 2013/061309 A2 (A. Turzi; "New a-prp medical device & tissue engineering composition, manufacturing machines and process") disclose the use of a tube containing [non-crosslinked HA, a thixotropic gel and an anticoagulant], for the preparation of a mixture of PRP and HA.

The general disclosures in WO 2011/110948 and/or WO 2013/061309 A2 can be used by the reader as a technical primer, when mixtures of XLHA and PRP (according to the present invention) are being prepared.

Example 1B: Physical Chemical Characterization of Samples of Hyaluronic Acid (HA) and/or Crosslinked Hyaluronic Acid (XLHA)

1. Introduction/Scope of the Report

The synthesis of the cross-linked Hyaluronic acid (XLHA) has been performed using the one pot method and different quantities of crosslinker (BDDE), e.g. as disclosed in Example 1A hereinabove and/or Example 1C hereinbelow.

Ten samples have been sent for qualitative and quantitative hydrodynamic characterization with SEC-TDA (size exclusion chromatography combined with a triple detector array of light scattering, refractometry and viscometry) of the soluble fraction of the samples.

Six more samples (before and after sterilization) collected from the three validation batches have been sent afterwards. The batches have been all synthesized using a 1500 kDa HA fibers crosslinked with BDDE in basic conditions and with the previously described one-pot method.

Moreover, a sample of linear HA produced by Regen Lab has been sent as a reference. A qualitative and quantitative hydrodynamic characterization with SEC-TDA of the soluble fraction of the samples was performed on the new samples.

Moreover, selected samples have been characterized from a physical chemical point of view by performing rheology studies, enzymatic degradation, cohesivity tests and swelling.

Methods and results concerning this study are written according to the report sent by the DMS.

2. Objective of Characterization

The characterization of these samples is necessary to understand if the synthetic process used for the synthesis of XLHA can produce the same type of gel hence if it is reproducible or if there are any correlation between the parameters used.

The analysis performed have focused again on the quali-quantitative characterisation of the soluble fraction of the three validation batches, and on the physical chemical characterization of a group of representative samples. In particular, a study has been performed on sterile samples, to understand the rheological behaviour of the gel at different physiological relevant frequencies.

3. Description of Samples

Herein reported the table with the list of samples analysed. Only the sterilized samples of some selected batches have been studied from a rheological point of view. The list reports the batches in order of production and the reference of the syringes used for the analysis of the linear HA.

The synthesis of batches 6, 7 and 8 is performed by adding an excess of BDDE to a solution of HA (1:453 molar ratio).

TABLE 1 specification of batches analysed.

| | | TYPE/LOT | Environment | WEIGHT | HA | MW (KDa) | Intrinsic Viscosity | BDDE (g/stoichiometric ratio) | Swelling percentage | Concentration (mg/ml) |
|---|---|---|---|---|---|---|---|---|---|---|
| 1 | one pot kenwood | Soft/02J17 | Laboratory | 1l | HTL | 1550/1550 | 1.81 m3/kg | 1.1/453 | 11% | 20.1 |
| 2 | One pot | Soft/21K17 | Laboratory | 3l | HTL | 1550/1550 | 1.92 m3/kg | 3.3/453 | ≈6% | 22.4 |
| 3 | round | Soft/30A18-D | Laboratory | 3l | HTL | 2800 | 2.77 m3/kg | 3.3/833 | 4% | 24.5 |
| 4 | bottom | Soft/12B18-D | Laboratory | 3l | HTL | 2800 | 2.77 m3/kg | 5.4/4449 | 4% | 24.4 |
| 5 | flask | Soft/19B18-D | SB10 | 3l | Shiseido | ≈2000 | NC | 3.3/604 | 6% | 22.5 |
| 6 | BIO-COMPATABILITY | Soft/26C18-D | SB1 | 1l | HTL | 1550/1550 | 1.82 m3/kg | 3.3/453 | 6% | 20.8 |
| 7 | IMPLANTATION | Soft/04D18-D | SB1 | 1l | HTL | 1550/1550 | 1.82 m3/kg | 3.3/453 | 6% | 20.8 |
| 8 | TEST | Soft/10D18-D | SB1 | 1l | HTL | 1550/1550 | 1.82 m3/kg | 3.3/453 | 6% | 20.8 |
| 9 | | ARV-HA-40-318D04 | SB10 | 3l | HTL | 1550 | see OF | NA | NA | 20 |

For the analysis of the soluble fraction of batches 6, 7 and 8, a sample of the gel before and after sterilization (at 121 00 for at least 15 minutes) has been collected (indicated as BS and AS) and analyzed. Rheological study has been performed only on sterilized samples of batches 2, 3, 4, 6, 7, 8 and 9 considered more representative. Sample 5 has been excluded as no cross-linking occurred.

4. Material and Methods 4.1 Extraction of the Soluble Fraction

The analysis has been performed on samples 26C18-D BS, 26C18-D AS, 04D18-D BS, 04D18-D AS, 10D18-D BS, 10D18-D AS, ARV-HA-40-3 18D04 and ARV-HA40-3 18D04 (which is a final sterilized product containing linear HA. Samples have been diluted 5 times in a phosphate buffer (PBS) with a pH of 7.4 (1.5-2 ml of final volume). Suspensions have been Shaken for 18 hours at 37° C. then centrifuged for 5 min at 10000×g.

Only samples 04D18-D BS and ARV-HA40-3 18D04 appear to be homogeneous, while all the others separates after centrifugation, showing the presence of two phases of different viscosity but anyway not separable. Samples have then been diluted 2 more times, then filtered with a 0.22 µm filter. The supernatant containing the soluble HA has been analysed.

4.2 Quantitative Analysis of Soluble Fraction of HA.

The HA content (mg/ml) has been measured using two techniques (colorimetric test and SEC-TDA analysis)[iiiii]. The content of soluble HA has been calculated considering the dilution performed for each sample.

Each sample has been analysed at least twice and for each analysis two quantitative calculation have been performed. Hence values of soluble fraction obtained for each sample, have been obtained after at least 4 measurements.

4.3 Hydrodynamic Characterization of the Soluble Fraction of HA (Linear and Cross-Linked) Using SEC-TDA Hydrodynamic parameters of the soluble fraction of HA contained in each of the analysed samples, have been determined by Size exclusion chromatography (SEC) equipped with a triple detector (TDA-light scattering, refractometry and viscosimetry). The analysis has been performed on the samples prepared with the method described in the paragraph above.

SEC equipment (Viscotek, Malvern, UK) is composed by two moduli:
1) GPCmax VE 2001, integrated system constituted by a specific pomp for the Gel Permeation Chromatography (GPC), a system for degassing the solvent connected in line, and an autosampler;
2) TDA305 modulus (Triple detector array) which includes a thermostatic oven for the column, and a triple detector for refractive index (RI, a viscometer with 4 capillary bridges (VS and a Light scattering (LS). The latter is formed by two parts: a Right-Angle Light Scattering (RALS) with a very good signal-noise ratio, and the innovative Low Angle Scattering (LALS)

Dn/dc value (infinitesimal variation of the signal intensity, measured by the refractive index detector, upon variation of the analyte concentration) used for HA is 0.155 ml/g.

At least two solutions of each samples have been prepared and for each solution at least two chromatographic analysis have been performed (chromatographic curves are reported in Annex 1). Average Molecular Weight ($M_w$), average numeric molecular weight ($M_n$), polydispersity index ($M_w/M_n$), intrinsic viscosity ($[\eta]$) and hydrodynamic radius ($R_h$) are reported in Table 2

4.4 Rheological Characterization

The study of the rheologic behaviour was performed using a rheometer Anton Paar Physica 301, equipped with a measuring system composed by a stainless-steel plate-plate of 50 mm and with a gap of 0.9 mm, using the method reported by La Gatta et al[ii] Values have been measured at two frequencies: 0.159 and 15.90 Hz.

4.5 Enzymatic Resistance/Degradation

A preliminary kinetic study focused on the enzymatic degradation of one of the samples has been performed. The experiment aims to understand the behaviour of HA when exposed to the enzymatic activity. Sample 30A18-D has been incubated with the BTH (Bovine Testicular hyaluronidase), following the protocol described in literature.[iii]

In particular. Sample 30A18-D, having a concentration of 22.4 mg/ml, has been diluted to 4 mg/ml in PBS at pH7.4 and incubated wit BTH 0.5 U/ml. After different incubation times (2, 3, 6 and 24 h), the samples have been heated up to 100° C. for 10 minutes to inactivate the enzyme and then be characterized by SEC-TDA. The degradation has been monitored by measuring the decrement of the hydrodynamic parameters during incubation and in particular the decrease of the MW.

The degradation has been compared to a reference of linear HA available in the lab having similar MW. For each time point the analysis has been performed three times 4.6 Cohesivity Test Cohesivity of each sample has been evaluated using the methodology described by Sundaram and co.[iv] 1 ml of each sample has been coloured with 10 ml of a 1% solution of toluidine blue then placed in a 1 ml syringe and extruded into a Becker containing 700 ml of MilliQ water. The solution was magnetically stirred starting from when the gel touches the bottom of the Becker. Test is documented with a video and a photo taken at 15", 70" e 95" from the extrusion.

4.7 Swelling

Tests have been performed on samples with an evident insoluble HA fraction chosen in between all the samples which have been sent and analysed, which are 12B18-D BS and AS, 26C18-D BS and 10D18-DAS.

0.2 ml of each gel have been diluted in PBS to 1 ml and incubated at 37° C. and 800 rpm for 16 h. The degree of water uptake has been measured on incubating 0.2 ml aliquots of each gel in PBS to a final volume of 1 ml. Samples have been then centrifuged at 13000 g for 5 min and the supernatant separated from the hydrated gel. The degree of water uptake is measured as volumetric expansion of the gel once it has reached the swelling equilibria (hydrated gel 8 g)/initial gel (g).

5. Results and Discussion 5.1 Soluble Fraction

All the sample present a soluble fraction. Batch 10D18-D AS and 26C18-BS showed the smaller soluble fraction compared to the other batches. Considering that all the batches have a comparable total HA concentration (soluble+ insoluble) this batches have the higher percentage of insoluble HA (chemically modified). On the other hand, samples 04D18-D BS and ARV-HA-40-3 18D04 contain the higher percentage of soluble HA showing the lower degree of modification. This result is in accordance with the fact that ARV-HA-40-3 18D04 is a linear HA while the same results for 04D18-D BS suggests that no or very low chemical modification has occurred.

Here below Table 1 shows the value obtained for each sample sent:

TABLE 1 summary of results of $M_w$, $M_n$, $M_w/M_n$, $[\eta]$ and $R_h$.

| | TYPE/ LOT | MW (KDa) | BDDE (g/ stoichio-metric ratio | Concen-tration (mg/ml) | Soluble Fraction mg/ml (BS/AS) | Insoluble Fraction mg/ml (BS/AS) (data obtained by subtraction-non experimental) | Mw kDa (BS/AS) | Mn (BS/AS) | Mw/Mn (BS/AS) | $[\eta]$ dl/g (BS/AS) | Rh (nm) (BS/AS) |
|---|---|---|---|---|---|---|---|---|---|---|---|
| 1 | one pot kenwood | Soft/ 02J17 | 1550/ 1550 | 1.1/453 | 20.1 | 20 +/− 2 | 0.1 | 649 +/− 27 | 338 +/− 13 | 1.9 +/− 0.1 | 6.9 +/− 0.1 | 38 +/− 1 |
| | | | | | | 16 +/− 2 | 4.1 | 768 +/− 18 | 474 +/− 20 | 1.6 +/− 0.1 | 8.1 +/− 0.1 | 43 +/− 1 |
| 2 | One pot | Soft/ 21K17 | 1550/ 1550 | 3.3/453 | 22.4 | 19 +/− 2 | 3.4 | 899 +/− 7 | 529 +/− 1 | 1.7 +/− 0.1 | 8.8 +/− 0.1 | 47 +/− 1 |
| | | | | | | 19 +/− 3 | 3.4 | 705 +/− 20 | 369 +/− 29 | 1.9 +/− 0.1 | 7.8 +/− 0.1 | 41 +/− 1 |
| 3 | round bottom flask | Soft/ 30A18-D | 2800 | 3.3/833 | 24.5 | 17 +/− 1 | 7.5 | 1120 +/− 93 | 625 +/− 65 | 1.8 +/− 0.1 | 11.0 +/− 0.1 | 54 +/− 1 |
| | | | | | | 22 +/− 1 | 2.5 | 625 +/− 22 | 334 +/− 22 | 1.9 +/− 0.1 | 8.2 +/− 0.1 | 40 +/− 1 |
| 4 | | Soft/ 12B18-D | 2800 | 5.4/4449 | 24.4 | 6 +/− 2 | 18.4 | 818 +/− 35 | 419 +/− 36 | 2.0 +/− 0.1 | 10.8 +/− 0.2 | 48 +/− 1 |
| | | | | | | 7 +/− 1 | 17.4 | 750 +/− 25 | 413 +/− 27 | 1.8 +/− 0.1 | 8.2 +/− 0.2 | 43 +/− 1 |
| 5 | | Soft/ 19B18-D | ≈2000 | 3.3/604 | 22.5 | 22 +/− 1 | 0.5 | 1045 +/− 79 | 586 +/− 27 | 1.8 +/− 0.1 | 10.8 +/− 0.2 | 52 +/− 2 |
| | | | | | | 22 +/− 0 | 0.5 | 655 +/− 19 | 334 +/− 18 | 2.0 +/− 0.1 | 8.6 +/− 0.2 | 42 +/− 1 |
| 6 | BIO-COM- | Soft/ 26C18-D | 1550/ 1550 | 3.3/453 | 20.8 | 6 +/− 1 | 14.8 | 1085 +/− 26 | 720 +/− 17 | 1.5 +/− 0.1 | 11.7 +/− 0.1 | 55 +/− 1 |
| | | | | | | 13 +/− 1 | 7.8 | 952 +/− 54 | 564 +/− 57 | 1.7 +/− 0.1 | 10.4 +/− 0.2 | 51 +/− 1 |
| 7 | PAT-IBILITY | Soft/ 04D18-D | 1550/ 1550 | 3.3/453 | 20.8 | 21 +/− 2 | −0.2 | 897 +/− 129 | 508 +/− 84 | 1.8 +/− 0.1 | 8.6 +/− 0.4 | 46 +/− 3 |
| | | | | | | 17 +/− 2 | 3.8 | 902 +/− 17 | 499 +/− 18 | 1.8 +/− 0.1 | 8.9 +/− 0.1 | 47 +/− 1 |
| 8 | IM-PLAN-TATION | Soft/ 10D18-D | 1550/ 1550 | 3.3/453 | 20.8 | 12 +/− 2 | 8.8 | 1228 +/− 79 | 770 +/− 32 | 1.6 +/− 0.1 | 12.9 +/− 0.1 | 59 +/− 1 |
| | | | | | | 6 +/− 2 | 14.8 | 1152 +/− 43 | 771 +/− 45 | 1.5 +/− 0.1 | 12.6 +/− 0.2 | 58 +/− 1 |
| 9 | TEST | ARV-HA-40-318D04 | 1150 | | 20/21 | 21 +/− 2 | 0 | 756 +/− 25 | 552 +/− 62 | 1.4 +/− 0.1 | 13.6 +/− 0.1 | 53 +/− 1 |

Batch 26C18-D shows an increase of the soluble fraction after sterilization that goes within the decrease of the $M_w$.

Batch 04D18-D on the contrary shows a decrease of the soluble fraction and an increase of the $M_w$, as already observed for sample 02J17 discussed in the report n° HARET_CHARAC_2018_06 of 05.06.2018.

The assumption made is that a higher residue of BDDE was present in the batch after dialysis, hence the cross-linking reaction might have continued during sterilization.

A different situation occurred in the case of batch 10D18-D where an important decrease of the soluble fraction was observed for the sterilized sample, but the Mw slightly decreased.

The explication can be the same given for samples 04D18-D and 02J17.

In fact, all the variation observed, besides for the samples where the Mw decreased of ½, were very small such that it fell inside the error found for each value, allowing to say that, no significant variation occurred.

5.2 Hydrodynamic Parameters

All the samples have a soluble fraction with a Mw higher than 700 kDa. In particular, samples 26C18-D BS and 10D18-D BS and AS have a Mw of 1100-1200 kDa. The polydispersity index is generally between 1.4 and 1.8. In fact, a decrease of values is already observed for the samples BS probably because of the effect of the temperature during cross-linking (50° C. during 2 hours).

Figure 7A:
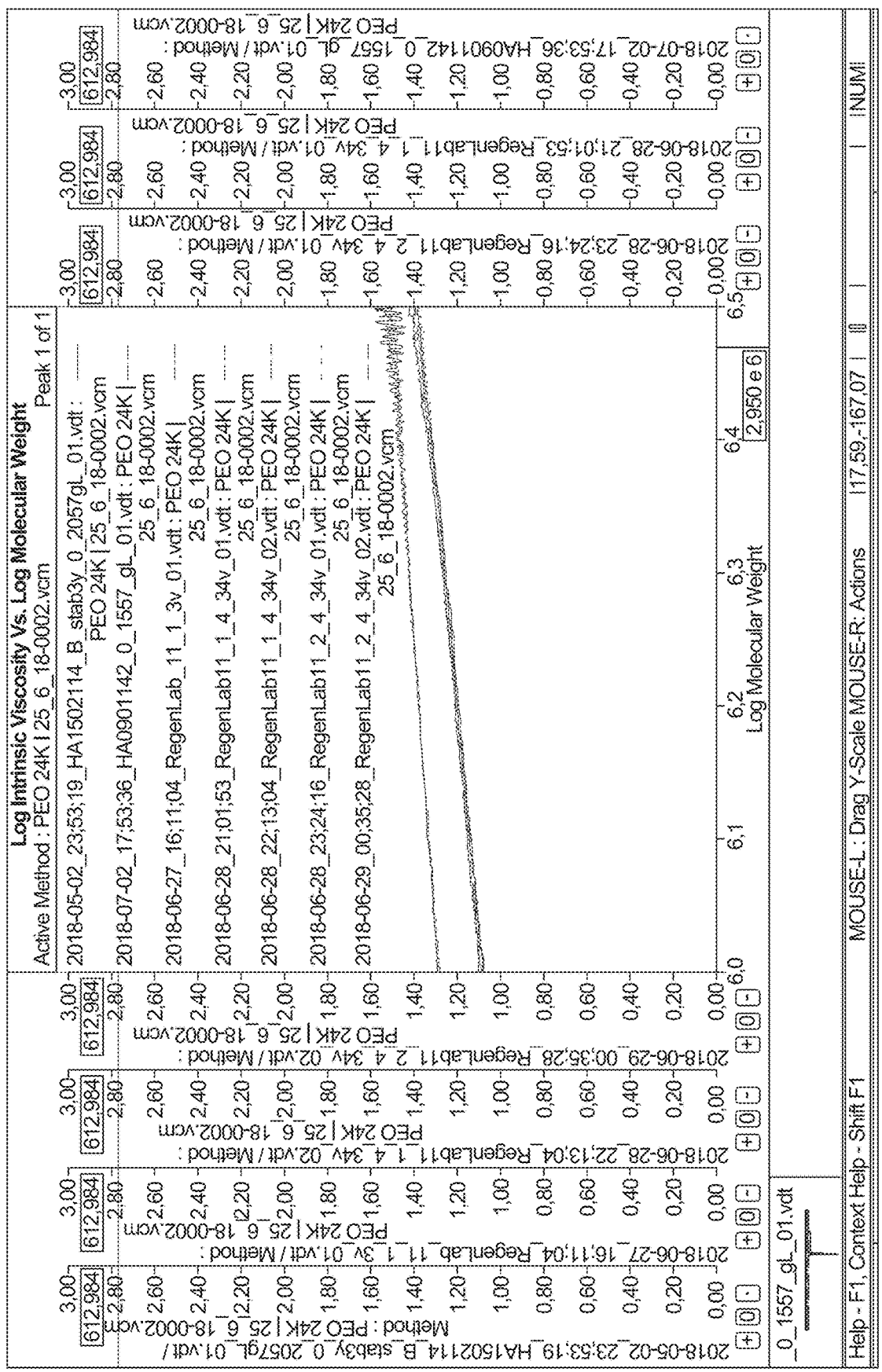
FIG. 7 is a Mark-Howking curve for a sample of generic linear HA and for soluble fraction of samples 04D18-D AS (a), 10D18-D AS (b), 26C18-D (c) and ARV-HA-40-3 18D04 (d). See Example 1B hereinafter.
Figure 7B:
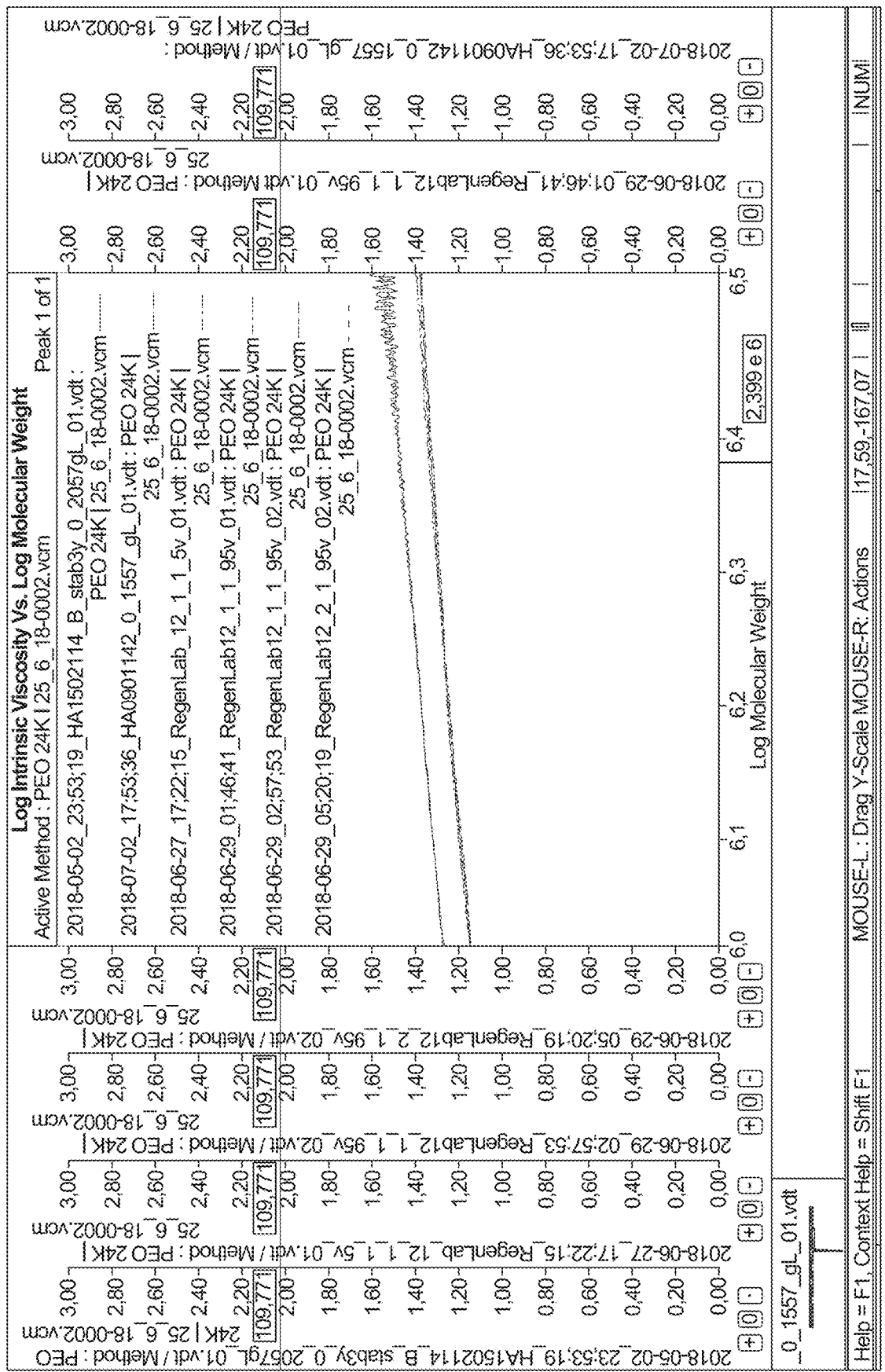
Figure 7C:
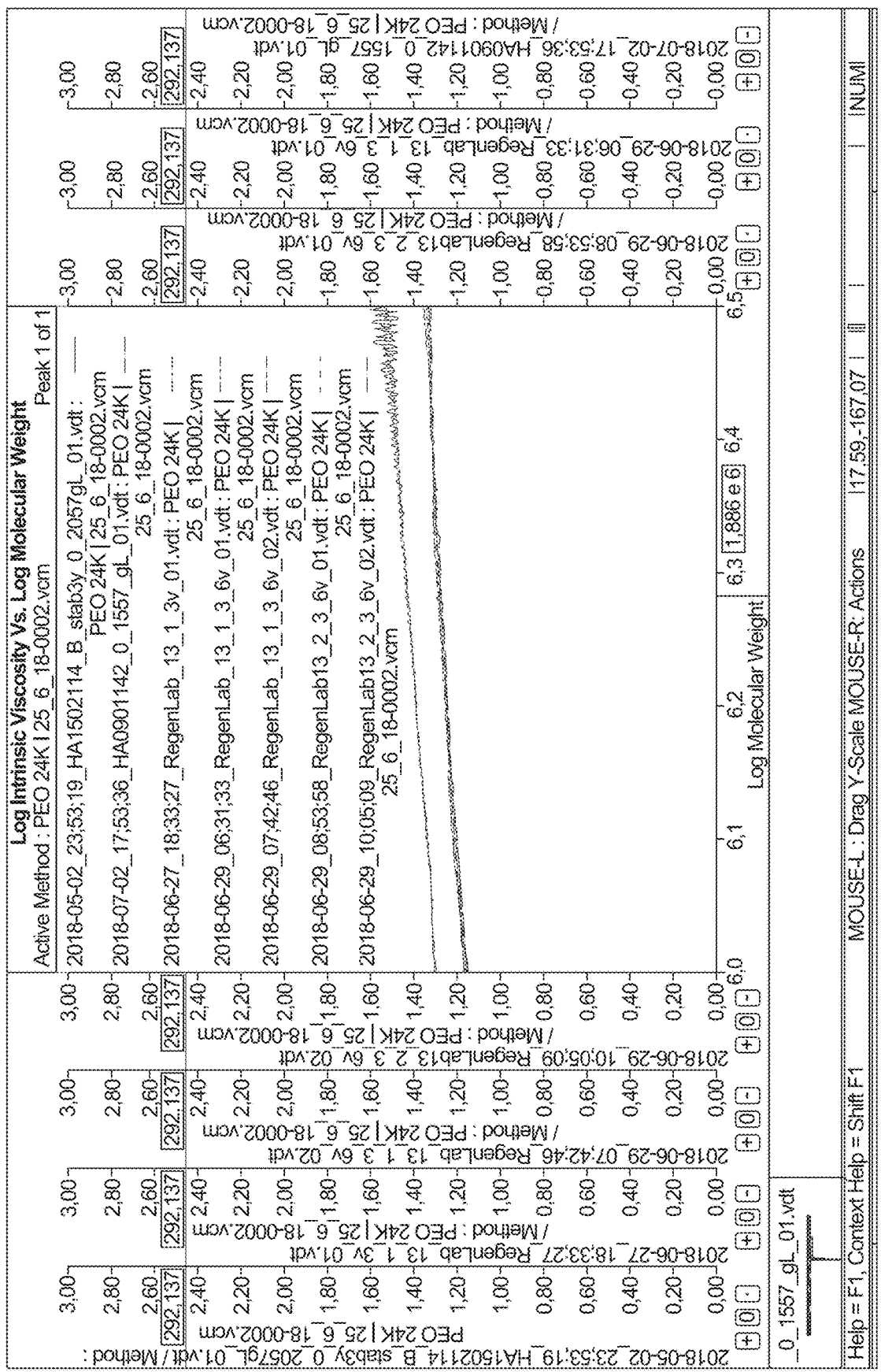
Figure 7D:
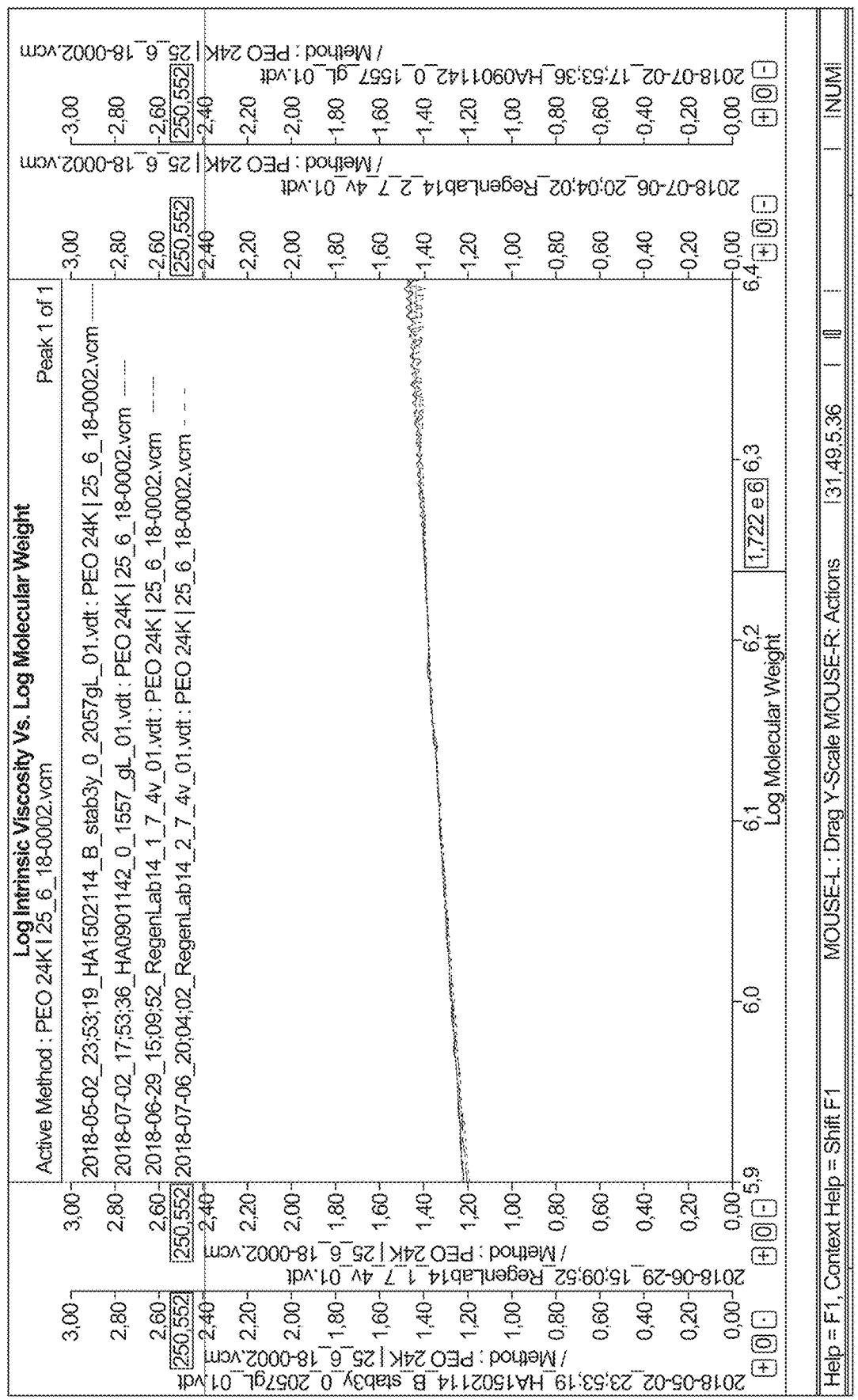

For each sample the SEC-TDA analysis allowed to also derive the Mark-Howking curve (MHS curve-log intrinsic viscosity vs log $M_w$). These curves (FIG. 7 shows the superimposition for samples 04D18-D AS (a), 10D18-D AS (b) and 26C18-D (c)) have been compared with the one of linear HA (non-modified) available at the department of experimental medicine in Naples. All the samples present soluble fractions that, if compared to the linear HA, present lower values of intrinsic viscosity at equal molecular weight. This indicates a more compact conformation of HA chains meaning that also the conformational analysis is compatible with the presence of cross-linked HA chains (or at least modified) in the soluble fractions. FIG. 7d refers to sample ARV-HA-40-3 18D04 perfectly superimposable with the linear HA available at the DMS and taken as a reference. This superimposition is generally observed for non-modified HA of for HA with a very low degree of modification which does not cause any conformational change visible with this technique.

This consideration given we can state that the samples analysed are all chemical modified.

5.3 Rheological Characterization

A rheological study has been performed at different frequencies between 0.159 and 15.9 Hz.

Figure 8:
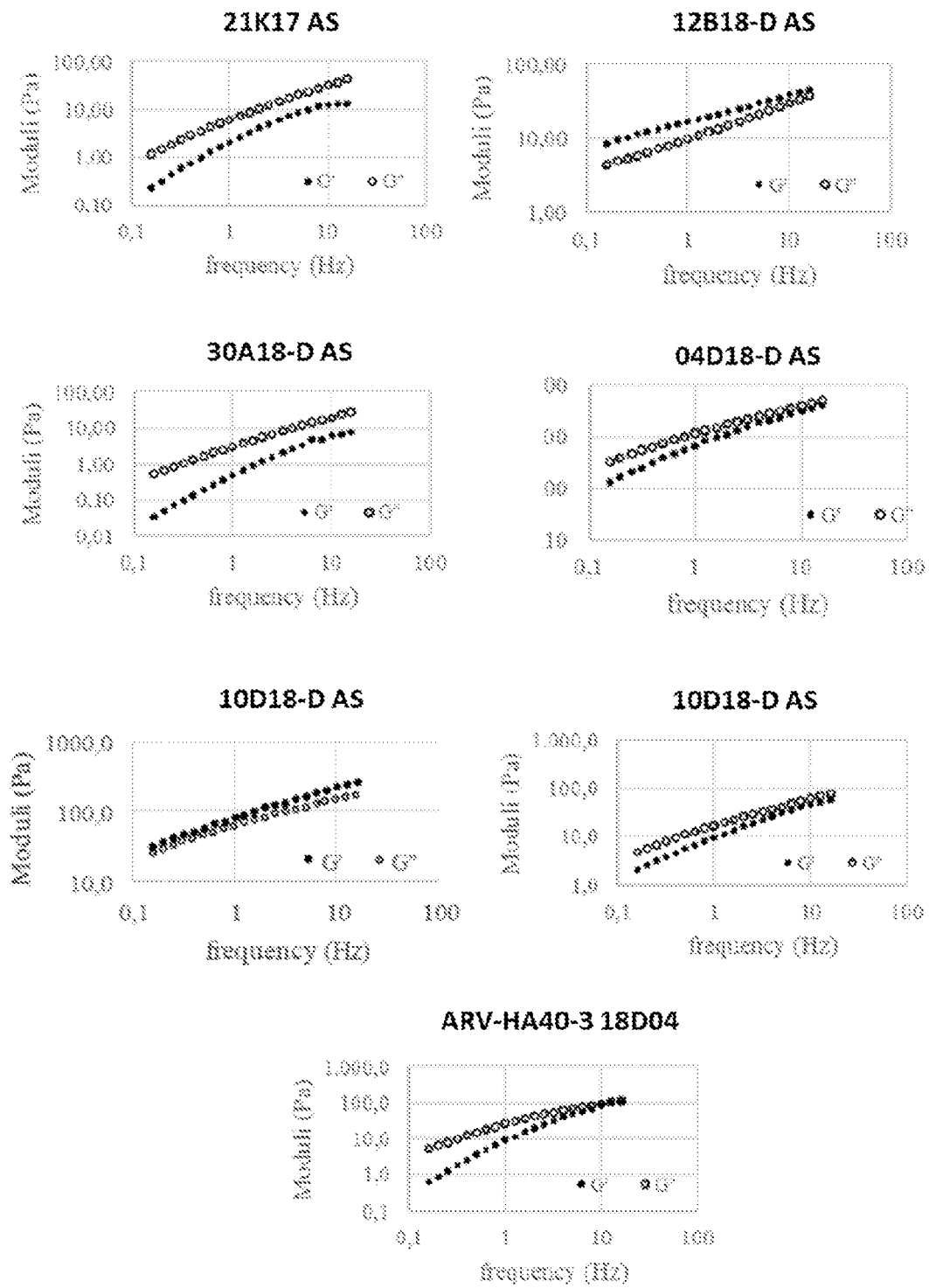
FIG. 8 (G' and G" vs frequency) shows graphs showing the values of G' and G" as a function of the different frequencies (Hz). See Example 1B hereinafter for details.
Figure 9:
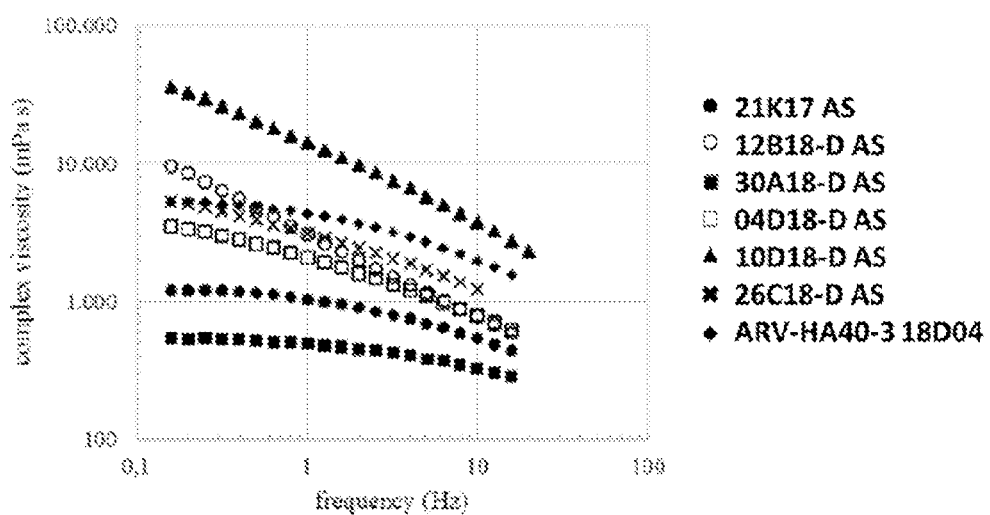
FIG. 9 is a graph of the value of the complex viscosity, as a function of the different frequencies (Hz). See Example 1 B hereinafter for details.

Here in FIG. 8 the graphs showing the values of G' and G" as a function of the different frequencies (Hz). In FIG. 9 is shown the graph of the value of the complex viscosity, as a function of the different frequencies (Hz). Both graphs give the results for the same batches which are listed in the figures. In Table 2 we report the values of G', complex viscosity and tan delta at 0.5 and 2.5 Hz.

FIG. 8: G' and G" vs frequency. Graphs showing the values of G' and G" as a function of the different frequencies (Hz).

FIG. 9: G' and G" vs frequency. In FIG. 9 is shown the graph of the value of the complex viscosity, as a function of the different frequencies (Hz).

similar values of Tan δ, and lower than the values measured for 21K17 AS, 30A18-D AS and ARV-HA-40-3 18D04.

According to the mechanical spectrum, for samples 12B18-D AS and 10D18-D AS, the complex viscosity constantly decreases with the frequency, in all the considered range. Samples 21K17 AS, 30A18-D AS and ARV-HA-40-3 18D04 initially present a constant behaviour followed by a thinning behaviour. Based on the data collected for samples 21K17 AS and 30A18-D AS, viscosity profiles are compatible with gels containing soluble HA and with a different conformation of the polymeric chains. For samples 26C18-D AS and 04D18-D an intermediate behaviour is observed with 2 zones with a different relation between complex viscosity and frequency.

5.4 Enzymatic Degradation

The effect of Bovine Testicular hyaluronidase has been investigated in order to have preliminary information on the resistance of XLHA to hyaluronidase and have a suggestion about the possible residence time in vivo.

Here below (FIG. 10) the graph that reports the change of Mw registered upon incubation with the BTH of sample 21K17-D AS (■) which has been compared with a linear HA (□).

Figure 10:
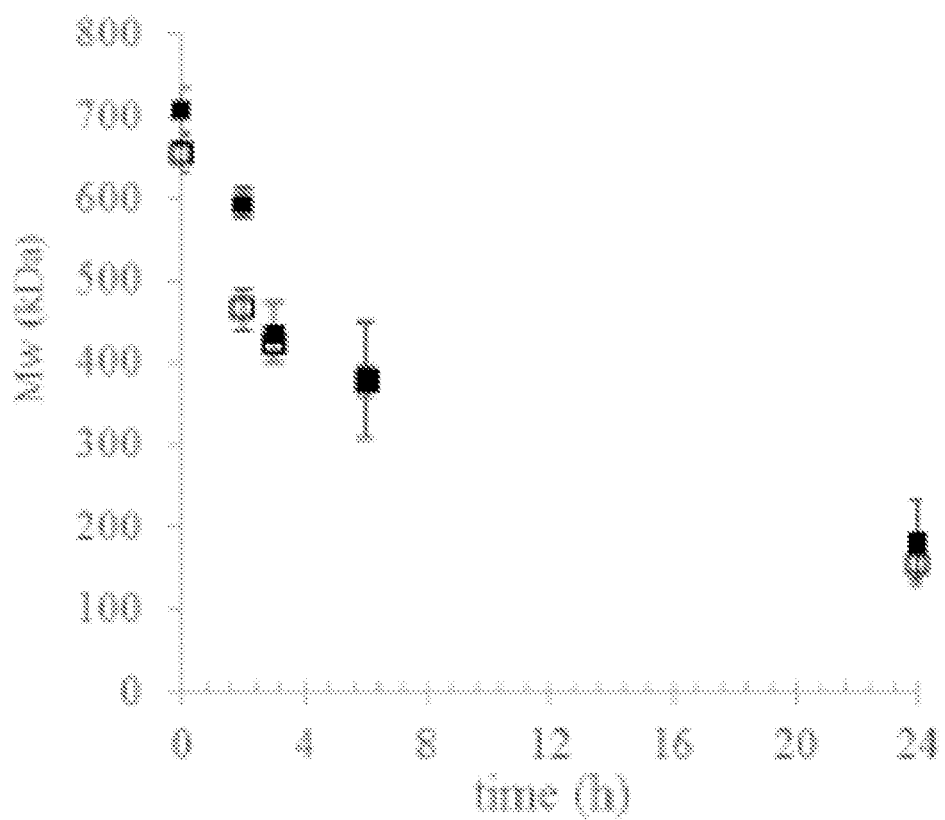
FIG. 10 shows Mw registered upon incubation with BTH 0.5 U/ml of sample 21 K1 7-D AS (□) and a linear HA (□). See Example 1 B hereinafter for details.

FIG. 10. Mw registered upon incubation with BTH 0.5 U/ml of sample 21K17-D AS (■) and a linear HA (□).

Figure 11A:
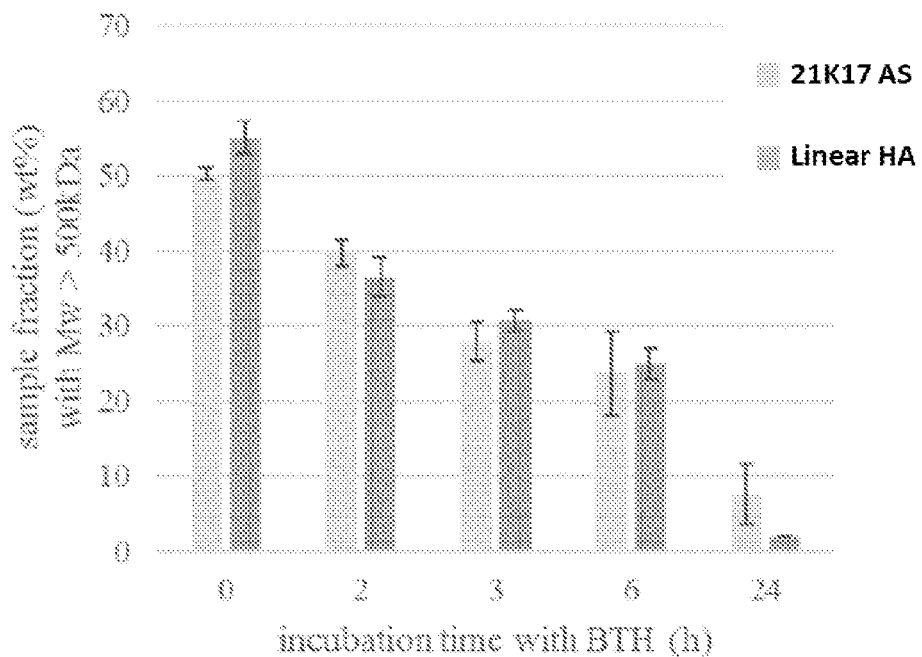
FIGS. 11(A) and 11(B) shows a variation of sample fraction (wt %) with Mw>500 kDa (a) and MW<200 kDa (b). See Example 1 B hereinafter fordetails.
Figure 11B:
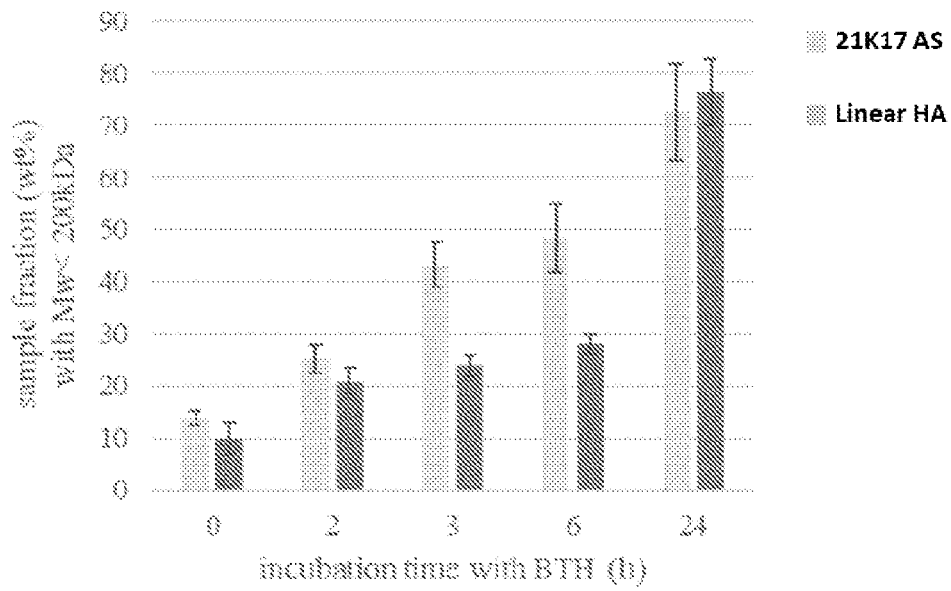

In FIG. 11 also the graphs that show the variation of sample fraction (wt %) with MW>500 kDa and MW <200 kDa Data demonstrate that both samples are sensible to depolymerization catalysed by BHT. Graphs reporting $M_w$ vs Incubation time show a similar depolymerization kinetics for the two samples which have a similar initial $M_w$. Only at

TABLE 2 values of G', complex viscosity and tan delta at 0.5 and 2.5 Hz.

| | | TYPE/LOT | MW (KDa) | BDDE (g/stoichiometric ratio) | Concentration (mg/ml) | Soluble Fraction mg/ml (BS/AS) | Mw kDa (BS/AS) | G' | | Complex Viscosity (Pas) | | tan delta | |
|---|---|---|---|---|---|---|---|---|---|---|---|---|---|
| | | | | | | | | 0.5 Hz | 2.5 Hz | 0.5 Hz | 2.5 Hz | 0.5 Hz | 2.5 Hz |
| 1 | one pot kenw | Soft/02J17 | 1550/1550 | 1.1/453 | 20.1 | 20 | 649 +/− 27 | | | | | | |
| | | | | | | 16 | 768 +/− 18 | | | | | | |
| 2 | One pot | Soft/21K17 | 1550/1550 | 3.3/453 | 22.4 | 19 | 899 +/− 7 | | | | | | |
| | | | | | | 19 | 705 +/− 20 | 0.99 | 4.99 | 1.15 | 0.85 | 3.54 | 2.51 |
| 3 | round bottom | Soft/30A18-D | 2800 | 3.3/833 | 24.5 | 17 | 1120 +/− 93 | | | | | | |
| | | | | | | 22 | 625 +/− 22 | 0.19 | 1.59 | 0.52 | 0.44 | 8.53 | 4.27 |
| 4 | flask | Soft/12B18-D | 2800 | 5.4/4449 | 24.4 | 6 | 818 +/− 35 | | | | | | |
| | | | | | | 7 | 750 +/− 25 | 13.2 | 22.9 | 4.76 | 1.74 | 0.54 | 0.67 |
| 5 | | Soft/19B18-D | ≈2000 | 3.3/604 | 22.5 | 22 | 1045 +/− 79 | | | | | | |
| | | | | | | 22 | 655 +/− 19 | | | | | | |
| 6 | BIOCOMPATIBILITY | Soft/26C18-D | 1550/1550 | 3.3/453 | 20.8 | 6 | 1085 +/− 26 | | | | | | |
| | | | | | | 13 | 952 +/− 54 | 5.64 | 19.3 | 39 | 2.24 | 1.94 | 1.53 |
| 7 | IMPLANTATION | Soft/04D18-D | 1550/1550 | 3.3/453 | 20.8 | 21 | 897 +/− 129 | | | | | | |
| | | | | | | 17 | 902 +/− 17 | 3.78 | 13.2 | 2.62 | 1.47 | 1.95 | 1.45 |
| 8 | TEST | Soft/10D18-D | 1550/1550 | 3.3/453 | 20.8 | 12 | 1228 +/− 79 | | | | | | |
| | | | | | | 6 | 1152 +/− 43 | 57.4 | 122 | 23 | 9.47 | 0.77 | 0.72 |
| 9 | | ARV-HA-40-318D04 | 1150 | | 20/21 | 21 | 756 +/− 25 | 3.63 | 25.5 | 48.9 | 3.45 | 4.14 | 1.89 |

Data reported in FIG. 7 show that samples 12B18-D AS and 10D18-D AS have a behaviour which is essentially elastic. This is in accordance with the value of soluble fraction which is the smallest for these two samples, and compatible with the presence of a covalent network. The other samples are rather viscous according to the values measured which is more representative of an entangled network (still chemically modified as confirmed by the MHS curves). For these latter samples crossover was measured at frequencies higher than 15.9 Hz. In between the viscous formulations, samples 26C18 AS and 04D18-D AS have 2 hours of incubation sample 21K17-D AS has a higher $M_w$. FIG. 11a shows as at each time point there is a comparable decrease of the fraction at 500 KDa for each sample. Results in FIG. 11 indicate, as presumable, an increase of the fraction with lower $M_w$ for both samples, upon incubation time with the enzyme. More in details, despite at the maximum incubation time the fraction at 200 KDa increased comparably for both samples, at 3 and 6 hours of incubation the same fraction is higher for the sample 21K17-D AS. Nevertheless, it is very important to consider that the results are independent from the overall distribution of the MW in the section that has been analysed. In conclusion the results do not show a significant difference between the samples at the enzymatic degradation.

The results can be explained also considering the soluble fraction of sample 21K17-D AS. In fact, the value reported is very close to the total concentration of HA in the sample, suggesting a very low degree of chemical modification which would explain a similar behaviour toward the enzymatic degradation.

FIG. 11: variation of sample fraction (wt %) with MW>500 kDa (a) and MW<200 kDa (b). Cohesivity Test Here below we report in FIG. 12 the cohesivity score (average of values given by three different operators based on the scale of cohesivity reported in literature (Sundaram et al., Plast Reconstr Surg.2015) for the validated method for which scores are:

1 Fully dispersed
2 Mostly dispersed
3 Partially dispersed, partially cohesive
4 Mostly cohesive
5 Fully cohesive.

Figure 12:
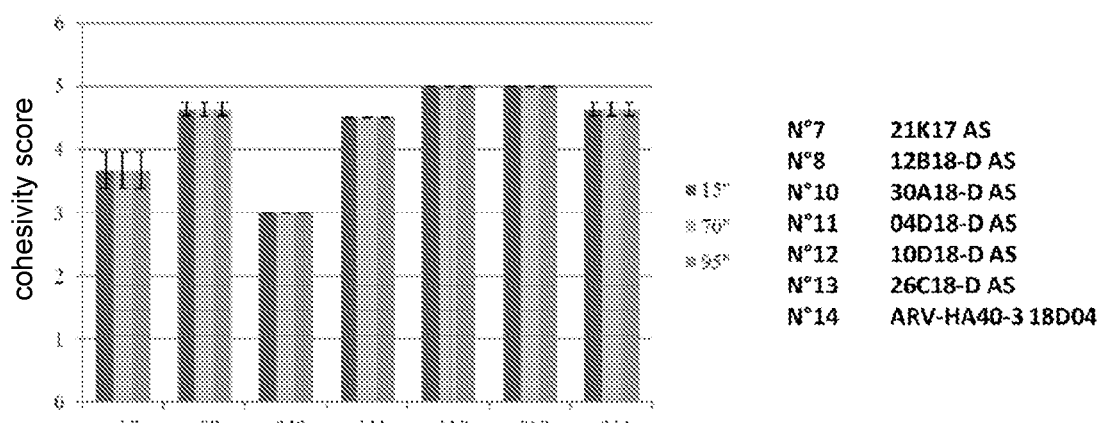
FIG. 12 shows values/parameters found according to the score reported in literature. See Example 1 B hereinafter for details.

Beside the sample n° 10 in general gels appear from mostly to completely cohesive, FIG. 12: Values found according to the score reported in literature.

5.5 Swelling

Tests have been performed only on samples with the higher insoluble fraction hence 12B18-D BS, 12B18-D AS, 10D18-D-AS and 26C18-D-BS Here the results obtained:

TABLE 3

Values corresponding to the degree of hydration

| Samples | Degree of Hydration (g/g) |
|---|---|
| 12B18-D BS | 3.1 ± 0.0 |
| 12B18-D AS | >2.1 |
| 10D18-D-AS | >1.7 |
| 26C18-D-BS | >1.7 |

Results indicate that sample 12B18-D BS increases its volume 3 times when left equilibrating in a physiologic medium. For the other samples which have all been sterilized, a small value of swelling has been reported has the separation between the pellet and the supernatant was very difficult. More precisely two phases have been observed with different flowing velocity and not completely separable: the less viscous part tends to mix when the more viscous when a separation is tried. The value of swelling is comparable between the three samples.

6 Conclusions

The analysis SEC-TDA confirmed that all the samples analysed contain soluble HA and that all the samples except ARV-HA40-3 18D04, contain HA which is chemically modified whit MW relatively high (≈1000 KDa).

The analysis performed at the Bioteknet confirm the presence of soluble HA in all the samples analysed. In particular, considering that all the samples have a total concentration of around 20 mg/ml (soluble+insoluble), the data reported in the table indicate that for the batches, analysed in this study the majority of HA is still soluble in aqueous media. Although, compared to the samples discussed in a previous report, certain batches show a smaller soluble fraction indicating a higher degree of chemical modification.

All the batches showed a $M_w$ higher that all the other commercial HA analysed in the same laboratory with the same techniques and used mainly as intradermic fillers (see data reported for Restylane in table 1). This is an important data on the resistance to sterilization and the possible shelf life. In fact, with temperature and time HA depolymerizes forming smaller fragment that can be pro-inflammatory (<50 Da). This result tells us that our gel is conforming to the requirement AS and might be stored for a considering amount of time (12-24 months) as for the already commercial ones.

The conformational analysis indicates that all the samples contain chemically modified HA and, the intrinsic viscosity is compatible with the presence of cross-linked HA.

Analysing the mechanical properties, it has been observed that 12B18-D AS and 10D18-D-AS present an elastic behaviour, which could be linked also to the higher value of insoluble fraction hence confirm a higher degree of modification, and the latter being even more rigid and viscous at the considered frequencies. Between the samples with a viscous behaviour, sample ARV-HA40-3 18D04, which is linear, has higher viscosity in the analysed range.

The only sample which has been tested for the resistance to the enzymatic degradation did not show such a degree of modification to be possible to differentiate it from a linear HA (in the experimental condition used).

The results are confirmed by the value of soluble fraction which is higher for the more viscous/elastic samples.

As reported in paragraph 5.5 most of the samples have high cohesivity and, having also, according to literature, distributes homogeneously within the tissues and in particular the dermis (Sundaram et al., Plast Reconstr Surg. 2015; study performed on gels used for skin care only) Finally, gel tested for swelling presented a good volumetric expansion which indicates a high ability of retrieve water inside.

The three batches 26C18-D-AS, 04D18_D_AS and 10D18-D-AS have been synthesized using the same method, nevertheless the soluble fraction and the rheological behaviour showed that there are some differences. By analysing in deep the report on the three syntheses, it was observed a difference in the total cross-linking time which is given by the time spent to arrive to 50° C. (cross-linking temperature) and the time spent at 50° C.

| | | TYPE/ LOT | Concentration (mg/ml) | Soluble Fraction mg/ml (BS/AS) | Insoluble Fraction mg/ml (BS/AS) (data obtained by subtraction-non experimental) | HA/ PBS-NaOH (min) | XL 50 C. ° (min) | Total XL (min) | NEUTRALISATION (MIN) | R2P (min) | Dialyse (min) | STERILISATION (min) | | |
|---|---|---|---|---|---|---|---|---|---|---|---|---|---|---|
| 1 | one pot kenwood | Soft/ 02J17 | 20.1 | 20 +/− 2<br>16 +/− 2 | 0.1<br>4.1 | 120 | 110 | 120 | 952 | 180 | 1487 | 4.23 | 15 | 6.46 |
| 2 | One pot | Soft/ 21K17 | 22.4 | 19 +/− 2<br>19 +/− 3 | 3.4<br>3.4 | 205 | 105 | 122 | 1043 | 240 | 1466 | 6.34 | 15 | 4.79 |
| 3 | round bottom | Soft/ 30A18-D | 24.5 | 17 +/− 1<br>22 +/− 1 | 7.5<br>2.5 | 120 | 200 | 258 | 1320 | 195 | 1452 | 6 | 16.1 | 7.32 |
| 4 | flask | Soft/ 12B18-D | 24.4 | 6 +/− 2<br>7 +/− 1 | 18.4<br>17.4 | 165 | 94 | 144 | 2513 | 240 | 1498 | 9.08 | 15 | 4.09 |
| 5 | | Soft/ 19/B18-D | 22.5 | 22 +/− 1<br>22 +/− 0 | 0.5<br>0.5 | 125 | 123 | 173 | 1068 | 285 | 1500 | N/C | N/C | N/C |
| 6 | BIO-COM- | Soft/ 26C18-D | 20.8 | 6 +/− 1<br>13 +/− 1 | 14.8<br>7.8 | 140 | 70 | 111 | 975 | 220 | 1660 | 5.19 | 15 | 8.25 |
| 7 | PATIBIL-ITY | Soft/ 04D18-D | 20.8 | 21 +/− 2<br>17 +/− 1 | −0.2<br>3.8 | 125 | 93 | 153 | 1143 | 255 | 1284 | 9.08 | 15 | 4.09 |
| 8 | IMPLANTATION TEST | Soft/ 10D18-D | 20.8 | 12 +/− 2<br>6 +/− 1 | 8.8<br>14.8 | 120 | 55 | 75 | 1037 | 240 | 1472 | 17.05 | 19.43 | 23.1 |

Considering the results obtained for the three samples up to now especially in reference to the insoluble fraction, new batches will be synthesized on the model of 26018-D-AS, hence keeping the gel at 50° C. for a maximum of 70 minutes.

To better understand the possible behaviour of our gels in vivo, more tests of the resistance to enzymatic degradation will be performed on batches 21 K17-D AS, 10D18-D-AS, 2618-D-AS and ARV-HA4-3 18D04, chosen as representative samples of all the range of the degree of modification obtained with a similar synthesis (Table 4).

Tests will be performed upon time using a fixed dose of BHT and upon the addition of different doses of enzyme and measured after 2 hours of digestion.

TABLE 4

Summary of the batches and the tests

| Sample | Time response test 0.5 U/ml | Dose response test (2 h) |
|---|---|---|
| 21K17-D AS | 2, 3, 6 and 24 | 1, 2, 5 10 U/ml |
| 10D18-D-AS * | 2 and 24 h | 1, 2, 5 10 U/ml |
| 26C18-D-AS * | 2 and 24 h | 1, 2, 5 10 U/ml |
| ARV-HA40-3 | 2, 3, 6 and 24 | 1, 2, 5 10 U/ml |

* Investigation on soluble and insoluble part.

7 Definitions and Formulas $$\text{Soluble Fraction } (w/w\ \%) = \frac{HA \text{ concentration in the permeate (mg/ml)}}{\text{total } HA \text{ concentration}} * 100$$

$$( = 4 \text{ mg/ml})$$

Number average molecular weight $M_n$: is the statistical average molecular weight of all the polymer chains in the sample, and is defined by:

$$Mn = \frac{\Sigma\ N_i M_i}{\Sigma\ N_i}$$

where $M_i$ is the molecular weight of a chain and Ni is the number of chains of that molecular weight. If $M_n$ is quoted for a molecular weight distribution, there are equal numbers of molecules on either side of $M_n$ in the distribution Weight average molecular weight $M_w$: is defined by $$Mn = \frac{\Sigma\ N_i M_i^2}{\Sigma\ N_i M_i}$$

Compared to $M_n$, $M_w$ takes into account the molecular weight of a chain in determining contributions to the molecular weight average. The more massive the chain, the more the chain contributes to Mw. If $M_w$ is quoted for a molecular weight distribution, there is an equal weight of molecules on either side of $M_w$ in the distribution For all synthetic polydisperse polymers: $M_n < M_w$ The polydispersity index is used as a measure of the broadness of a molecular weight distribution of a polymer, and is defined by:

$$\text{Polydispersity index} = \frac{Mw}{M_n}$$

The larger the polydispersity index, the broader the molecular weight. A monodisperse polymer where all the chain lengths are equal (such as a protein) has an $M_w/M_n = 1$. The best controlled synthetic polymers (narrow polymers used for calibrations) have $M_w/M_n$ of 1.02 to 1.10. Step polymerization reactions typically yield values of $M_w/M_n$ of around 2.0, whereas chain reactions yield $M_w/M_n$ values between 1.5 and 20.

Intrinsic Viscosity: reflects the capability of a polymer in solution to enhance the viscosity of the solution.

Refractive index increment dn/dc: The refractive index increment applies to the sample under a specific condition. For example, temperature, laser wavelength, conformation of the molecule, or additives influence the absolute value of dn/dc. Thus, for a perfect static light scattering experiment the exact dn/dc at the conditions under consideration should be determined. In many practical examples, the value can be taken from prior datasets taken under similar conditions (or from literature references).

Hydrodynamic radius $R_h$: as measured by dynamic light scattering, is defined as the radius of an equivalent hard sphere diffusing at the same rate as the molecule under observation. In reality, solutions of proteins and their complexes do not exist as hard spheres and so, the determined hydrodynamic radius more closely reflects the apparent size adopted by the solvated, tumbling molecule.

Mark-Houwink-Sakurada relation MHS: empirical relationship that works well for correlating intrinsic viscosities and molecular weights of fractionated samples. It is used for completing a conformational analysis of a given polymer.

Complex Viscosity: Complex shear Modulus. The overall resistance to deformation of a material, regardless of whether that deformation is recoverable (elastic) or non-recoverable (viscous). Symbol G* complex viscosity=viscosity−i×elasticity Share Modulus: (resulting from changing strain) is the ratio of the shear stress to the shear strain. It follows from the complex relationship similar to the above that:

$$G^* = G' + iG''$$

where
G* is the complex shear modulus,
G' is the in-phase storage modulus and
G'' is the out-of-phase similarly-directed loss modulus;
$G^* = \sqrt{(G'^2 + G''^2)}$ Crossover frequency: The frequency where these parameters cross over corresponds to a relaxation time (T) specific for the material.

Tan Delta: $\tan(\delta) = G''/G'$ quantifies the balance between energy loss and storage. As $\tan(45°)=1$, a value for $\tan(\delta)$ greater than unity indicates more "liquid" properties, whereas one lower than unity means more "solid" properties, regardless of the viscosity.

Swelling degree: Extent of swelling in polymers that can be determined via changes in linear dimensions or through volumetric changes. Most polymers swell by solvent (including water) absorption (hydration)

Example 1C: Summary of Syntheses of Cross-Linked Hyaluronic Acid (XLHA)

6. Introduction/Scope of the Report

The following reports summarises the different syntheses performed for the production of cross-linked Hyaluronic acid (XLHA).

7. Material and Methods

All the reagents have been used without no further purification. HTL HA fibers with a MW of 1550 kDa were used. BDDE (1 4-butanediol diglycidyl ether) and NaOH in pellets were purchased from Sigma Aldrich. HCl 1 N was purchased from Carl Roth International. All the mixtures and solutions were prepared using PBS the same used for the purification process.

Syntheses were performed using a three-neck round bottom flask (or a two neck round bottom flask for the three liter synthesis) equipped with a Teflon stirring blade connected to a mechanical stirrer (see diagram of flasks hereinbelow). Temperature was controlled by dipping the flask into a water bath placed over a heating plate. The temperature of the water and the gel have been both controlled during the heating steps and a flux of air guaranteed until the end of the crosslinking step.

As general procedure for all the batches fibers/powders were introduced inside the vessel/flask followed by a solution of NaOH in PBS (0.25M). The mixture was stirred for about 2 hours at room temperature until homogenization was completed. A solution of BDDE (ratio HA:BDDE 1:453) in PBS was then introduced, and the reaction mixture stirred at 50° C. for 2 hours to allow a faster cross-linking (this step has been performed assuring a continuous flux of air into the synthesis). HCl (0.08M) is then added to neutralize the pH and stop the cross-linking while stirring at a temperature of 4° C. overnight. A non-crosslinked gel is added and the mixture left stirring for 3 hours until complete homogenization.

The so obtained mixture was filtered under vacuum (280 µm mesh) and purified by dialysis using membranes with a molecular weight cut-off of 12-14 kDa for 24 hours (unless specified otherwise).

All the batches were controlled for pH, Osmolarity and viscosity. No analysis for the calculation of the residual quantity of BDDE as it was already assessed that after sterilization the value is lower than 0.82 ppm (5A-DIR 011 PV 26.01.2018) regardless of the value before sterilization.

8. Synthesis 3.1 Batch 12B18-D 60 g of HA (MW 2800 kDa) have been dissolved in 576.18 g of NaOH 0.25 M (PBS solution) and mixed for 2 hours and 45 minutes until the formation of a homogeneous gel. In the meanwhile, 5.45 g of BDDE have been diluted in 1.17 g of NaOH 0.25 M then added to the HA gel. The gel has been mixed for 30 minutes at room temperature. Then left at 48° C. for 1 hour and 34 minutes. The temperature was then lowered by the addition of 1764.86 g of HCl solution 1N and the neutralization started. The gel was left mixing at 5° C. for 17 hours and 47 minutes. In the same time 6.23 g of HA were dissolved in 300 g of NaOH 0.25M (PBS solution) then 269.07 g of the formed gel, was added to the neutralized XLHA. The mixture was left stirring for 2 hours. The obtained gel was purified during 24 hours by dialysis (membrane MW cut off of 12-14 kDa).

3.2 Batch 26C18-D 20 g of HA (MW 1550 kDa) have been dissolved in 192. 27 g of NaOH 0.25 M (PBS solution) and mixed for 2 hours and 20 minutes until the formation of a homogeneous gel. In the meanwhile, 1.11 g of BDDE have been diluted in 3.71 g of NaOH 0.25 M then added to the HA gel. The gel has been mixed for 40 minutes at room temperature. Then left between 41° C. and 50° C. for 70 minutes. The temperature was then lowered by the addition of 588.39 g of HCl solution 1 N and the neutralization started. The gel was left mixing at 5° C. for 16 hours and 45 minutes. In the same time 3.39 g of HA were dissolved in 150 g of NaOH 0.25M (PBS solution) then 89.64 g of the formed gel, was added to the neutralized XLHA. The mixture was left stirring for 3 hours and 40 minutes. The obtained gel was purified during 24 hours by dialysis (membrane MW cut off of 25 kDa).
3.3 Batch 10D18-D 20 g of HA (MW 1550 kDa) have been dissolved in 192.45 g of NaOH 0.25 M (PBS solution) and mixed for 2 hours until the formation of a homogeneous gel. In the meanwhile, 1.13 g of BDDE have been diluted in 3.70 g of NaOH 0.25 M then added to the HA gel. The gel has been mixed for 20 minutes at room temperature. Then left at 50° C. for 55 minutes. The temperature was then lowered by the addition of 588.18 g of HCl solution 1 N and the neutralization started. The gel was left mixing at 5° C. for 16 hours and 45 minutes. In the same time 3.39 g of HA were dissolved in 150 g of NaOH 0.25M (PBS solution) then 89.55 g of the formed gel, was added to the neutralized XLHA. The mixture was left stirring for 4 hours. The obtained gel was purified during 24 hours by dialysis (membrane MW cut off of 25 kDa).

Example 2—Cell Culture

Using the medical devices (containers) for the preparation of PRP/BMC for cell culture according to the invention, the following results have been obtained.

Figure 3:
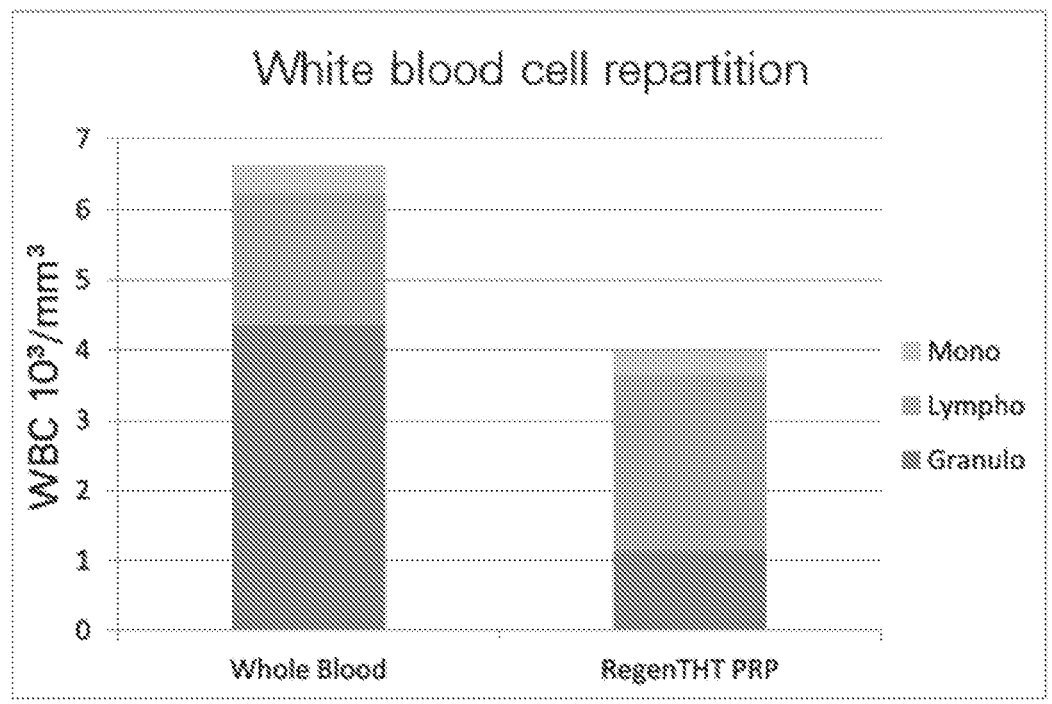
FIG. 3 shows a MC-PRP device which allows a preferential depletion (87%) of the pro-inflammatory granulocytes (Granulo). The remaining white blood cells that are concentrated together with PRP are mostly lymphocytes (Lympho) and monocytes(Mono).

See FIG. 3.

The main advantage of this device is demonstrated by its ability to sustain MNC (mononuclear cell) growth (evaluation made in vitro in MC-PRP kept at room temperature). Platelets kept in these conditions have similar half-life (7 days) as described in whole blood.

FIG. 4.

Example 3—Cell Culture—CC-S

Protocol for cell culture using CC-S
Phase 1: Collecting Whole
  blood
  1. Open the tube blister pack.
  Perform the venous puncture and fill the desired number of CC-S tubes with whole blood. The vacuum within the tubes will enable automatic collection of the necessary volume of blood (about 10 ml).
Phase 2: Centrifugation
  2. It is essential to always correctly balance the centrifuge before starting it.
  Once the blood is collected in the CC-S tubes, fill if necessary a counterbalance tube (supplied separately ref. SF-82—CB-110) with water until it reaches the same volume as the blood in CC-S tube it will counterbalance.
  Insert the filled tubes into the centrifuge facing each other to balance the machine.
  Adjust the centrifugation values as follows:
    Time: 10 to 20 minutes
    Centrifugal force (RCF): 1500 g (set corresponding RPM speed according to the centrifuge
    manufacturer's instructions)
Phase 3: Centrifugation Results
  3. After centrifugation, the blood is fractionated; the red and white blood cells are trapped under the gel and a fibrin clot is over the cell selector gel. The liquid part of the clot is the autologous thrombin serum. The serum is extracted from the clot either by extending the centrifugation time or by pressing on the clot with a cannula fitted on the collection syringe. About 4.5 ml of serum will be obtained from each tube.

Phase 4: Utilization
  4. CC-S is used as an autologous culture supplement at a concentration between 5 to 20% v/v, to be determined for each cell lines.

Example 4—Cell Culture—CC-PRP

Protocol for cell culture using
CC-PRP Phase 1: Collecting whole
  blood
  1a. Open the tube blister pack.
  Perform the venous whole blood, umbilical cord blood or medullar blood puncture
  puncture and fill the desired number of CC-PRP tubes. The vacuum within the tubes will enable automatic collection of the necessary volume of blood (about 10 ml).
  1b. Carefully turn the tubes upside down several times to mix the blood with the anticoagulant.
Phase 2: Centrifugation
  2. It is essential to always correctly balance the centrifuge before starting it.
  Once the blood is collected in the CC-PRP tubes, fill if necessary a counterbalance tube (supplied separately ref. SF-82—CB-110) with water until it reaches the same volume as the blood in CC-PRP tube it will counterbalance.
  Insert the filled tubes into the centrifuge facing each other to balance the machine.
  Adjust the centrifugation values as follows:
    Time: 5 minutes
    Centrifugal force (RCF): 1500 g (set corresponding RPM speed according to the centrifuge manufacturer's instructions)
Phase 3: Centrifugation Results
  3. After centrifugation, the blood is fractionated; the red and white blood cells are trapped under the gel, and platelets settle on the surface of the gel.
Phase 4: Homogenisation
  4. By gently inverting CC-PRP tube several times, proceed to the re-suspension of the platelet deposit in the plasma supernatant. About 5 ml of PRP will be obtained from each tube.
  Make sure that the platelets are fully detached from the gel. From clear and transparent plasma should become turbid. If platelet aggregates are present, they should be collected with the plasma.
Phase 5: Utilization
  3. CC-PRP is used as an autologous culture supplement at a concentration between 5 to 20% v/v, to be determined for each cell lines. To avoid fibrin clot formation the culture media should be supplement with 2 units/ml of heparin.

Example 5—Cell Culture—MC-PRP

Protocol for cell culture using
MC-PRP Phase 1: Collecting whole
  blood
  1a. Open the tube blister pack. Perform the venous puncture and fill the desired number of MC-PRP tubes with whole blood. The vacuum within the tubes will enable automatic collection of the necessary volume of blood (about 10 ml).
  1b. Carefully turn the tubes upside down several times to mix the blood with the anticoagulant.
Phase 2: Centrifugation
  2. It is essential to always correctly balance the centrifuge before starting it.
  Once the blood is collected in the MC-PRP tubes, fill if necessary a counterbalance tube (supplied separately) with water until it reaches the same volume as the blood in CC-PRP tube it will counterbalance.

Insert the filled tubes into the centrifuge facing each other to balance the machine.

Adjust the centrifugation values as follows:
Time: 8 minutes
Centrifugal force (RCF): 1500 g (set corresponding RPM speed according to the centrifuge manufacturer's instructions)

Phase 3: Centrifugation Results

3. After centrifugation, the blood is fractionated; the red and white blood cells are trapped under the gel, and the mononuclear cells and platelets settle on the surface of the gel.

Phase 4: Homogenisation

4a—method 1: By gently inverting the MC-PRP tube several times, proceed to the re-suspension of the cellular deposit in the supernatant. About 5 ml of cell suspension will be obtained for each tube.

4b—method 2: In order to obtain a higher cellular concentration: Before proceeding to the cell re-suspension delicately remove 2 ml of the upper layer of the acellular plasma supernatant with a long cannula (not supplied). Then re-suspend the cellular deposit in the remaining 2 ml by gentle inversions of the tube.

Make sure that the cells are fully detached from the gel. From clear and transparent the plasma should become turbid. If aggregates are present, they should be collected with the plasma.

Phase 5: Utilization

5. MC-PRP typically yields a cell suspension in platelet rich plasma with 70+/-10% recovery of the mononuclear cells present in the original sample.

Example 6—Cell Culture with CC-HA

Protocol for cell culture using
CC-HA Phase 1: Collecting whole
blood

1a. Open the first blister pack, then the second with care.

1b. Perform the venous puncture using the necessary phlebotomy material from Accessory Set and fill the CC-HA tubes with whole blood. The vacuum within the tubes will enable automatic collection of the necessary volume of blood (about 6 ml).

1c. Carefully turn the tubes upside down several times.

1d. Discard withdrawal needle using the adequate method for elimination of contaminated blood products.

Phase 2: Centrifugation

It is essential to correctly balance the centrifuge before starting it. If necessary, fill the counterbalance tube (supplied separately) with water until it reaches the same level as the blood in the CC-HA tube. Then, insert the filled tubes into the centrifuge facing each other to balance the machine.

Adjust the centrifugation values as follows:
Time: 5 minutes
Centrifugal force (RCF): 1500 g
(set RPM speed according to the centrifuge manufacturer's instructions)

Phase 3: Centrifugation Results

After centrifugation, the blood is fractionated: the red blood cells are trapped under the gel, and cellular elements settle on the surface of the gel. Hyaluronic acid is positioned over the plasma.

Phase 4: Homogenization

4a. Hold the tube upside down in a vertical position and maintain it in this position until the HA detaches from the tube walls and floats to the top of the plasma layer.

4b. Carefully invert the tube at least 20 times until the platelets are resuspended.

4c. Roll the tube between fingers in a horizontal position until all the HA has been removed from tube walls and the preparation is homogeneous. About 5 ml of mix HA/PRP will be obtained for each tube.

4d. Use the Transfer Device, from Accessory Set, for collection of the mix HA/PRP from CC-HA tube.

Phase 5: Utilization

5. CC-HA may be used as an autologous culture supplement at a concentration between 10 to 40% v/v, to be determined for each cell lines. To avoid fibrin clot formation the culture media should be supplement with 2 units/ml of heparin. In this preparation, platelets are trapped in the hyaluronic acid matrix. This preparation can be used as a coating matrix for monolayer cultures to be determined for each cell line.

Example 7—Efficacy of CC-PRP Devices

Figure 5:
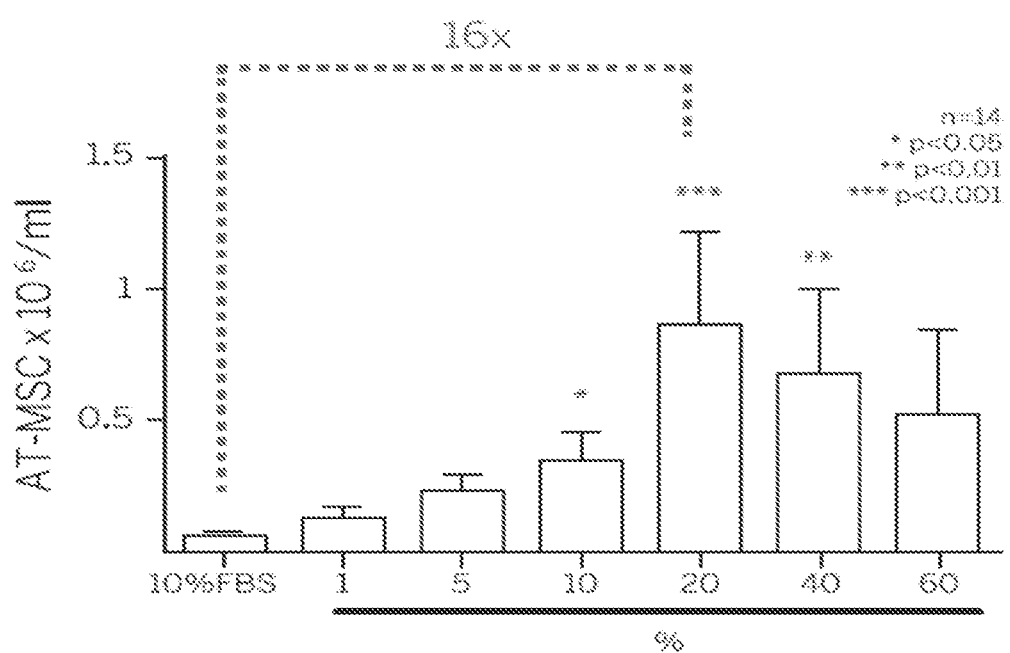
FIG. 5 shows AT-MSC culture supplements prepared from the patient's own blood drastically enhances in vitro proliferation in comparison to the classical culture medium prepared with 10% FBS.
Figure 6A:
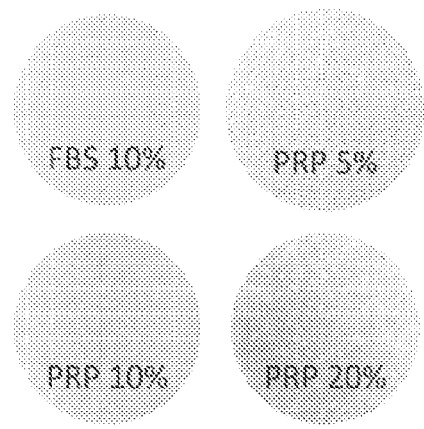
FIGS. 6(A) through 6(C) shows PRP proliferative effect on NHDF from the same patient, as shown in FIG. 6(A). NHDF were isolated by enzymatic digestion from a fresh skin sample and seeded for in vitro cultures at the same density. After 5 days of culture, increasing concentrations of PRP significantly enhance cell proliferation (optic microscopy pictures), as shown in FIG. 6(B). Flow cytometry analysis of cell proliferation after violet dye incorporation. Results are expressed in fold induction, as shown in FIG. 6(C). Representative density plots of the data plotted in the B Graph.
Figure 6B:
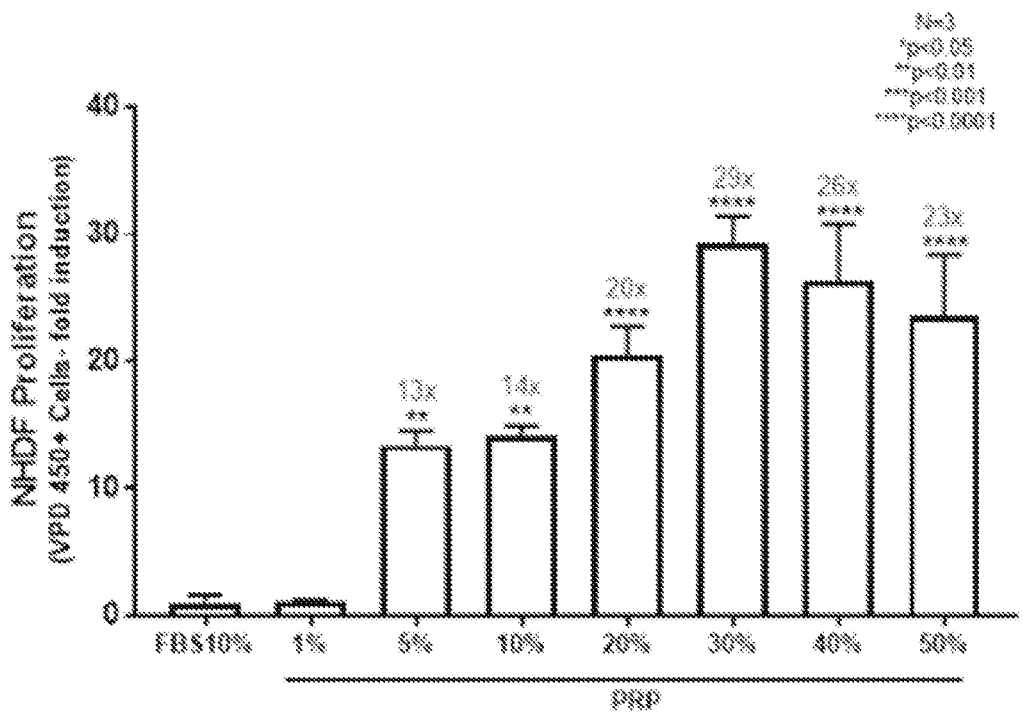
Figure 6C:
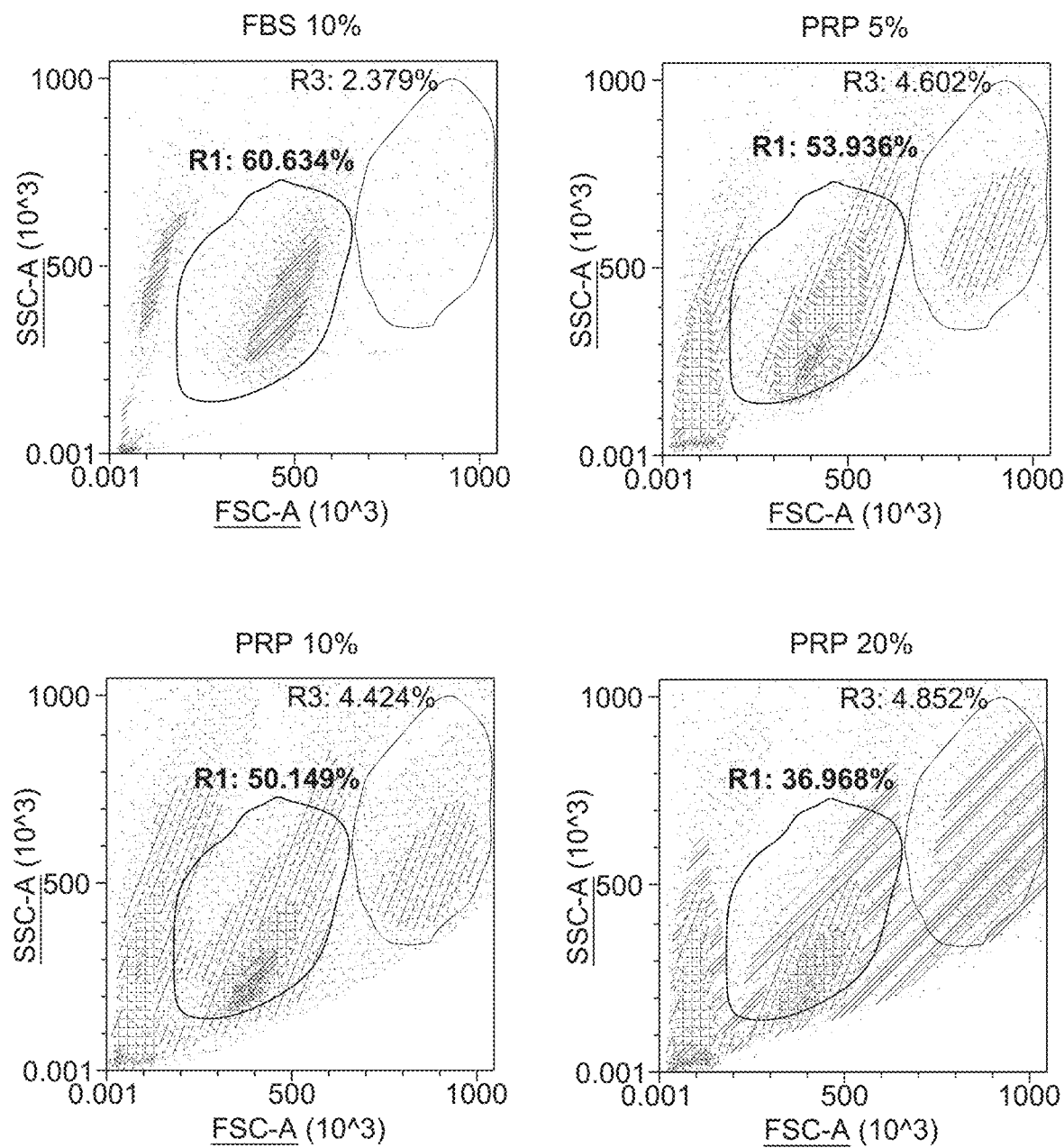

We demonstrate in this example the great effectiveness of using PRP in cell culture using devices of the invention in comparison to classic culture conditions for AT-MSC (Adipose-tissue derived mesenchymal stem cells, and NHDF (normal human dermal fibroblast) (FIGS. 5 and 6).

1. AT-MSCs
AT-MSC
isolation

Pure fat was digested with 0.01% collagenase type I (Sigma-Aldrich, St. Louis, MO) for 45 min at 37° C. with gentle agitation. The nondigested adipose tissue was removed after centrifugation at 1400 rpm for 10 min. The remaining pellet, called the stromal vascular fraction (SVF), was suspended in erythrocyte lysis buffer for 5 min (Qiagen, Hilden, Germany). It was then washed with the basal medium: Dulbecco's modified Eagle's medium (DMEM)-low glucose containing 1 g/L glucose, 1-glutamine, 25 mM HEPES (Invitrogen, Carlsbad, CA), supplemented with penicillin and streptomycin 10,000 mg/mL (Bioconcept, Salem, NH), and 2 units/mL heparin (Liquemin 5000; Roche, Basel, Switzerland).

After centrifugation at 1200 rpm for 5 min, SVF was then resuspended in DMEM and supplements, and filtered through a 100 mm nylon cell strainer (BD Biosciences). The mean cell density in the isolated SVF was $30 \times 10^4$ cells/mL.

AT-MSC Culture

SVF cells were plated at 5000 cell/cm2 in a 48-well plate (BD Biosciences) and cultured in different media culture conditions: 10% FBS (Gibco, Carlsbad, CA) as control or 1%, 5%, 10%, 20%, 40%, and 60% of either nPRP or tPRP added to the basal DMEM and supplements (1 mL medium for each condition). The resulting plastic-adherent cell population after 24-48 h of culture was determined as AT-MSCs. Cells were cultivated at 37° C. for 10 days in a standard incubator with 5% CO2 without changing the culture media for FBS and PRP conditions.

PRP Proliferative Effect on AT-MSC

In all conditions, AT-MSCs kept their typical spindle fibroblast shape during the culture period. After 10 days culture, all media supplemented with different nPRP concentrations presented a higher AT-MSC number when compared to FBS-containing media (FIG. 3). This positive effect of nPRP followed a dose-dependent bell-shape curve. Media supplemented with 20% nPRP offered the optimal condition, with AT-MSC number being 13.9 times higher than in 10% FBS (n=14, p<0.001) after 10 days of culture. In comparison, other conditions were less effective [e.g., 10% and 40% nPRP media increased respectively 5.6 and 10.9 times the AT-MSC number when compared to 10% FBS (n=14, p<0.001)](FIG. 3).

FIG. 5

2. NHDF

NHDF isolation

Briefly, tissue harvested during an abdominoplasty underwent a 14 unit/mL Liberase DL Research grade (Roche) digestion, which was used to isolate epidermal versus dermal layers that were processed separately. NHDFs were isolated through mincing and subsequent digestion in 0.3% Trypsin/PBS collagenase (Gibco) with 1% Fetal Bovine Serum (FBS, Gibco) and 1% Antibiotics/Antimycotics (AB/AM, Gibco). NHDFs were then filtered, centrifuged, and plated. NHDFs exhibit expected cobblestone and spindle morphology, respectively, and no signs of contamination. NHDF cells, passage 1 through 5, were cultured in Dulbecco modified Essential Media (DMEM, Gibco) containing 10% FBS and 1% P/S at 37° C. supplemented with 5% CO2. All cells were grown to 80% confluency and passaged using TrypleX solution (Gibco).

NHDF Culture

NHDF were plated at 1000 cell/cm$^2$ in a 12-well plate (BD Biosciences) and cultured in different media culture conditions: 10% FBS (Gibco, Carlsbad, CA) as control or 1%, 5%, 10%, 20%, non activated PRP. Cells were cultivated at 37° C. for 5 or 7 days in a standard incubator with 5% CO2 without changing the culture media for FBS and PRP conditions.

PRP Proliferative Effect on NHDF

Figure 4:
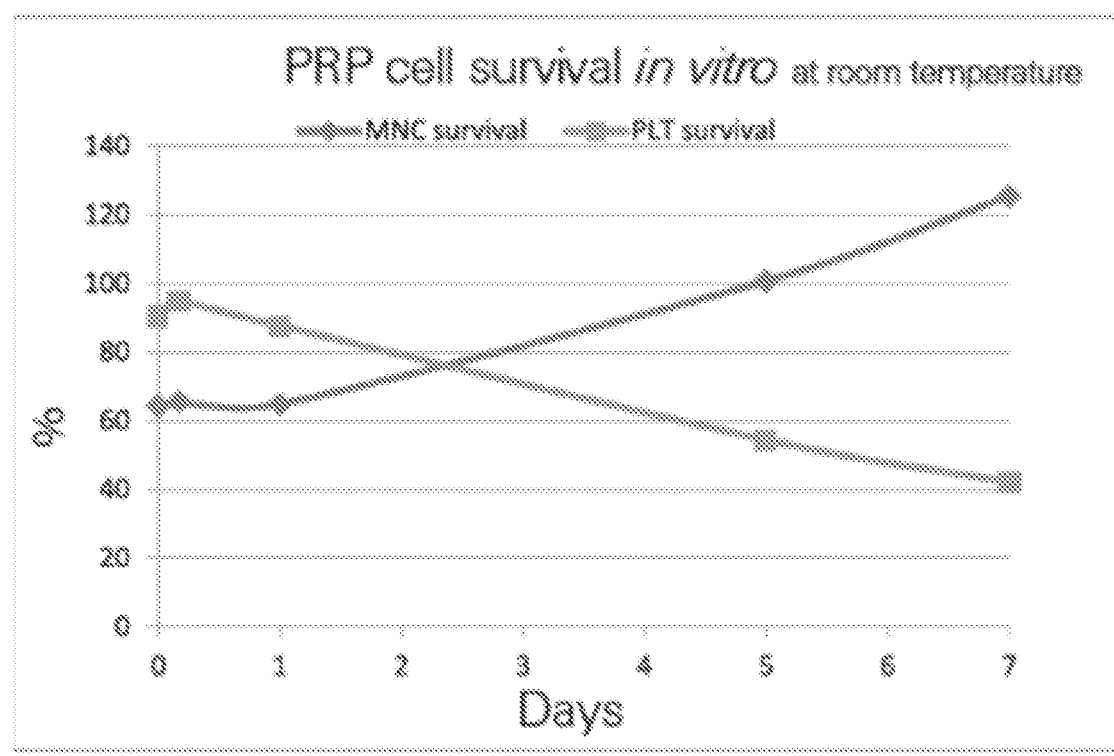
FIG. 4 shows a MC-PRP device which allows a sustained MNC viability thanks to the presence of the platelets presents in the plasma that act as a reservoir for a sustained release of nutrients and growth factors.

In all conditions, NHDF kept their typical spindle fibroblast shape during the culture period. After 5 days culture, all media supplemented with different nPRP concentrations presented a higher NHDF number when compared to FBS-containing media (FIG. 4. Media supplemented with 20% nPRP offered the optimal condition, with NHDF number being almost 4 times higher than in 10% FBS (n=3, p<0.001) after 5 days of culture. After 7 days, the PRP proliferative effect at 20% is even more effective by increasing up to 5-6-fold the total cell number, with half of the cells showing a high proliferative phenotype as depicted by the flow cytometry analysis.

FIG. 6.

Example 8—Cellular characterization of CC devices products and study of their potential for culture of PBMC, MSC, and chondrocytes I. Introduction Three devices according to the invention are tested:

MC-PRP: Allows the isolation of mononuclear cells from peripheral blood, umbilical cord blood and bone marrow aspiration CC-PRP: Allows the preparation of Platelet Rich Plasma (PRP), which can be used, pure or as an additive, in a synthetic culture medium, replacing a serum of animal origin to promote cell growth in-vitro CC-S: allows to obtain a serum, which can be used as an additive in the synthetic culture medium to promote cell culture in-vitro to replace a serum of animal origin The products corresponding to the preparations resulting from these devices are called respectively "MC-PRP preparation", "CC-PRP preparation" and "CC-S preparation".

These preparations are produced in liquid or gel form for biological coating, with applications in orthopedics and dermatology. It should be noted that the use of CC-PRP and MC-PRP in a synthetic culture medium may require the addition of an anticoagulant, e.g. heparin (2 units/ml) to prevent coagulation of the plasma.

The study aims on the one hand to characterize the cell populations present within the 3 preparations and on the other hand to evaluate the potential of the CC-PRP and CC-S preparations in cell culture on several types of cells.

II. Objectives and Services

II.1. Phenotypic Characterization and Cell Survival

This study aims to:

Carry out a fine phenotypic characterization of the cell subpopulations present in the MC-PRP preparation by flow cytometry (Fortessa LSRII, BD Biosciences)

Perform B, T, NK cell and granulocyte counts by 6-color flow cytometry for CC-PRP and CC-S devices To study the survival of cells from MC-PRP, CC-PRP and CC-S devices after they have been cultured II.1.a Fine Phenotypic Characterization of the Cell Populations Present in the MC-PRP Preparation The fine phenotypic analysis of immune subpopulations includes:

ACD3+T lymphocyte count, CD19+Blymphocytes, CD3—CD16+CD56+NK lymphocytes

A count and an analysis of the frequency of the 3 monocytic subpopulations present in the blood: inflammatory monocytes CD14+, intermediate monocytes CD14+CD16+ and non-classical monocytes CD16+

A count of the 3 subpopulations of dendritic cells present in the blood: DC myeloid: mDC1 CD1c+; mDC2 CD141+as well as plasmacytoid DC CD123+

Numeration and analysis of the subpopulation frequency of NK lymphocytes (CD56−, CD56dim and CD56bright)

An enumeration and analysis of the frequency of TCD4 and CD8 lymphocyte subpopulations (naive, central memory, CD45RA− effectors and CD45RA+memory effectors)

A count and analysis of the subpopulation frequency of T helper lymphocytes (Th1 CXCR3+, Th2 CCR4+, Th17/Th22 CCR6+CCR4+, and TFH subpopulations CXCR5+)

A count and analysis of the frequency of sub-populations of T regulators (naive CD45RA+, memories CD45RA-FoxP3low, effectors CD45RA-FoxP3high and activated HLA-DR+)

A count and analysis of the frequency of B lymphocyte subpopulations (naive CD27−IgD+, non-switched CD27+IgD+memory, CD27+IgD−, CD27−IgD−, CD27−

IgD−, double negative CD24highCD38high immature/transitional CD27, CD27 plasmablasts+CD38+CD138− and CD27+CD38+CD138+plasma cells)

The phenotype of the cells obtained by the MC-PRP device will be compared to that of peripheral blood mononuclear cells (PBMC) isolated after Ficoll gradient centrifugation on the same donor. There will therefore be 2 conditions after Ficoll: condition "MC-PRP" and "CC-PBMC". It will be necessary for these two conditions to proceed to a prior step of unpacking and counting PBMCs prior to phenotyping.

The phenotypic characterization will be broken down into 8 tubes of 6 to 15 antibodies for each of the two conditions:
- tube 1: numbering of the lineages LB, LT and NK which serves as reference
- tube 2: characterization of the 3 monocyte subpopulations: classical, intermediate and unconventional.
- tube 3: analysis of LT differentiation which allows to characterize the naive CD4 and CD8 populations, central memories, memory effector and EMRA using the differential expression of markers CD45RA and CCR7.
- tube 4: analysis of subpopulations of dendritic cells (DC myeloid CD141+ and CD1c+) and DC plasmacytoid. The level of DC activation will be analyzed by the level of expression of HLA-DR molecules and co-stimulatory molecules.
- tube5: helper T cell analysis which makes it possible to determine the frequency of Th1 (CXCR3+), Th2 (CCR4+), Th17/22 (CCR6+, CCR4+), Th1/Th17 (CXCR3+, CCR6+) and follicular T cells (CXCR5+).
- tube 6: characterization of NK subpopulations based on differential expression of CD16 and CD56 markers.
- tube 7: analysis of regulatory LT subpopulations based on expression of CD45RA and FoxP3 markers. Activation will be characterized by the expression of HLA-DR, CD39, CD62L and CTLA-4 molecules.
- tube 8: analysis of LB subpopulations to characterize naïve B cells, non-switched memories, memory-switched based on the relative expression of CD27 and IgD. The plasma cells and transitional B will also be characterized.

A minimum of 10 to 12 ml of donor blood will be required for this study.

II.1.b Phenotypic Characterization of Cells in CC-PRP and CC-S Preparations For CC-PRP and CC-S devices: count of B cells, T cells and NK cells by 6-color flow cytometry.

It will be necessary to proceed for both conditions (MC-PRP and CC-S) to a preliminary step of unpacking and counting the mononuclear cells present in these samples before phenotyping. The phenotypic characterization will include a tube for each of the two conditions: LB, LT and NK (6 antibodies+viability marker+counting beads).

A minimum of 10 ml of donor blood will be required for this study for a cell contamination assumption of the order of 1%.

OPTION: Determination of growth factors in the serum obtained using the CC-S device versus autologous serum obtained on a dry tube.

ELISA assay of the following growth factors: TGF-β1, TGF-β2, PDGF-BB, PDGF-AB, VEGF, FGF basic, IGF-I and human EGF in CC-S versus an autologous serum obtained on a dry tube. A panel of 10 donors will be used to carry out a statistical study.

II.1.c Cell Survival after Culturing Cells from Preparations MC-PRP, CC-PRP and CC-S A count of mononuclear cells, platelets, and granulocytes will be performed before culturing. This count will define the amount of blood needed for this study. Moreover, a count, an evaluation of the cell viability and a characterization by flow cytometry (3 tubes for the counting of B lymphocytes, T lymphocytes, myeloid cells and granulocytes) will be performed after 24 hours and 48 hours of culture.

If cell survival is greater than 70% after 48 h of culture, we will achieve two additional points at 72 h and 96 h, also including count, cell viability assessment, and 6-colorflow cytometric characterization.

Preliminary results showed a 6-day doubling time for MNCs kept at room temperature in the PRP.

II.2. Evaluation of CC-PRP and CC-S Preparations on Cell Survival

The purpose of the study is to evaluate the effect of the PRP preparation on the culture of several types of cells:
- Human peripheral blood mononuclear cells (PBMCs)
- Human Mesenchymal Stem Cells (MSC)
- Human chondrocytes II.2.a. PBMC Evaluation of the effect of CC-PRP and CC-S preparations on PBMC culture by complete immunophenotyping at 48 h in order to demonstrate a preferential survival of certain cell subpopulations. This would consist of:
- a phenotypic characterization of all lymphoid and myeloid populations before culturing (J0) in flow cytometry allowing the analysis of myeloid cells, NK cells, regulatory T cells, helper T lymphocytes, memory T cells and B lymphocytes;
- a phenotypic characterization of all lymphoid and myeloid populations after 48 h of culture in flow cytometry allowing analysis of myeloid cells, NK cells, regulatory T cells, helper T lymphocytes, memory T cells and lymphocytes B.

The work will be done autologous. Four conditions will be tested:
- Autologous serum obtained from blood collected on a dry tube (used at 10% in the culture medium)
- CC-S (used at 10% in the culture medium)
- Autologous serum obtained from blood collected on a dry tube (used at 10%+Heparin 2 U/ml). (control to overcome the effect of heparin on the cell phenotype)
- CC-PRP (used at 10%+heparin 2 U/ml)

The fine phenotypic characterization of all lymphoid and myeloid populations before culture (J0-1 point) by flow cytometry will comprise 8 tubes:
- tube 1: counting of LB, LT and NK (6 antibodies+viability marker+counting beads). Marked on 0.5 $10^6$ of PBMCs/tube
- tube 2: analysis of monocyte subpopulations (13 Antibody+viability marker+counting beads). Marked on 2 $10^6$ of PBMCs/tube
- tube 3: analysis of LT differentiation (11 antibodies+viability marker). Marked on 1 $10^6$ of PBMCs/tube
- tube 4: analysis of subpopulations of dendritic cells (17 antibodies+viability marker+numbering of beads). Marked on 2 $10^6$ of PBMCs/tube
- tube 5: T helper cell analysis (12 Antibody+viability marker). Marked on 2 $10^6$ of PBMCs/tube
- tube 6: analysis of NK subpopulations (14 antibodies+viability marker). Marked on 1 $10^6$ of PBMCs/tube
- tube 7: analysis of regulatory LTs (Antibodies+viability marker). Marked on 1 $10^6$ of PBMCs/tube
- tube 8: analysis of subpopulations of LB (13 Antibody+DAPI). Marked on 2 $10^6$ of PBMCs/tube The fine phenotypic characterization of all lymphoid and myeloid populations after culture (48 h, 4 points) by flow cytometry will include 4×8 tubes:
- tubes 1-4: LB, LT and NK count (6 Antibodies+viability marker+counting beads). Marked on 0.5 $10^6$ of PBMCs/tube tubes 5-8: analysis of monocyte subpopulations (13 antibodies+viability marker+counting beads). Marked on 2 $10^6$ of PBMCs/tube tubes 9-12: analysis of LT differentiation (11 antibodies+viability marker). Marked on 1 $10^6$ of PBMCs/tube tubes 13-16: analysis of subpopulations of dendritic cells (17 antibodies+viability marker+beads numbering). Marked on 2 $10^6$ of PBMCs/tube tubes 17-20: T helper cell analysis (12 antibodies+viability marker). Marked on 2 $10^6$ of PBMCs/tube tubes 21-24: analysis of NK subpopulations (14 antibodies+viability marker). Marked on 1 $10^6$ of PBMCs/tube tubes 25-28: analysis of regulatory LTs (15 antibodies+viability marker). Marked on 1 $10^6$ of PBMCs/tube tubes 29-32: analysis of subpopulations of LB (13 antibodies+DAPI). Labeling carried out on $2\times10^6$ of PBMCs/tube (helperT lymphocytes, memory T lymphocytes, B lymphocytes).

Instead of 48 hours or in addition to, testing at a later stage may be conducted.

II.2.b. Human CSM

Study—fresh blood may be used:
to evaluate the effect of CC-PRP and CC-S preparations on the survival and proliferation of mesenchymal stem cells (MSCs) in culture, compared with fetal calf serum (positive control);
to study the differentiation properties of MSCs to three lineages: chondrocytes, adipocytes and osteoblasts.

The first step in the study will be to determine the effective dose of CC-PRP and CC-S (0, 5, 10, 15, 20 or 25%) to be used in culture for optimal survival and proliferation of MSCs. on 3 passages. Once these doses are determined, a comparative MSC survival and proliferation study will be conducted between a positive control medium containing fetal calf serum conventionally used, and a medium containing either CC-PRP or CC-S at optimal doses. This study will be carried out on at least 2 different samples of CSM and 4 passages. The survival and proliferation of MSCs will be determined by trypan blue counting at each pass.

The study of the differentiation properties of the MSCs in the three lineages (chondrocytes, adipocytes and osteoblasts) will be carried out by culturing the cells over 21 days in specific differentiation media in comparison with the reference medium.

In the case of chondrocyte differentiation, the differentiation efficiency is evaluated on the one hand by comparing the differentiated cells at 21 days compared to the undifferentiated cells on day 0 and, on the other hand, by comparing the cultured cells in the presence or not of an inducing factor of the chondrocyte differentiation of MSCs, TGFB3. Thus, 7 conditions will be required to evaluate the effect of CC-PRP and CC-S on chondrocyte differentiation:

CSM J0
CSM+positive control J21
CSM+positive control+TGFb3 J21
CSM+CC-PRP J21
CSM+CC-PRP+TGFb3 J21
CSM+CC-S J21
CSM+CC-S+TGFb3 J21

A fibroblastic marker may be required at the end of culture to ensure that cells have not transdifferentiated.

For differentiation into adipocytes, the differentiation efficiency will be evaluated by comparing the cells cultured for 21 days, either in the differentiation medium or in the proliferation medium. Thus, 6 conditions will be required to evaluate the effect of CC-PRP and Serum on adipocyte differentiation:

CSM+Positive Control J21, Proliferation Medium
CSM+positive control J21, differentiation medium
CSM+CC-PRP J21, proliferation medium
CSM+CC-PRP J21, differentiation medium
CSM+CC-S J21, proliferation medium
CSM+CC-S J21, middle of differentiation Differentiation will be determined by evaluating the induction of markers specific for each lineage by RT-qPCR (panel of 3 markers per differentiated cell) as well as by Red Oil staining for differentiation into adipocytes.

Finally, the same experimental scheme will be applied for differentiation into osteoblasts: the differentiation efficiency will be evaluated by comparing the cells cultured for 21 days, either in the differentiation medium or in the proliferation medium. Six conditions will be required to evaluate the effect of CC-PRP and Serum on differentiation into osteoblasts:

CSM+Positive Control J21, Proliferation Medium
CSM+positive control J21, differentiation medium
CSM+CC-PRP J21, proliferation medium
CSM+CC-PRP J21, differentiation medium
CSM+CC-S J21, proliferation medium
CSM+CC-S J21, middle of differentiation Differentiation will be determined by evaluating the induction of specific markers of each lineage by RT-qPCR (panel of 5 markers per differentiated cell) as well as by histological staining for differentiation into osteoblasts.

II.2.C. Human Chondrocytes

Preparations obtained with CC-PRP and CC-S tubes on the survival, proliferation and phenotype of human chondrocytes.

A first step will be to determine the effective dose of CC-PRP and CC-S (0, 5, 10, 15, 20 or 25%) to be used in culture to obtain optimal survival and proliferation of human chondrocytes on 2 passages. The survival and proliferation of MSCs will be determined by trypan blue counting at each pass. The effect of CC-PRP and CC-S on the maintenance of the chondrocyte phenotype in culture will be determined by RT-qPCR and compared with the results obtained after culturing the cells in a positive control medium containing FCS. The expression of specific markers of chondrocytes (aggrecan, collagen IIB, Sox9, Collagen X, MMP13) will be evaluated at passages 1 and 2. A fibroblastic marker may be required in the final characterization to evaluate the de-differentiation of chondrocytes.

II.2.d. Human Hepatocyte Cells

Effect of CC-PRP and/or CC-S preparations on the proliferation and maintenance of the differentiated state of human hepatocyte cells using two cellular models: HepG2 human hepatoma lines —C3A and HuH7, and primary cultures of adult human hepatocytes. It is important to note that the experiments will be performed in allogeneic.

1—Study of the Impact of PRP on the Survival and Proliferation of Hepatoma Line In a first series of experiments the toxicity of CC-PRP and CC-S solutions will be evaluated on HepG2—C3A and HuH7 cell lines. A large dose effect will be tested (5 to 25%). The effect of these solutions on proliferation will then be evaluated. A small number of doses will then be selected to analyze cell proliferation on several passages.

Experimental Protocol

Evaluation of toxicity

The cells will be cultured in 96-well plates in culture medium supplemented with 10% fetal calf serum (FCS).

After 16 hours of incubation the medium will be replaced by base medium supplemented with 5, 10, 15, 20, or 25% CC-PRP supplemented with 2 U/ml of heparin 5, 10, 15, 20, or 25% irradiated CC-PRP supplemented with 2 U/ml of heparin 5, 10, 15, 20, or 25% CC-S 2 U/ml of heparin 10% of FCS 10% FCS supplemented with 2 U/ml heparin After 48 hours of culture, cell viability will be measured using the Cell Titer-Glo Luminescent Viability Assay kit (Promega).

Evaluation of the proliferation on a passage

The cells will be cultured in 96-well plates in culture medium supplemented with 10% fetal calf serum (FCS).

After 16 hours of incubation the medium will be replaced by base medium supplemented with 5, 10, 15, 20, or 25% CC-PRP or Irradiated CC-PRP supplemented with 2 U/ml of heparin 5, 10, 15, 20, or 25% CC-S 2 U/ml of heparin 10% of FCS 10% FCS supplemented with 2 U/ml heparin After 24, 48 and 72 h of culture the proliferation will be evaluated by measuring the incorporation of BrdU (Cell Proliferation ELISA, BrdU-Sigma).

Evaluation of the proliferation on 3 passages

The cells will be cultured in 24-well plates in culture medium supplemented with 10% fetal calf serum (FCS).

After 16 hours of incubation the medium will be replaced by base medium supplemented with x %, y % CC-PRP or Irradiated CC-PRP supplemented with 2 U/ml heparin x %, y % CC-S 10% of FCS 10% FCS supplemented with 2 U/ml heparin Cells are counted at each pass and viability is measured in Trypan blue Each experimental point will be tested in triplica (duplica for counts on 3 passages). The results will be analyzed on the basis of 3 independent experiments (so with 3 different batches of CC-PRP, CC-S).

2—Study of the Impact of PRP on the Proliferation and Maintenance of the Differentiated State of Primary Human Hepatocytes Primary human hepatocytes will be cultured in a definite defined medium (Pichard L, Raulet E, Fabre G, Ferrini J B, Ourlin J C, Maurel Moleth P. Molods 2006, 320: 283-93) supplemented or not with CC-PRP. At the times indicated thereafter, the toxicity, the proliferation and the maintenance of the differentiated state will be analyzed. It should be noted that the experiments will be performed on 3 primary hepatocyte preparations with 3 different batches of CC-PRP.

NB: The results obtained on the hepatoma lines will be taken into account to adapt the percentages of CC-PRP used and to decide on the use of this irradiated solution or not.

Experimental Protocol

Evaluation of toxicity

The hepatocytes will be cultured in 96-well plates coated with collagen I in defined culture medium (Pichard et al., 2006) supplemented with 2% fetal calf serum (FCS).

After 16 hours of incubation the medium will be replaced by base medium supplemented with 5, 10, 15, 20, or 25% CC-PRP or Irradiated CC-PRP supplemented with 2 U/ml heparin 2 U/ml of heparin After 24 h and 96 h of culture, cell viability will be measured using the Cell Titer-Glo Luminescent Viability Assay kit (Promega).

Evaluation of proliferation by measurement of BrdU incorporation.

Hepatocytes are cultured in 96-well plates coated with collagen I in defined medium (Pichard et al., 2006) supplemented with 2% FCS After 16 hours of incubation, the medium will be replaced by base medium supplemented with:

5, 10, 15, 20, or 25% CC-PRP or Irradiated CC-PRP supplemented with 2 U/ml heparin 2 U/ml heparin 10 ng/ml EGF and HGF and 2 U/ml heparin Proliferation will be evaluated every 24 hours for 72 hours by measuring the incorporation of BrdU (Cell Proliferation ELISA, BrdU-Sigma).

Evaluation of the maintenance of the differentiated state of hepatocytes.

Hepatocytes are cultured in 24-well plates coated with collagen I in defined medium (Pichard et al., 2006) supplemented with 2% FCS After 16 hours of incubation the medium will be replaced by base medium supplemented with x % and y % CC-PRP or Irradiated CC-PRP supplemented with 2 U/ml heparin 2 U/ml heparin during approximately 48 hours.

The cells will then be incubated for 24 hours with 10 μM rifampicin or 10 nM TCDD (prototypical activators of the two main signaling pathways involved in the metabolism of xenobiotics)

The maintenance of the expression and inducibility of the xenobiotic metabolism enzymes will then be evaluated by measuring the expression of a battery of target genes of these signaling pathways by RT-qPCR (PXR, AhR, CYP3A4, CYP1A2 albumin, HNF4).

Option 1: Evaluation of ERK1/2 and Akt signaling pathways by western-blot after incubation of hepatocytes with two doses of CC-PRP or CC-PRP irradiated. EGF will be used in positive control.

Option 2: Measurement of CYP3A4 and CYP1A2 activity (Kits P450-Glo).

Option 3: Culture of primary hepatocytes in culture medium supplemented with CC-HA (enriched with hyaluronic acid) to promote the organization of hepatocytes into spheroids. It would also be interesting to test the impact of CC-PRP or CC-S on the formation of spheroids. Indeed, their formation depends on the presence of serum. In addition, the formation of spheroids is not effective on all lots of hepatocytes.

Experimental Protocol the hepatocytes are cultured in 96 well plates GravityTRAP® ULA plate in defined medium (Pichard et al., 2006) supplemented with:

10% SFV

10% CC-HA

10% CC-PRP

10% CC-S

The formation of spheroids will be observed under a microscope over a period of 7 days.

The viability of the hepatocytes in the spheroids will be evaluated by calcein-propidium iodide labeling.

Control of attachment of cells to collagen I in defined culture medium (Pichard et al. 2006) 2% FCS will be realized.

Each experimental point will be tested on 6 wells. The results will be analyzed on the basis of 5 independent experiments (thus with 5 different lots of CC-HA, CC-PRP, CC-S).

NB: The hepatocytes to be cultured directly in the test solutions, the experiments will be carried out, for logistical reasons, on cryopreserved hepatocytes.

The impact of the different solutions on the differentiation of hepatocytes into spheroids can be evaluated later. The relevance of this study will depend on the results obtained with the CC-PRP, CC-S solutions on the differentiation of hepatocytes in 2D on the one hand and their impact on the formation of spheroids on the other hand.

Example 9—Neural and Neural Stem Cells Applications to Alzheimer's Disease, Carole Crozet, Stem Cells and Neurodegenerative Diseases The first objective is to determine the effect of preparation of PRP and the different cell culture devices of the invention on the proliferation and differentiation of human neural stem cells (NSCs). We propose to use two neural stem cell lines: the H9NSC (Gibco) line derived from human embryonic stem cells or from an iPSC/NSC line derived from non-pathological iPSC.

The second objective is to evaluate the fate of NSC cells grafted and pretreated with PRP in healthy mice and experimental models of AD.

Finally, the last goal is to study the effect of PRP on NSC and neural networks obtained from iPSC reprogrammed from fibroblasts of patients with Alzheimer's disease (AD).

PRP and Neural Models

Many questions about the fate of neural stem cells and their neuronal derivatives after grafting as well as their differentiation are raised. Moreover, these cells can either be grown in the form of neurospheres or in monolayer. Problems of necrosis and spontaneous differentiation difficult to master are encountered in neurospheres; on the other hand, this type of culture does not require a matrix for cell adhesion, as is the case for monolayer cultures. Indeed, for monolayer cultures, the amplification of NSCs requires the use of culture dishes previously coated with matrigel, poly-ornithine+laminin or poly-ornithine+fibronectin which pose problems given their origin. The use of PRP as a matrix replacement for monolayer culture or trophic support for suspension cultures could then be considered.

Cellular Models

Use of H9NSC lines from human embryonic stem cells sold by GIBCO and NSCs obtained from healthy iPSCs that have been generated with different protocols for differentiating these cells: neuronal differentiation in monolayer (over 30 days), neuronal differentiation in 3D which makes it possible to obtain mature neurons (over 6 to 12 weeks). Modeling for Alzheimer's disease for 2 years has been made using iPSCs generated from fibroblasts of patients suffering from Alzheimer's disease. The characterization of the cells shows that the cells from patients have different phenotypes from the healthy controls: slower proliferation, higher apoptosis, ROS (Reactive oxygen species) generation and a higher Abeta42/40 ratio, consistent with the marks of the Alzheimer's disease. The aim is to test PRPs on iPSCs from patients with Alzheimer's disease, and to test the transplantation of healthy cells previously cultivated with Alzheimer's disease. PRP or co-injection with PRP in experimental models of Alzheimer's disease.

Experimental Plan

1—Determination of the Dose of PRP

The first step of the project will be to determine the appropriate dose of PRP to use for NSC culture, that is, the dose that does not lead to cell death. For this, we propose to test different doses of different PRP and to evaluate the survival and proliferation of cells on 1 passage compared to the use of our medium used in control.

Evaluation of toxicity/apoptosis: The toxicity of the PRP solution will be evaluated by measuring the release of LDH (CytoTox 96@Non-radioactive Cytotoxicity Assay—Promega) and apoptosis using the caspase-3/7 kit (Caspase-Glo® 3/7 Assay-Promega).

Proliferation Evaluation: Proliferation will be evaluated by measuring the incorporation of BrdU (Cell Proliferation ELISA, BrdU-Sigma). The results will be analyzed on the basis of 3 independent experiments.

2—Study of the impact of PRP on the survival, proliferation and differentiation of healthy H9NSC or iPSC/NSC The H9NSC or iPSC/NSC cells will be cultured in the presence of PRP for 24 h, 48 h and 72 h, over 4 passages, at which time toxicity, proliferation and apoptosis will be analyzed. Cells grown in StemProNSC proliferation medium will be used in control.

Evaluation of toxicity/apoptosis: The toxicity of the PRP solution will be evaluated by measuring the release of LDH (CytoTox 96@Non-radioactive Cytotoxicity Assay—Promega) and apoptosis using the caspase-3/7 kit (Caspase-Glo® 3/7 Assay—Promega).

Proliferation Evaluation: Proliferation will be evaluated by measuring the incorporation of BrdU (Cell Proliferation ELISA, BrdU-Sigma). The results will be analyzed on the basis of 3 independent experiments.

Evaluation of the differentiation: the differentiation will be evaluated either on 30 days in monolayer, or on 6 and 12 weeks in 3D. Differentiation is assessed by q-RT-PCR and immunofluorescence of 9 markers of cell lineage and cellular functionality (NSC, neuronal, astrocytic, serotoninergic, GABAergic, acetylcholinergic, Dompaminergic, Glutamatergic, synaptic activity)

3—Study of the impact of PRP on the survival, proliferation and differentiation of healthy H9NSC or iPSC/NSC maintained as Neurosphere.

The H9NSC, iPSC or NSCf cells will be grown in the neurosphere in the presence of PRP for 24 h, 48 h and 72 h over 4 time passages at which toxicity, proliferation and apoptosis will be analyzed. Cells grown in StemProNSC proliferation medium will be used in control.

Evaluation of toxicity/apoptosis: The toxicity of the PRP solution will be evaluated by measuring the release of LDH (CytoTox 96@Non-radioactive Cytotoxicity Assay—Promega) and apoptosis using the caspase-3/7 kit (Caspase-Glo® 3/7 Assay—Promega).

Proliferation Evaluation: Proliferation will be evaluated by measuring the incorporation of BrdU (Cell Proliferation ELISA, BrdU-Sigma). The results will be analyzed on the basis of 3 independent experiments.

Evaluation of the differentiation: the differentiation will be evaluated either on 30 days in monolayer, or on 6 and 12 weeks in 3D. Differentiation is assessed by q-RT-PCR and immunofluorescence of 9 markers of cell lineage and cellular functionality (NSC, neuronal, astrocytic, serotoninergic, GABAergic, acetylcholinergic, Dompaminergic, Glutamatergic, synaptic activity)

4—Study of the Impact of PRP Replacing Conventional Media on the Survival, Proliferation and Differentiation of H9NSC or Healthy iPSC/NSC.

H9NSC, iPSC or NSCf cells will be cultured in monolayers on plates previously coated with PRP preparations (for 24 h, 48 h and 72 h, at which time the toxicity, proliferation and apoptosis will be analyzed on 4 passages. Cells grown in StemProNSC proliferation medium will be used in control.

- Evaluation of toxicity/apoptosis: The toxicity of the PRP solution will be evaluated by measuring the release of LDH (CytoTox 96@Non-radioactive Cytotoxicity Assay—Promega) and apoptosis using the caspase-3/7 kit (Caspase-Glo® 3/7 Assay—Promega).
- Proliferation Evaluation: Proliferation will be evaluated by measuring the incorporation of BrdU (Cell Proliferation ELISA, BrdU-Sigma). The results will be analyzed on the basis of 3 independent experiments.
- Evaluation of the differentiation: the differentiation will be evaluated either on 30 days in monolayer, or on 6 and 12 weeks in 3D. Differentiation is assessed by q-RT-PCR and immunofluorescence of 9 markers of lineages and cellular functionality (NSC, neuronal, astrocytic, serotoninergic, GABAergic, acetylcholinergic, Dompaminergic, Glutamatergic, synaptic activity).

5—Study of the Impact of PRP on Integration into an Integrated Brain System

The analysis can be done with 1 cell type H9NSC or iPSC/NSC healthy 20 weeks
- Cell grafting on brain slices in organotypic culture and cell fate analysis.
- Cell transplantation into C57Bl/6J mice and cell fate analysis.
- Cell transplantation on slices of brain modeling neurodegenerative pathology (Alzheimer's disease) in organotypic culture and cell fate analysis.

6—Study of the Impact of PRP on the Phenotype of iPSC/NSC Cells from Patients with Alzheimer's Disease We generated 3 iPSC lines from 3 patients with Alzheimer's disease. Two patients were carriers of genetic form (D694N mutation in the APP gene or G217D mutation in the PSEN1 gene) and a patient with a sporadic form. These cells have phenotypes already distinct from healthy cells. We will evaluate the impact of PRP in particular the ability of PRP to prevent cell death or alteration of differentiated cell phenotype. We will also evaluate the two major criteria characteristic of AD: As levels and Tau phosphorylation.

- Study of the impact of PRP on iPSC/NSC MA survival, proliferation and differentiation in comparison with healthy iPSC/NSC controls.
- Evaluation of toxicity/apoptosis: The toxicity of the PRP solution will be evaluated by measuring the release of LDH (CytoTox 96@Non-radioactive Cytotoxicity Assay—Promega) and apoptosis using the caspase-3/7 kit (Caspase-Glo® 3/7 Assay—Promega).
- Proliferation Evaluation: Proliferation will be evaluated by measuring the incorporation of BrdU (Cell Proliferation ELISA, BrdU-Sigma). The results will be analyzed on the basis of 3 independent experiments.
- Evaluation of the differentiation: the differentiation will be evaluated either on 30 days in monolayer, or on 6 and 12 weeks in 3D. Differentiation is assessed by q-RT-PCR and immunofluorescence of 9 markers of lineages and cellular functionality (NSC, neuronal, astrocytic, serotoninergic, GABAergic, acetylcholinergic, Dompaminergic, Glutamatergic, synaptic activity).
- Evaluation of the addition of PRP on differentiated cells. Differentiation is assessed by q-RT-PCR and immunofluorescence of 9 markers of lineages and cellular functionality (NSC, neuronal, astrocytic, serotoninergic, GABAergic, acetylcholinergic, Dompaminergic, Glutamatergic, synaptic activity).
- Study of the impact of PRP on secreted As levels and on Tau phosphorylation on proliferating cells, on differentiated cells
- Assay Aβ40 and Aβ42 by multiplex ELISA and evaluation of Aβ40/Aβ42 ratio
- Tau/phosphoTau dosage Example 10—Autologous Platelet-Rich Plasma (CC-PRP) Boosts Safely Human In Vitro Fibroblast Expansion Abstract Nowadays autologous fibroblast application for skin repair presents an important clinical interest. In most cases, in vitro skin cell culture is mandatory. However, cell expansion using xenogeneic or allogenic culture media presents some disadvantages, such as the risk of infection transmission or slow cell expansion. In this study, we investigated an autologous culture system to expand human skin fibroblast cells in vitro with the patient's own platelet-rich-plasma (PRP). Human dermal fibroblasts were isolated from patients undergoing abdominoplasty and blood was collected to prepare fresh PRP using the CC-PRP medical device. Cultures were followed up to 7 days using a media supplemented with either fetal bovine serum (FBS) or PRP. Fibroblasts cultured in medium supplemented with PRP showed dose dependently significantly higher proliferation rates (up to 7.7 times with 20% of PRP) and initiated a faster migration in the in vitro wound healing compared to FBS, while chromosomal stability was maintained. At high concentrations, PRP changed fibroblast morphology, inducing cytoskeleton rearrangement and an increase of alpha-SMA and vimentin expression. Our findings show that autologous PRP is an efficient and cost-effective supplement for fibroblast culture and should be considered as a safe alternative to xenogeneic/allogenic blood derivatives for in vitro cell expansion.

Impact Statement

Autologous dermal fibroblast graft is an important therapy in skin defect repair, but in vitro skin cell culture is mandatory in most cases. However, cell expansion using xenogeneic/allogenic culture media presents some disadvantages, such as the risk of infection transmission. We demonstrated that an autologous culture system with the patient's own platelet-rich-plasma is an efficient, cost-effective and safe supplement for fibroblast culture. As it respects the good-manufacturing-practices and regulatory agencies standards, it should be considered as a potent alternative and substitute to xenogeneic or allogenic blood derivatives for the validation of future clinical protocols using in vitro cell expansion.

Introduction

Regenerative medicine has the potential to heal or replace tissues and organs damaged by age, disease or trauma, as well as to correct congenital defects. Preclinical and clinical data show promise for the treatment of chronic diseases and acute injuries or even some cancers.1 In the "toolbox" of regenerative medicine, cell therapy aims at delivering an autologous or allogenic cellular component to the patient for the repair or regeneration of the damaged tissue in order to restore the physiological functions.2 A wide range of cells can be used in cell therapy, including blood and bone marrow cells, mature and immature solid tissue cells, adult stem cells and, most controversially, embryonic stem cells. Skin is a multifunctional and protective barrier in humans that contains essential stem cell populations and various cellular types that are critical for renewing and maintaining its structural integrity and functions.2 Therapeutic wound healing and the restoration of skin structures and functions depend on many factors, including the availability of progenitor cells, extracellular matrix (ECM) components, growth factors and cytokines for the angiogenesis and regulation of cell-matrix and cell-cell interactions. Fibroblasts, the major cell type of the dermis, produce the key ECM proteins in the dermis including laminins, fibronectins, collagens, elastic fibers, non-collagen molecules and growth factors that regulate cell function, migration and the cell-matrix and cell-cell interactions in normal skin homeostasis and wound healing.3 Dermal fibroblasts have already demonstrated clinical potential as therapeutic devices in skin wound healing4, tissue regeneration5 or as a dermal filler in esthetic and plastic surgery procedures.6 Some authors even suggest that fibroblasts in the context of regenerative medicine may be used as a more practical and potentially more effective cell therapy than mesenchymal stem cells.7

Autologous cell therapy aims at decreasing the risk of an adverse immune reaction or infection transmission. In most cases, the cells must be expanded in vitro before treatment to obtain a homogenous cell population and a sufficient number. Recently, the United States Food and Drug Administration (FDA) observed that over 80% of investigational new drug applications for cell therapy products used fetal bovine serum (FBS) during the manufacturing process.8 However, this xenogeneic additive presents a potential risk of infection and immunological reaction and offers a slow cell proliferation. Therefore, the search for a safe and efficient serum substitute is primordial. Some authors have proposed to replace FBS in culture media with autologous human serum for cell expansion, but as cell proliferation was slow, it still required a long culture time (3 weeks) and several cell passaging before transplantation.9, 10 In a previous study, we demonstrated that autologous platelet-rich plasma (PRP) could be used as a safe, efficient and cost-effective culture media for adipose-derived mesenchymal stem cell proliferation.11 Media supplied with 20% autologous PRP increased cell proliferation more than 13-fold without changing the cell phenotype. Currently, PRP obtained from patient's own blood is already used efficiently in the clinical setting for wound healing, bone regeneration or skin rejuvenation.12 Platelets are a natural supplier of autologous growth factors, key controllers of cell proliferation, differentiation and tissue regeneration. Under physiological conditions, platelets can be activated and their α-granules can gradually secrete growth factors and cytokines, such as platelet-derived growth factor (PDGF), epidermal growth factor (EGF), fibroblast growth factor (FGF), transforming growth factor-β(TGF-β) and vascular endothelial growth factor (VEGF). We thus postulate that autologous PRP can serve as a safe and effective biological supplement alternative to current non-autologous products for skin fibroblast expansion. In this study, we assessed the efficiency of autologous PRP compared obtained using a CC-PRP device to the classical FBS-supplemented culture medium to define an autologous system for human dermal fibroblast (NHDF) proliferation. We investigated the optimal PRP concentration and assessed the biological effects of media supplemented with PRP on migration, adhesion, differentiation and genomic stability of NHDF.

Materials and Methods

Cell Isolation

NHDF was isolated from 10 healthy women undergoing abdominoplasty in our Plastic, Reconstructive and Aesthetic Surgery Department at Geneva University Hospitals (Geneva, Switzerland). The procedure conformed to the principles of the Declaration of Helsinki and was approved by the local institutional ethics committee (protocol #3126). Informed written consent was obtained from all the donors. NHDF was isolated as described elsewhere13 and cultivated in complete growth medium (Dulbecco's Modified Eagle's medium [DMEM]; Life Technologies, Paisley, UK) supplemented with 10% FBS, 1% HEPES 1 M buffer solution (Life Technologies), 1% nonessential amino acid mixture 100× (Life Technologies), 1% L-glutamine 100× (Life Technologies), 1% penicillin/streptomycin 100× (Life Technologies), 1% sodium pyruvate 100× (Life Technologies) and stored up to 1 month at 4° C. Depending on the procedure, they were used at passages 1 or 2.

Preparation of Human Autologous PRP

PRP was prepared from the blood of the same NHDF donor by using the CC-PRP medical device. These specific tubes containing sodium citrate as an anticoagulant, separate platelets and plasma from other blood components (e.g., red and white blood cells) thanks to a specific separator gel. In brief, 30 mL of human peripheral blood was collected into three CC-PRP tubes (10 mL/tube). The collected blood was centrifuged for 5 min in a standard laboratory centrifuge at 1500 g. Subsequently, the red and white blood cells accumulated at the bottom of the tube under the separator gel, whereas the plasma and platelets remained above the gel layer. Plasma-containing platelets was homogenized by returning the tube five times to obtain 6.0 mL of PRP, which was collected in a polypropylene tube (Becton-Dickinson, Franklin Lakes, NJ, USA) until use. Platelets, red and white blood cells, as well as mean platelet volume in whole blood were counted (KX-21N; Sysmex, Lincolnshire, IL, USA) before centrifugation and in the prepared PRP before addition to culture media.

Cell Proliferation Assay

Cell proliferation was assessed by CellTrace™ Violet (Molecular Probes, ThermoFischer Scientific, Waltham, MA, USA) staining. At passage 2, NHDFs were seeded in 24-well plates at a density of 8×10³ cells per well and cultured in 10% FBS or treated with a range of PRP concentrations (1-50%) for 7 days. Quantification of cell proliferation was performed by flow cytometry using the Attune Acoustic Focusing Cytometer (Life Technologies) according to the manufacturer's protocol.

To perform cell cycle analysis, we measured the DNA content. In brief, NHDFs were seeded in 12—well plates at a density of 4×10⁵ cells per well and cultured in 10% FBS or treated with a range of PRP concentrations (1-50%) for 2 days and 7 days. Cells were trypsinized using Tryple X and then fixed with 70% ethanol. Cells were then permeabilized and nuclear DNA content was stained with FxCycle PI solution (Molecular Probes) at room temperature. Samples were run using the Attune Acoustic Focusing Cytometer (Thermofisher Scientific). The cell cycle analysis was performed using FlowJo software.

Cell Morphology, Alpha-SMA and Vimentin Expression

To study cytoskeletal rearrangements, cells were seeded in black with clear bottom 96-well plates (µClear, Greiner, Kremsmünster, Austria) at a concentration of 105 cells/mL in DMEM supplemented with 0.5% FBS for 24 h, and then treated with a range of PRP concentrations (1-50%) for 7 days. NHDFs were fixed with 4% paraformaldehyde for 10 min and permeabilized with 0.1% Triton X-100 for 5 min at room temperature. They were then stained with 50 µL of 5 U/mL phalloidin (Life Technologies), washed twice with PBS, and marked with 50 µL of 1 µg/mL DAPI for 5 min. To assess vimentin expression, a mouse monoclonal anti-vimentin antibody FITC (V9, eBiosciences, ThermoFischer Scientific) at 2.5 µg/ml for 1 h at room temperature was used. To depict alpha-SMA expression, a rabbit polyclonal anti-alpha SMA (Abcam, ab 5694) was used at 2 µg/ml for 1 h at room temperature, followed by a secondary goat anti-rabbit polyclonal Alexa fluor 594 (Abcam, ab 150080) at 2 µg/ml for 1 h at room temperature. Cytation 3 cell imaging multimode reader (BioTek) was used to visualize immunofluorescence staining. To measure alpha-SMA protein expression, NHDFs were seeded in 6-well plates at a density of 5×105 cells per well and cultured in 10% FBS or treated with a range of PRP concentrations (1-50%) for 4 days. Cells were detached with Tryple X and then then fixed with 2% paraformaldehyde in PBS for 10 min. After washing in PBS, cells were permeabilized with 0.1% Triton X-100 for 5 min. Single-cell suspensions of 106/ml were incubated with optimal concentrations of anti-alpha SMA antibody (Abcam, ab5694) at 2 µg/ml in wash buffer (2% normal goat serum in PBS) for 1 h at room temperature, washed three times, followed by a 1-h incubation with a goat anti-rabbit IgG H&L (Alexa Fluor®594, Abcam). Flow cytometry was performed on Attune Nxt Flow Cytometer (Life Technologies). Control samples consisted of cells without primary antibody binding.

Cell Exocytosis and Metabolic Activity Assessment by MTT Assay

The reduction of the tetrazolium salt 3-(4,5-dimethylthiazol-2-yl)-2,5-diphenyltetrazolium bromide (MTT) is an index of the redox status of the cell. The amount of formazan production indicates the reductive potential of the cytoplasm and thus cell viability. It is one of the most frequently used methods to measure cell proliferation and cytotoxicity. MTT is taken up by cells by endocytosis and reduced to formazan in the endosomal/lysosomal compartment. Formazan is deposited intracellularly as blue granules.14 In particular situations, 15 it can be exocytosed and form needle-like formazan crystals. NHDFs were seeded in 96-well plates at a density of 104 cells per well and incubated overnight in DMEM containing 0.5% FBS. The following day, cell cultures were treated for 48 h with a range of PRP concentrations (5-20%) and then 10 µL MTT were added (final concentration 500 µg/mL) for 4 h at 37° C. Pictures (100× magnification) were taken with an inverted microscope (Nikon). The medium was then aspirated and insoluble formazan crystals were dissolved with 100 µL DMSO per well. The plate was then placed on a shaker for 5 min (150 rpm). Absorbance was read at 595 nm on a microplate reader (Biotek).

Cell Adhesion Assay

For the evaluation of cell adhesion on laminin and collagen type I, experiments were performed in triplicate in 96-well plates. NHDFs were plated at a density of 1×104 cells/well on 96-well plates precoated with laminin (10 µg/mL) and collagen type I (50 µg/mL). Cells were allowed to adhere for 30 min, 1 h or 4 h at 37° C. in 10% FBS or with 10% PRP. Plates were washed three times with PBS, fixed with 4% paraformaldehyde for 10 min, stained with 0.1% crystal violet, and samples were rinsed with flow water and air-dried; images were taken under an inverted microscope. Samples were dissolved with glacial acetic acid and the optical density at 570 nm was determined by using an automatic microplate reader.

Wound Healing Assay

NHDFs were seeded in 96-well plates at a density of 4×104 cells per well and grown to confluence for 24 h. A scratch was created in the NHDF monolayer using a 10-µL pipette tip. The wells were washed twice with PBS to remove detached cells and pictures were taken in the center of each well. NHDFs were then incubated for 8 h in 10% FBS or with a range of PRP concentrations (1-50%). After incubation, NHDFs were washed with PBS and fixed in 4% paraformaldehyde. One image per well (center position, same as time 0) was obtained on a high-throughput Cytation 3 cell imaging multimode reader (BioTek). Quantification was performed using ImageJ software by measurements of the wounded areas at time 0 and 8 h.

Comparative Genomic Hybridization Array

Genomic stability was determined by comparative genomic hybridization array. NHDFs treated with FBS 10% or PRP 10% for 6 days were compared by using comparative genomic hybridization (CGH). DNA was extracted using the QIAGEN QIAamp DNA Mini Kit (Qiagen, Hilden, Germany) according to the manufacturer's protocol. Array CGH was performed using the Agilent SurePrint G3 Human CGH Microarray kit 4_180K (design ID 022060) with 43 kb overall median probe spacing (Agilent Technologies). Practical resolution was approximately 129 Kb. DNA extracted from cultured NHDF and control DNA (Promega male DNA, ref G1471) were pooled. Donor DNA and DNA of a sex-matched control (1 µg of each) was labelled with Cy3-dUTP and Cy5-dUTP, respectively (Sure Tag labeling kit, Agilent Technologies). Labeled products were purified by Amicon Ultra 30 K filters (Millipore, Burlington, MA, USA). Hybridization was performed according to the protocol provided byAgilent. Donor and control DNA were pooled and hybridized with 2 mg of human Cot-I DNA at 65° C. with rotation for 24 h. Arrays were analyzed using an Agilent SureScan Microarray scanner and the Agilent Feature Extraction software (v11.5) and results were presented by Agilent Genomic Workbench (v.7.0).

Statistical Analysis

For each cell culture experiment, treatments were performed in triplicate or quadruplicate. Unless otherwise stated, each experiment was repeated three times. Data are expressed as means±SEM. One-way ANOVA was used for multiple comparisons in experiments with one independent variable. A Dunnet's test was used for post hoc analysis of the significant ANOVA. A difference in mean values between groups was significant when p 50.05.

Results

Blood Cell and Platelet Counting in Whole Blood and PRP

Figure 13:
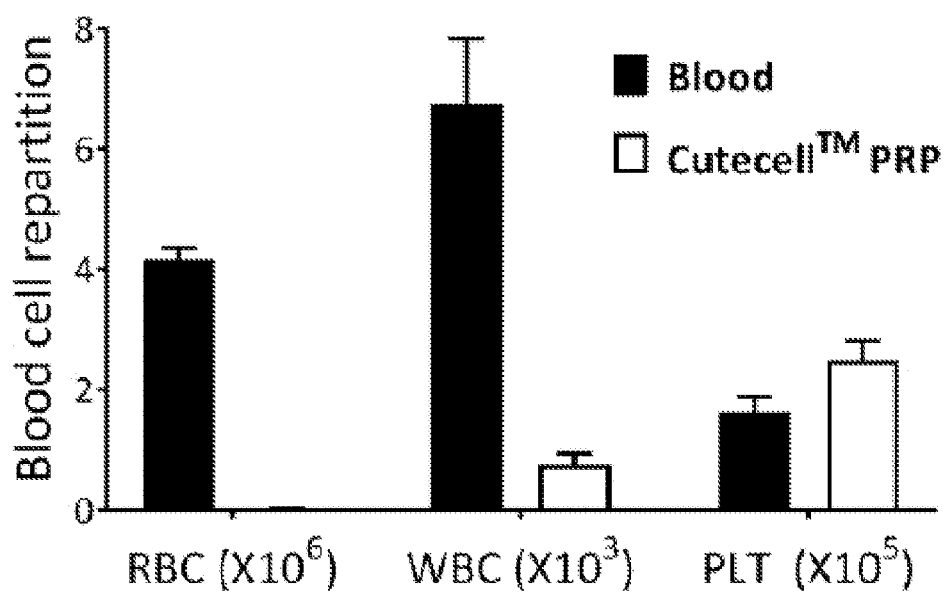
FIG. 13—shows blood and PRP cellular counts. Analysis of the number of platelets (PLT×105), white blood cells (WBC×103) and red blood cells (RBC×106) in whole blood compared to platelet-rich plasma (PRP) prepared with the CC-PRP device. (****p<0.0001). N=10 patients.

After centrifugation, most platelets accumulated over the gel separator at the bottom of the plasma. The platelets over the gel were suspended in the whole plasma (mean volume 6 ml) and this suspension was used as PRP. The final mean platelet concentration of PRP was 2.5×105+/−1.21 platelets/µL. This concentration was 1.53 times more than the whole blood before centrifugation (1.64×105+/−0.64 platelets/µL). The platelet recovery rate in PRP from the whole blood was 96%. Mean platelet volume was comparable between whole blood and PRP (8.7 fL+/−0.87 in whole blood versus 8.2 fL+/−0.82 in PRP). The mean white blood cell concentration was significantly lower in PRP compared to whole blood (0.75×103+/−0.7 cells/μL versus 6.75×103+/−2.88 cells/mL, respectively; p<0.05). The mean red blood cell concentration was also significantly reduced (0.03×106+/−0.001 cells/mL vs. 4.17×106+/−0.49 cells/mL, respectively; p<0.05) (n=10) (FIG. 13 A).

Figure 14:
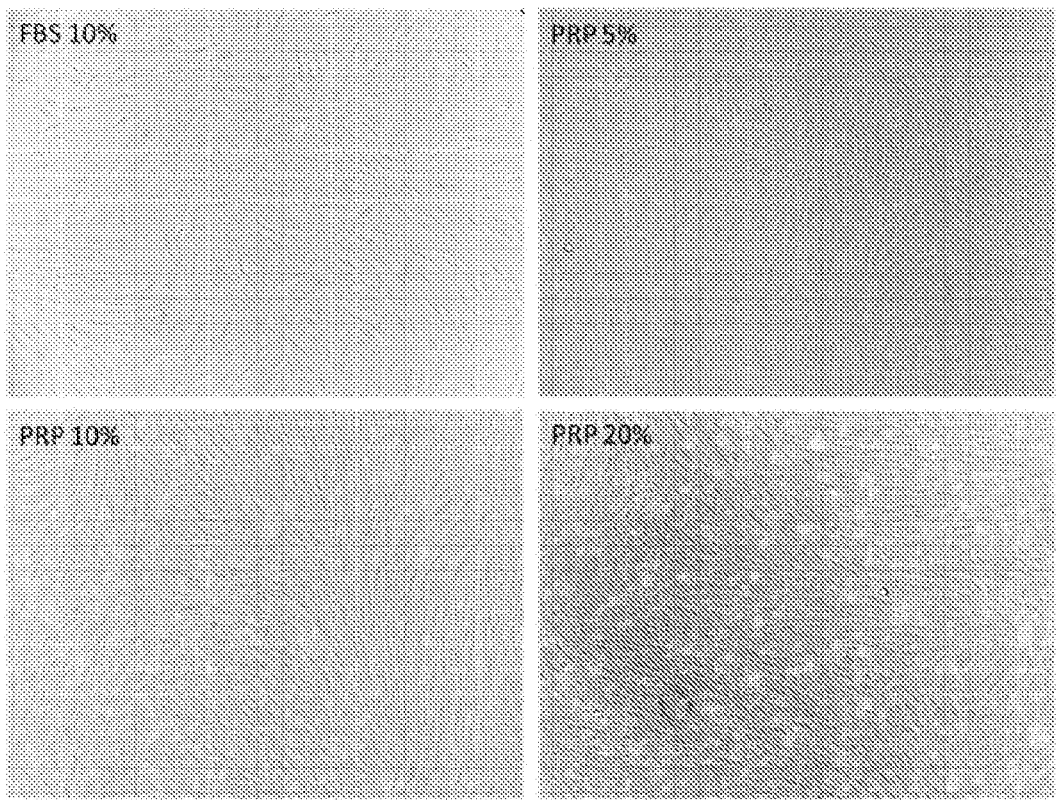
FIG. 14 shows bright field optical photography of NHDF in the presence of FBS 10% or PRP (5-20%) after 7 days of culture. Magnification 10×. Pictures are representative of one donor. Assessment of PRP proliferative effect by flow cytometry using CellTrace Violet (vital dye). Proliferative effect of increasing PRP concentrations in comparison (1-50%) with FBS 10% (n=10 different patients) on NHDF for 7 days without medium change in a complete autologous system (cells and PRP from the same patient).
Figure 15A:
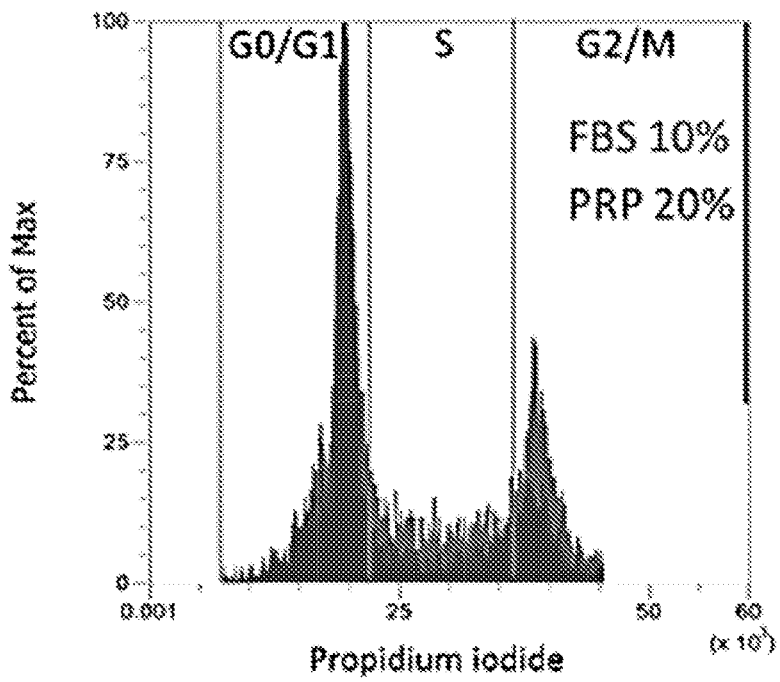
FIGS. 15(A) through 15(C) shows PRP-dependent cell cycle modulation in NHDFs, as show in FIG. 15(A). Descriptive cell cycle data of NHDFs after 48 h of incubation of treatment with PRP 50%. The histogram designates the increases in cell number in 'G2/M' phase arrest and decreases in cell number in the 'G1' phase. The graphic representation of cell numbers in the G1/G0, S and G2/M phases after 48 h of treatment, as shown in FIG. 15(B) and 7 days of treatment, as shown in FIG. 15(C).
Figure 15B:
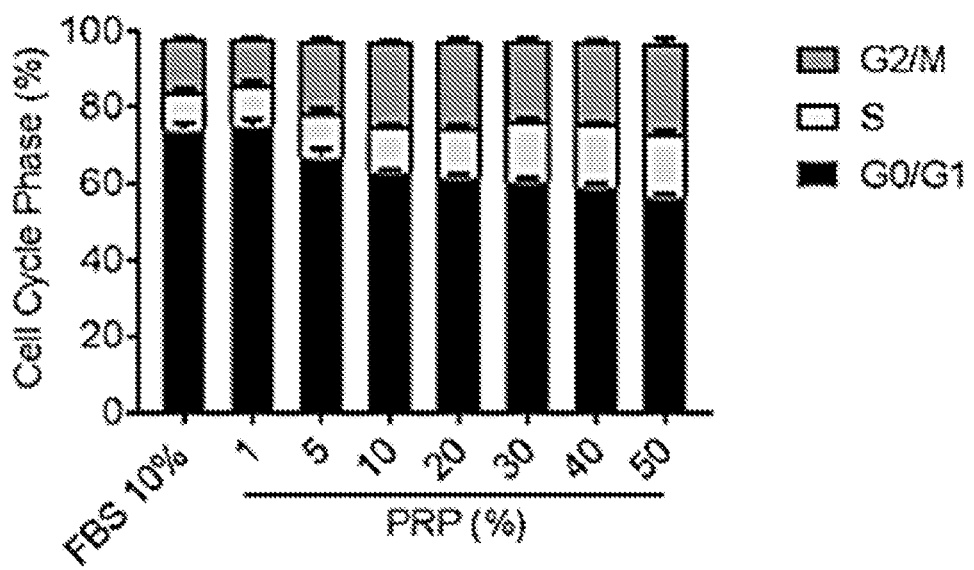
Figure 15C:
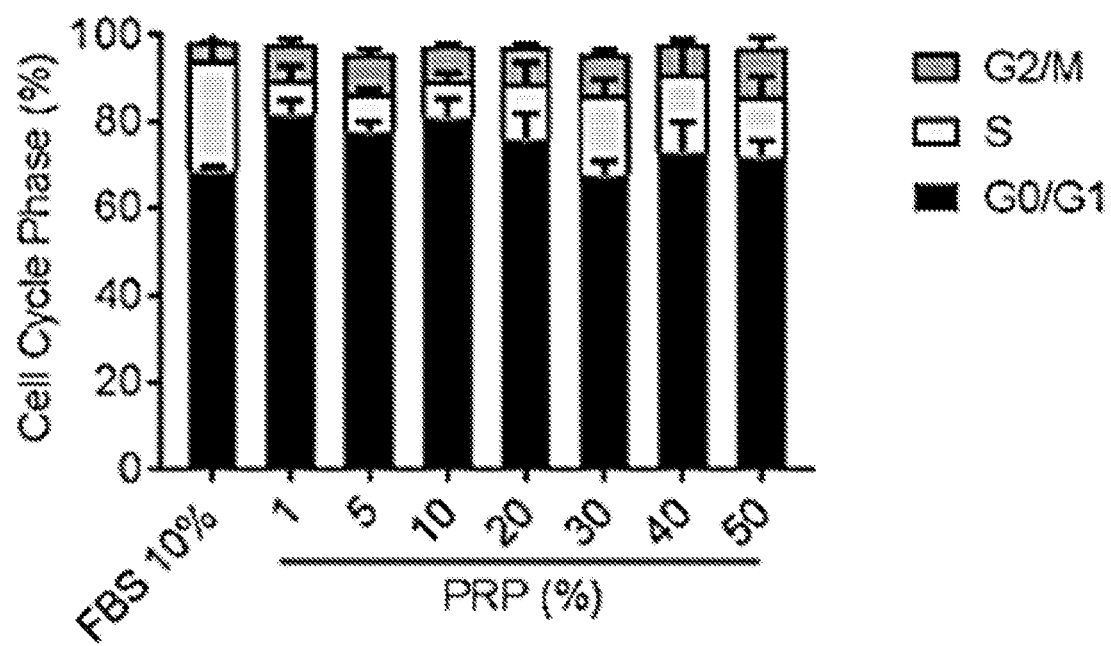

PRP Promotes a Dose-Dependent Increase of the Proliferation Together with Cell-Cycle Modifications After 7 days culture without changing the media, cultures supplemented with different PRP concentrations showed a higher viable NHDF number compared to FBS-containing media (FIG. 14). This proliferative effect of PRP followed a dose-dependent bell-shape curve. The optimal culture condition was PRP 20% where the NHDFs number was 7.7-fold higher than FBS 10% (n=10; p<0.001). It was observed that the treated samples with PRP exhibited significant cell cycle modifications compared to the control FBS-treated cells after 48 h. The mean percentage of cells in the "G0/G1" phase changed from 74.5% in the FBS 10% group to 62% in the 20% PRP group; in the "S" phase from 9.5% in the FBS 10% group to 13% in the PRP 20% group; in the "G2/M" phase from 14% in the FBS 10% group to 23% in the PRP 20% group (FIGS. 15 A and B). After 7 days of treatment, cells were confluent, DNA synthesis and mitosis were stopped, and cells entered the G0/G1 phase in a quiescent status with media supplemented with PRP (FIG. 15C).

Figure 16A:
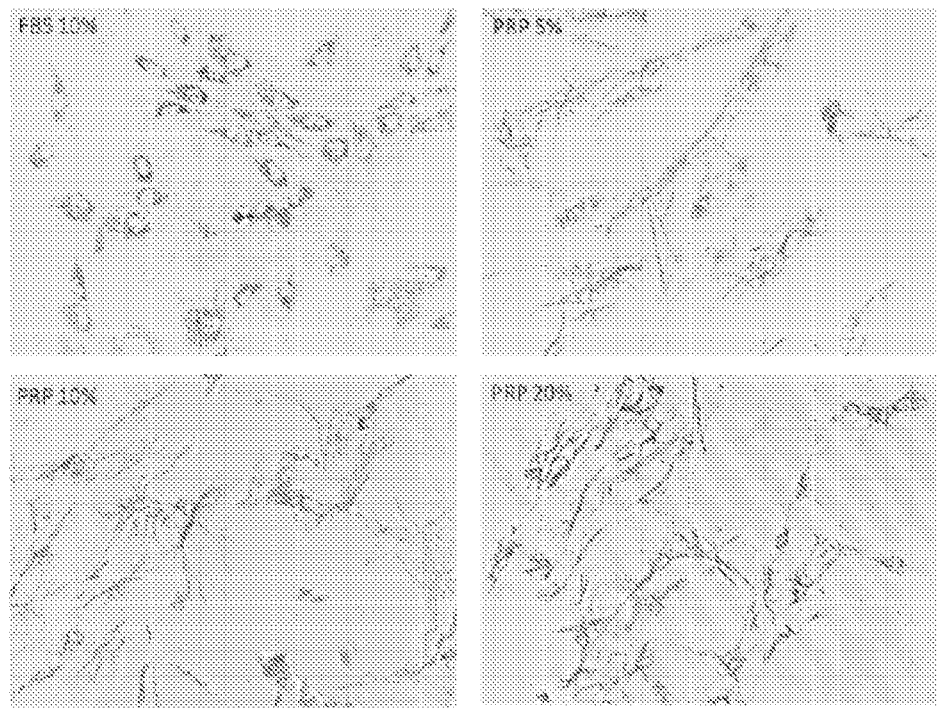
FIG. 16(A) shows representative bright-field microscopy images depicting the cellular localization of the MTT formazan in NHDF incubated for 48 h in different culture media. FBS-treated NHDF shows intracytoplasmic dark granules while PRP treated NHDF show extruded formazan crystals. Quantification of the solubilized formazan (absorbance measurements (570 nm), as shown in FIG. 16(B). Data are expressed as means+/−SD. $p<0.01$, $**p<0.0001$.
Figure 16B:
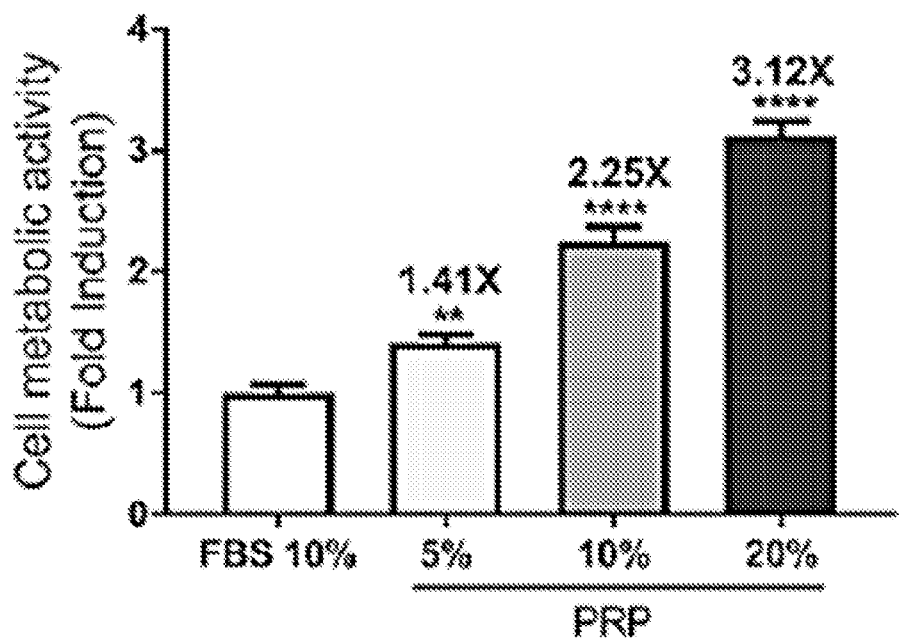

MTT Formazan Exocytosis is Induced by PRP Treatment Together with an Increase in Metabolic Activity When the cells are incubated with the tetrazolium salt MTT, they reduce the salt into a purple water insoluble formazan. This intracytoplasmic reduction of the salt is considered as an indicator of "cell redox activity" and thus related to mitochondrial enzymes. Under microscopic examination of the FBS-treated cultures (FIG. 16-5A), formazan granules were in intracellular organelles. However, when the cells were treated with PRP (5-20%) for 48 h, needle-like crystals appeared on the surface of the cells, representing exocytosed MTT formazan (FIG. 16A).

Moreover, when we quantified the amount of solubilized formazan by optical densitometry, we evidenced an increase in PRP-treated cells, directly reflecting an increase in cell metabolic activity (FIG. 16B) peaking at 3.12-fold in PRP 20%-treated cells compared to FBS 10%-treated cells after 48 h of treatment.

Figure 17A:
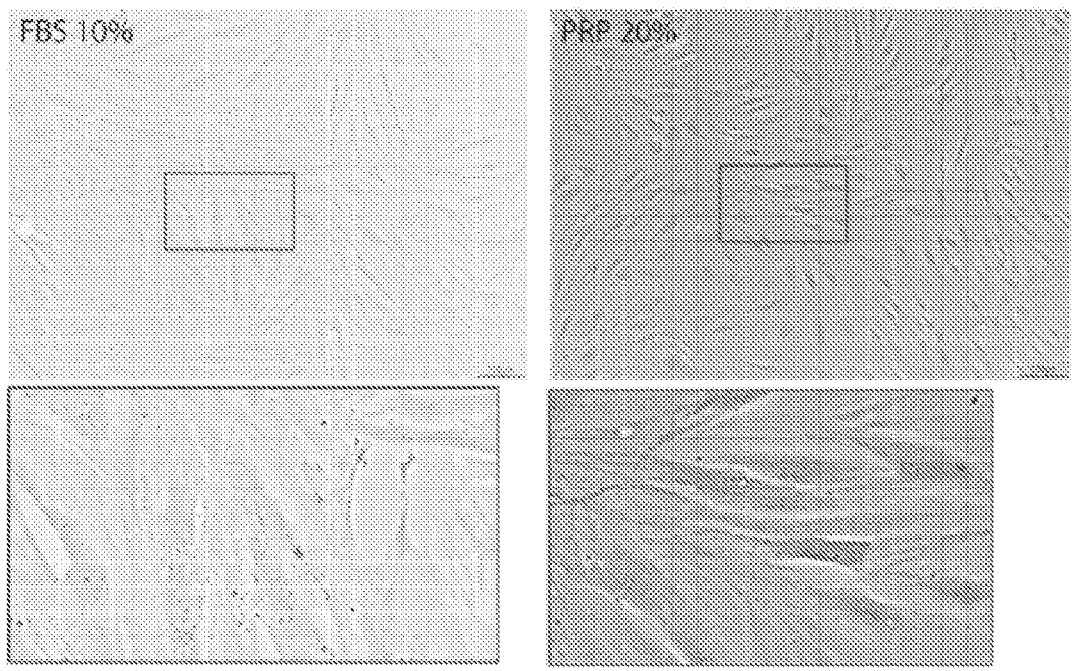
FIGS. 17(A) and 17(B) shows long-term PRP treatment (7 days) promotes NHDF cell shape modification, closely mimicking fibroblast to myofibroblast differentiation, as shown in FIG. 17(A). F-actin cytoskeletal reorganization was assessed. Prominent bundles of actin microfilaments appeared along the cytoplasm in PRP-treated cells, as shown in FIG. 17(B).
Figure 17B:
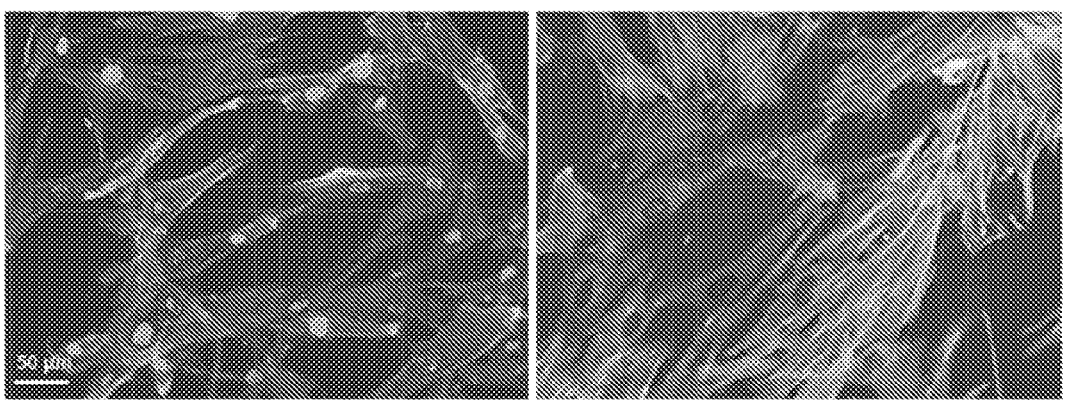
Figure 18A:
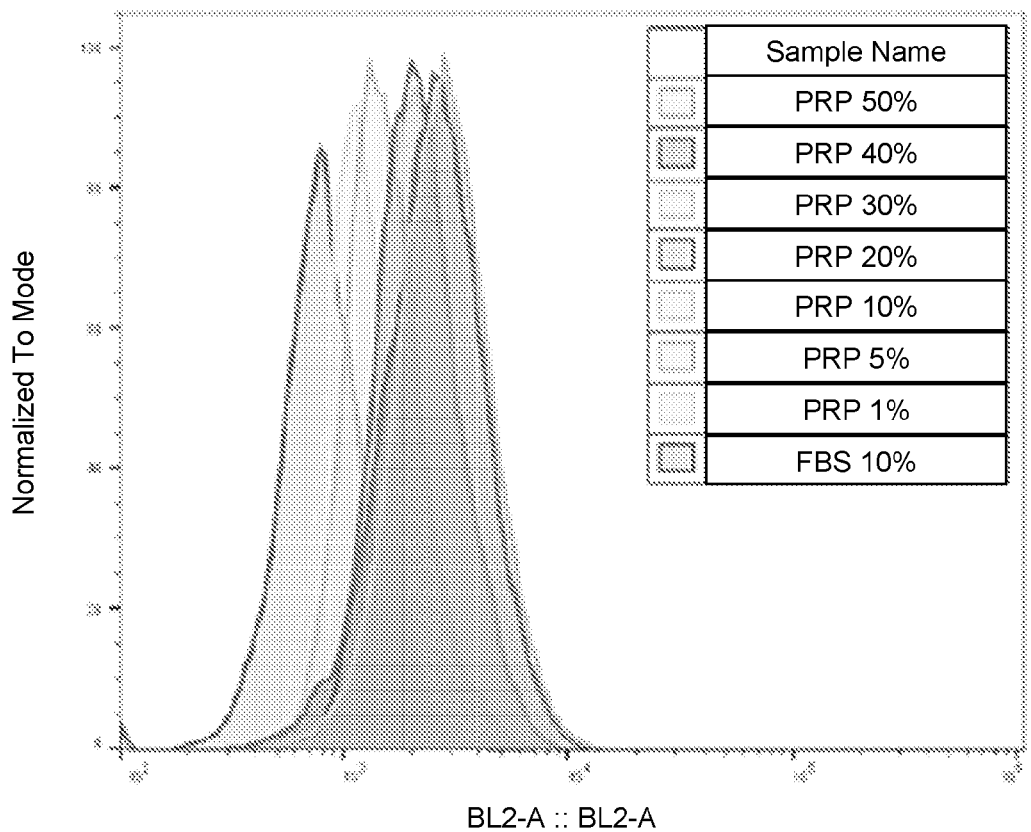
FIG. 18(A) shows flow cytometry histogram overlays of alpha-SMA positive cells of PRP-stimulated NHDF for 4 days compared to FBS 10%.
Figure 18B:
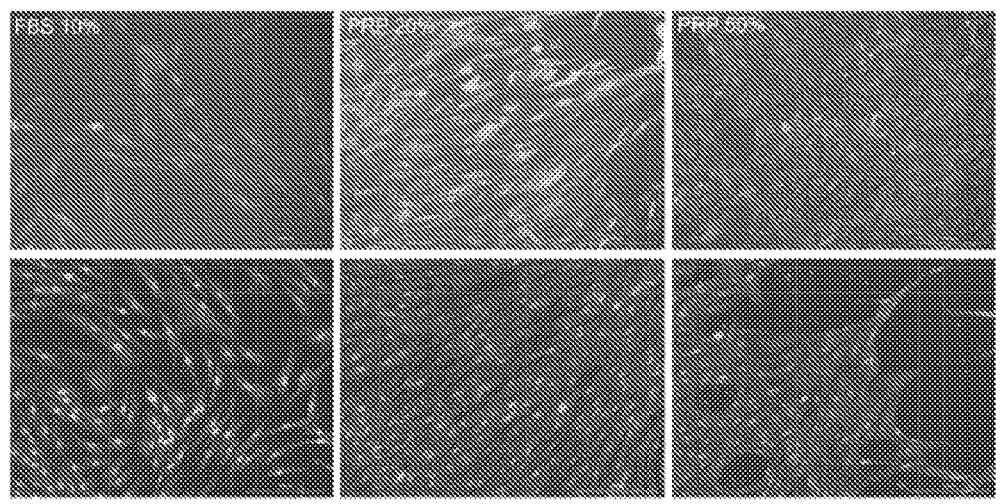
FIG. 18(B) shows Vimentin (upper line) and alpha-SMA (lower line) immunofluorescence on NHDF after 7 days of culture in the presence of FBS 10% or PRP (20-50%) in the culture media. Nuclei were counterstained with DAPI.

Assessment of PRP Effects on Cell Shape, Cytoskeleton, Vimentin and Alpha-SMA Expression NHDF cultured in classical FBS-supplemented culture medium showed a regular flattened cell shape while NHDF treated with PRP (10-50%) were spindle shaped, a morphology that is closer to 3D matrix cultures or in vivo setting (FIG. 2). We sought to investigate whether the morphological change occurring at 7 day's PRP treatment (FIG. 17A) was related to a phenotypical change. We first demonstrated prominent F-actin reorganization from cortical actin localization (FBS 10%) into thick cell-spanning filaments (PRP 20%) (FIG. 17B). We further assessed the changes in alpha-SMA expression upon PRP treatment by flow cytometry and immunofluorescent analysis (FIG. 18A). Alpha-SMA expression was significantly increased with a high PRP concentration (40-50%), while FBS and PRP 5-10%-treated cells showed a basal perinuclear staining (FIG. 18B). Immunofluorescent analysis showed an increase in vimentin staining in the presence of PRP 20% but it was completely abolished at high PRP concentration (PRP 50%).

Figure 19A:
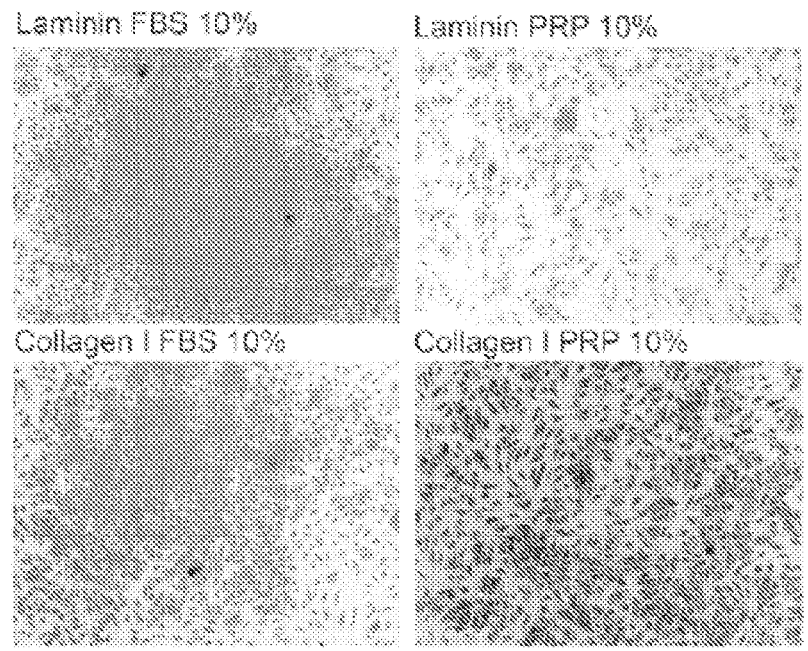
FIGS. 19(A) and 19(B) shows short-term PRP effect of NHDF adhesion to laminin and collagen I. NHDFs were stimulated with FBS 10% or PRP 10% for 15 min, 30 min or 4 h. Unattached cells were removed and adherent cells were fixed with methanol and stained with 0.1% crystal violet, as shown in FIG. 19(A). Cells were then solubilized and the released dye was quantified using a microplate reader (optical density at 590 nm), as shown in FIG. 19(B). Bars indicate standard errors. Number of replicates: between 10 and 20 wells per experimental condition. $*p<0.05$, $*p<0.001$, $**p<0.0001$.
Figure 19B:
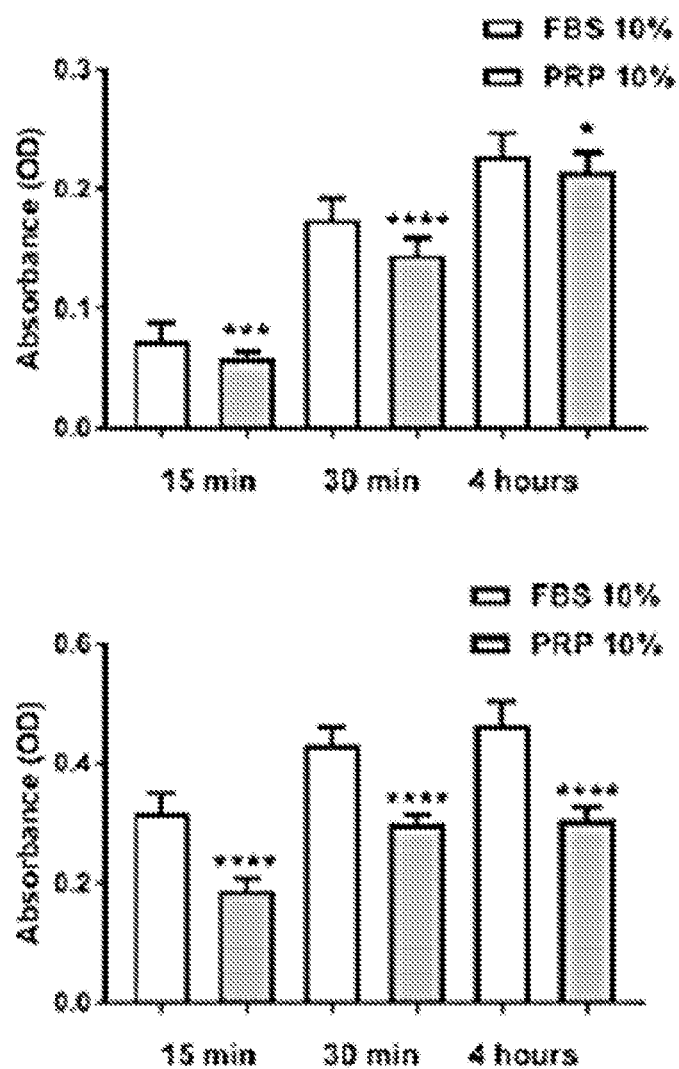
Figure 20A:
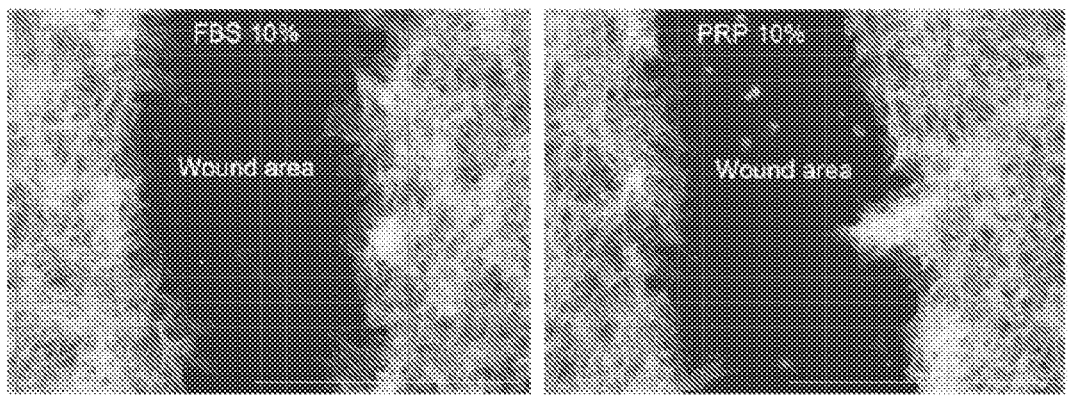
FIGS. 20(A) through 20(C) shows comparative cellular effects of PRP 10% treatment on cell migration in NHDF cultures.
Figure 20B:
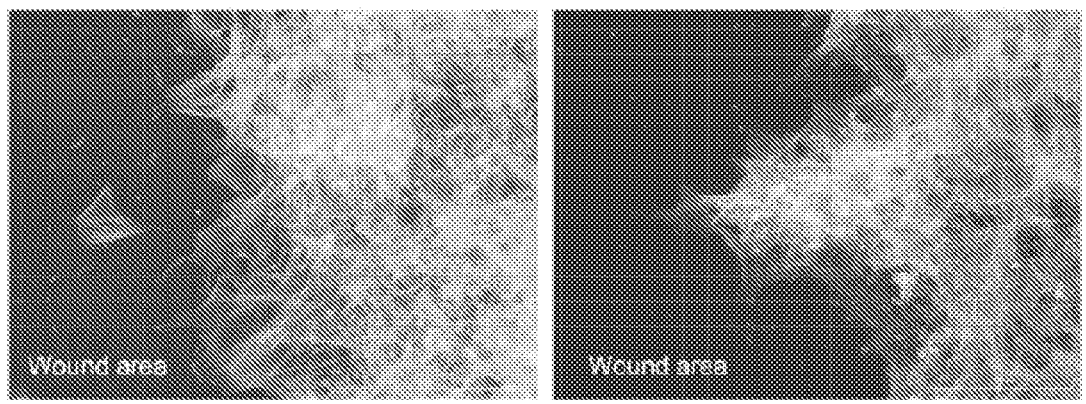
Figure 20C:
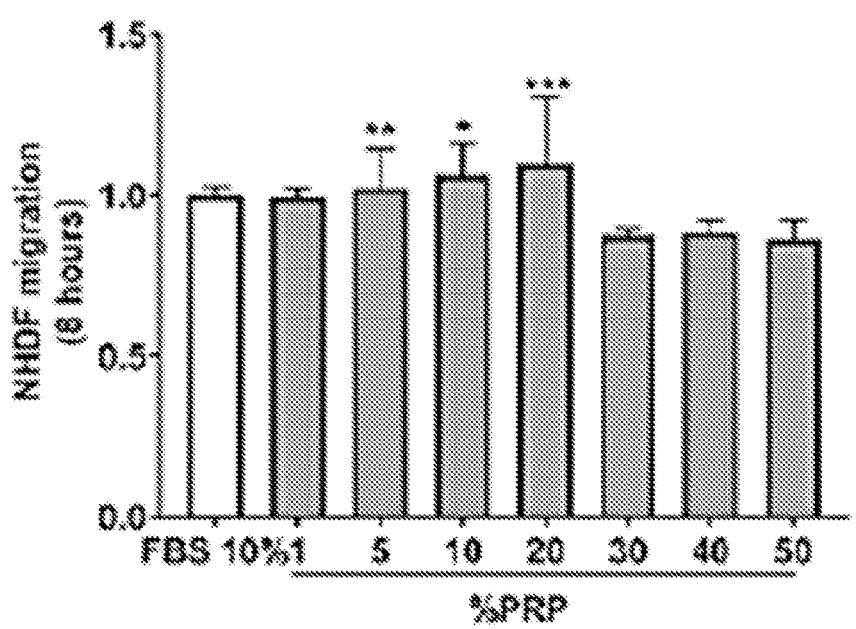

PRP Treatment Affects Cell Adhesion on Extracellular Matrix and Promotes Fibroblast Collective Migration To further characterize the biological effects of PRP on NHDF biology, we evaluated the effect of PRP treatment on cell adhesion on laminin and collagen type 1. As shown in FIG. 19A, PRP decreased the overall attachment of NHDFs to laminin 4 h after seeding. This effect occurred already after 15 min, with a 21% decrease in overall cell adhesion. The same results were obtained for NHDF attachment to the collagen I matrix (FIG. 19B) (41% of total cell adhesion after 15 min). To study the migratory properties of NHDFs exposed to PRP, we performed an in vitro scratch assay (FIG. 20). Eight hours of 20% PRP treatment induced a 10% increase in the number of migrating cells from the scratch margin into the scratch zone compared to cell cultures with FBS. This migration front was a collective cell migration. Conversely, NHDFs exposed to FBS 10% showed features of isolated cell migration.

PRP does not Modify Cell Genomic Stability

Figure 21A:
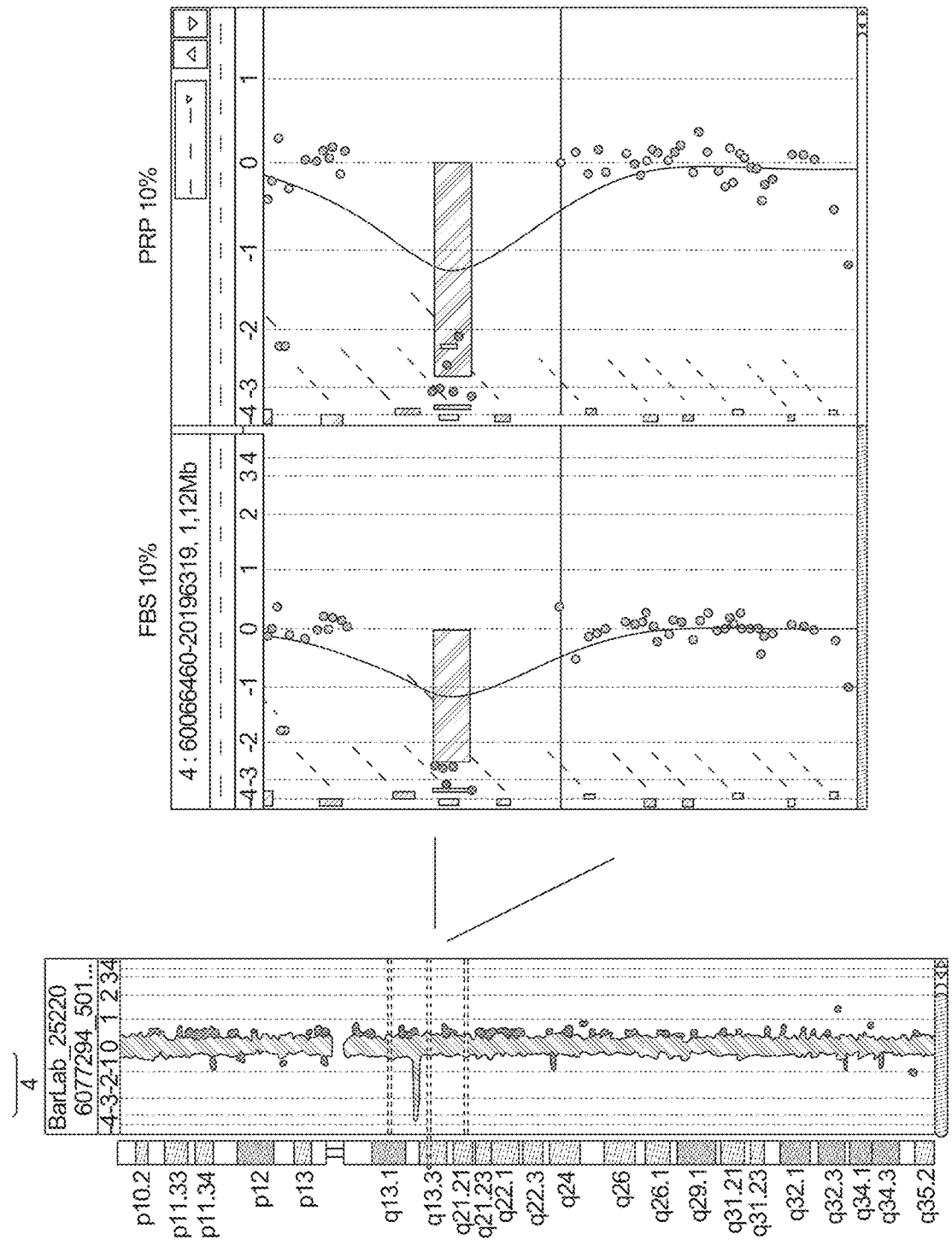
FIGS. 21(A) and 21(B) shows an array CGH profile of NHDFs treated with media containing FBS 10% or PRP 10% for 4 days.
Figure 21B:
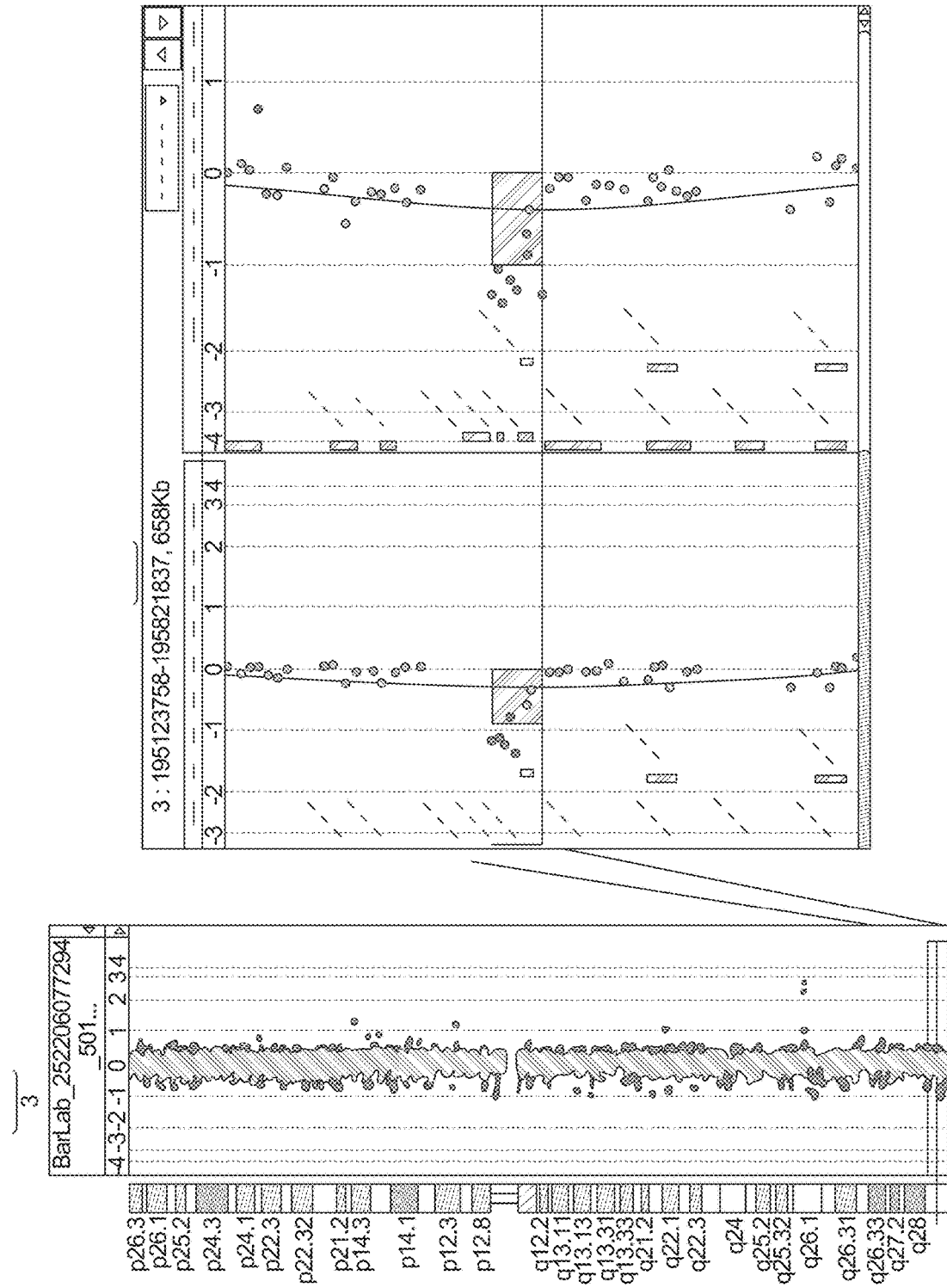
Figure 22B:
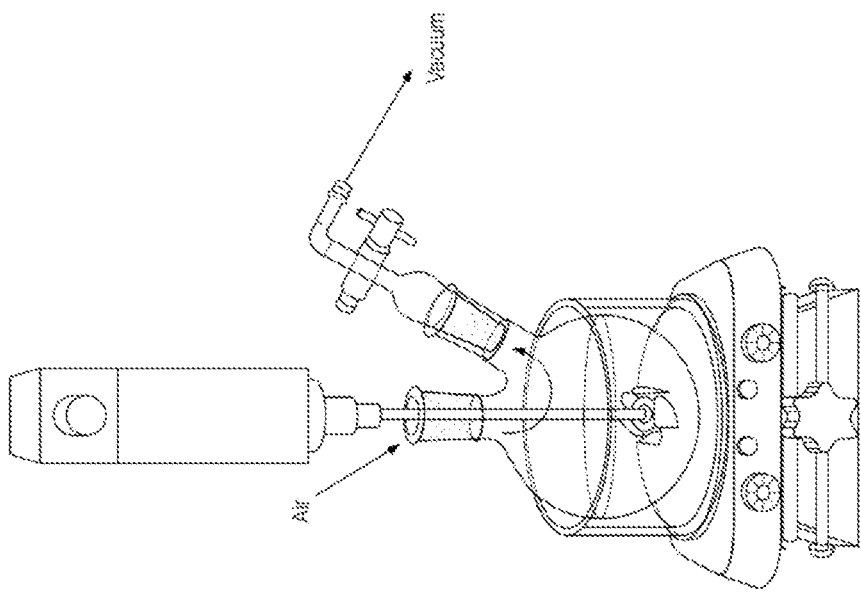
FIGS. 22(A) and 22(B) shows an experimental synthesis testing apparatus.
Figure 22A:
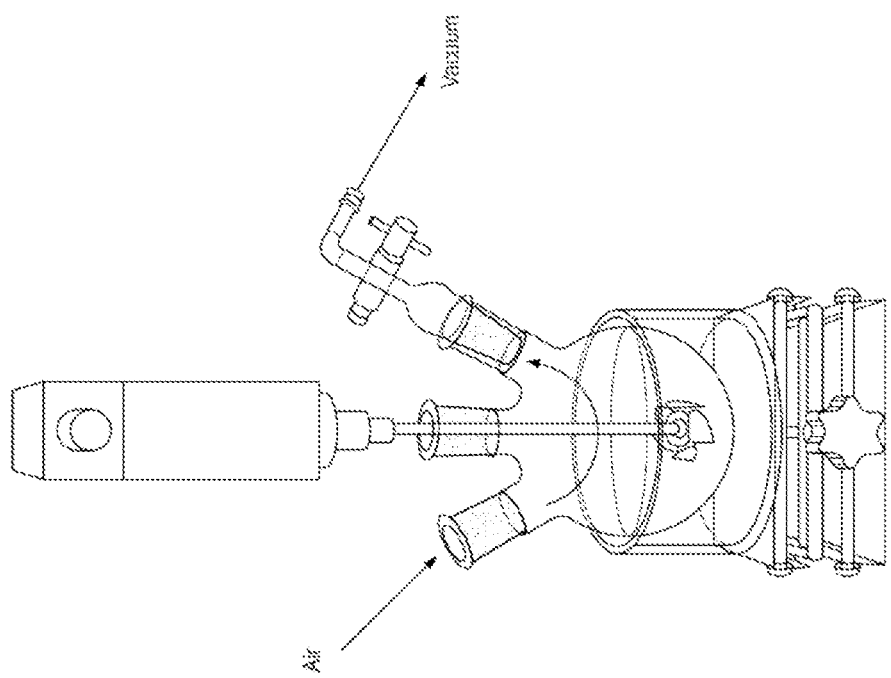

NHDFs at passage 2 were cultured for 4 days with media supplemented with FBS 10% or PRP 10% to document genetic stability during proliferation. Array CGH analysis of cells treated with the two different culture media did not show imbalanced chromosomal rearrangements. The increased proliferation rate in response to PRP treatment did not provoke genomic instability. To exemplify the data, the benign homozygous deletion depicted on chromosome 4 (region q13.2) was superimposable in NHDF cultivated in FBS 10% or PRP 10%, as well as the benign heterozygous deletion on chr3 in q29 region (FIG. 21).

Discussion

Autologous fibroblast treatments have a potential development in a range of esthetic and plastic surgery procedures.16 This clinical interest in autologous fibroblast therapy was developed following animal studies where it was shown that fibroblasts isolated from mature skin remained alive in vivo 5 months after intradermal injection and improved dermal thickness.17 Since 2011, LAVIV (Azficel-T, Fibrocell technologies, Exton, PA, USA), the first personalized autologous fibroblast cell therapy, was approved by the FDA for enhancement of nasolabial folds in adults.18 The main drawback of this technology is the cost and the extended time for cell culture (11-22 weeks) prior to injection, as well as the xenogeneic source of growth factors supplied by FBS to expand the cells in vitro. As all cell therapies with fibroblasts rely on an in vitro cell expansion, attempts have been made to subtract any factors of non-human origin, e.g., the use of FBS as a growth and nutrient supply in cell culture media. 8 Previously, few studies aimed to substitute FBS with PRP for the in vitro expansion of fibroblast originating from dermis or gingival tissue. 19-23 However, in these experimental settings using heterologous lysate PRP or activated PRP, the efficiency for cell proliferation was limited. Kakudo et al. showed a 2.5× human dermal fibroblast proliferation enhancement after 7 days of culture with 5% activated PRP, while 20% activated PRP did not promote proliferation. 19 Another study with NHDF showed only a 1.5× enhancement of proliferation by adding 5% activated PRP after 5 days.20 Recently, non-activated PRP prepared from a pool of 49 patients was shown to have a mild proliferative effect after 7 days of culture (1.3-fold). 23 However, in this study, Noh et al. didn't replace the FBS by PRP. They added an unknown concentration of PRP to a culture media containing FBS. To our knowledge, our study demonstrates for the first time the advantages of FBS substitution by different concentration of autologous non-activated PRP for NHDF expansion. PRP activation by thrombin, calcium or collagen, as performed in other studies, stimulates an immediate and important release of growth factors from 15 min up to 24 h only. Therefore, we believe that platelet activation is undesirable for applications as cell culture where the slow release of growth factors from gradual platelet degranulation is required. Mean platelet volume (MPV) is considered as a potential marker of platelet activity: larger platelets that contain more dense granules are enzymatically and metabolically more active than their smaller counterparts.24 In our study, M PV was comparable between whole blood and PRP (8.7 fL in whole blood versus 8.2 fL in PRP). As the PRP preparation did not change the MVP, it implies that processing did not cause platelet activation. In a previous study of adipose-derived stem cell expansion with a media containing non-activated PRP, we demonstrated that PDGF-AB and FGF concentrations peaked at day 5 and remained stable for more than 10 days, while TGF-B1 and VEGF were continuously secreted from day 0 to day 10.25 This was in direct correlation with 50% platelet viability after 10 days of culture.11 Moreover, the continuous and orchestrated secretion of GF by non-activated PRP over several days offers the possibility to change culture media only after 7 to 10 days, instead of every 3 days as required for other media supplements that do not contain platelets (e.g. FBS, PRP lysate).

The platelet concentration of PRP is a key factor that may influence its efficacy. Although PRP was defined historically as a plasma containing 4-5 times more platelets than whole blood,26 it is now admitted that high platelet concentration is no better than moderate numbers and could even be harmful. For example, in a 3D anterior cruciate ligament fibroblast culture, a PRP containing the same platelet concentration as whole blood presented the highest cell metabolism and the lowest apoptosis rate compared to higher platelet concentrations.27 Another study with oral fibroblast showed that increased platelet concentration in PRP (>2.5×) resulted in a reduction of the proliferation.28 In our study, the PRP prepared with the CC-PRP device contained 1.53 times more platelets than whole blood. Even the platelet recovery rate in PRP from the whole blood was 96, this relatively low platelet concentration was because the platelets were suspended in the whole plasma over the gel. Moreover, the effect of PRP was dose-dependent. Media supplemented with 20% of PRP offered the highest NHDF proliferation rate (7.7 times more than FBS culture medium), while media with more than 40% of PRP showed less proliferation capacity. This is in line with other studies demonstrating that media supplemented with a high PRP concentration is less effective than a moderate concentration. Atashi et al.11 also concluded that the best PRP concentration for in vitro adipose-derived mesenchymal stem cells expansion was the media supplemented with 20% of PRP. The harmful effect of high PRP concentration could be due to higher growth factor concentration that may provoke a down-regulation of cell receptor by a negative feedback loop. This mechanism could also explain why activated-PRP secreting more growth factors is less efficient in some applications. Further investigations are required to elucidate this hypothesis. By using autologous non-activated PRP, we demonstrated that PRP can be an efficient and safe substitute for other cell culture media supplements used for NHDF in vitro expansion. While growth factors present in PRP trigger cell division, they also exert other pleiotropic activity on fibroblast. Cellular functions that influence early wound healing were assessed in our culture setting. We demonstrated that PRP treatment speeds up cellular metabolic activity and fibroblast exocytosis capacities. It is associated with a cell shape modification and a cytoskeleton reorganization together with a collective cell migration. Although vimentin is considered as a mesenchymal marker expressed by fibroblast, it has also been newly recognized as a proliferation coordinator in wound healing.29 Under 20% PRP treatment, vimentin expression was enhanced, which is in direct correlation with the proliferation boost observed at this concentration. Expression of alpha-SMA (myofibroblast marker) was only triggered by high PRP concentrations (>40%). This is in line with the recent study of Chellini et al. demonstrating that PRP alone was not able to stimulate the myofibroblast phenotype acquisition. 30

There is some debate in the scientific community about the potential pro-neoplastic effect of long term PRP treatment.31 Furthermore, some studies raise questions about genetic stability during massive cell expansion.32 Therefore, we checked the genetic variations using CGH between cells grown in FBS versus PRP and demonstrated no unbalanced chromosomic rearrangement with PRP treatment.

This demonstration is of prime interest for translating PRP-cultured NHDF application into the clinical setting to meet legal regulatory requirements.

Our cell culture protocol including autologous PRP as a media supplement could be used for other cell type expansion. Furthermore, with this new culture setting, we would be able to shorten the time of the culture and to grow more cells (without cell passaging up to 7 days) for larger scale applications, such as large tissue injury. In a set of preliminary experiments (data not shown), we also demonstrated the same potent proliferative effect of PRP on human epidermal keratinocytes, where PRP 20% promoted a 10-fold increase of keratinocyte proliferation.

Conclusions

In this study, we have shown for the first time a completely autologous model for NHDF expansion using PRP as a safe biological supplement in culture medium. The various effects of PRP range from speeding up cell proliferation to modulating cell adhesion and migration without changing chromosomal stability, depending on the concentration and duration of the treatment. As this autologous technique respects Good Manufacturing Practice Guidelines and regulatory agencies standards, PRP should be considered as an efficient, cost-effective and safe supplement for fibroblast culture, as well as a substitute for xenogeneic or allogenic blood derivatives for the validation of future clinical protocols of in vitro cell expansion.

Further studies have shown efficacy in other therapeutic areas:

| TherapeuticAreas | Celltypes | Remarks |
| --- | --- | --- |
| MusculoSkeletal | Human myoblasts + A-PRP (allogenic-autologous) Human satellite cells + A-PRP (allogenic-autologous) Human articular chondrocytes + A-PRP (allogenic-autologous) Human MSC + A-PRP (allogenic-autologous) | Promising results on proliferation and differentiation into myocytes |

-continued

| TherapeuticAreas | Celltypes | Remarks |
|---|---|---|
| Liver Regeneration | Murine hepatocytes and endothelial cells + human PRP | Study on the interactions between platelets and liver sinusoidal endothelial cells PRP effect on hepatocyte proliferation |
| Uro-Gynecology | Human vaginal mucosal cells + autologous PRP Human clitoral endothelial cells + autologous PRP | |
| Angiogenesis | Human endothelial cells and fibroblast (3D in vitro model) + A-PRP (allogenic and autologous) | Promising preliminary results on 3D angiogenesis model |

REFERENCES

1. Mao, A. S., and Mooney, D. J. Regenerative medicine: Current therapies and future directions. Proceedings of the National Academy of Sciences of the United States of America 112, 14452, 2015.
2. Li, Z., and Maitz, P. Cell therapy for severe burn wound healing. Burns & trauma 6, 13, 2018.
3. Stunova, A., and Vistejnova, L. Dermal fibroblasts-A heterogeneous population with regulatory function in wound healing. Cytokine & growth factor reviews 39, 137, 2018.
4. Thangapazham, R. L., Darling, T. N., and Meyerle, J. Alteration of skin properties with autologous dermal fibroblasts. International journal of molecular sciences 15, 8407, 2014.
5. Costa-Almeida, R., Soares, R., and Granja, P. L. Fibroblasts as maestros orchestrating tissue regeneration. Journal of tissue engineering and regenerative medicine 12, 240, 2018.
6. Weiss, R. A. Autologous cell therapy: will it replace dermal fillers?Facial plastic surgery clinics of North America 21, 299, 2013.
7. Ichim, T. E., O'Heeron, P., and Kesari, S. Fibroblasts as a practical alternative to mesenchymal stem cells. Journal of translational medicine 16, 212, 2018.
8. Karnieli, O., Friedner, O. M., Allickson, J. G., Zhang, N., Jung, S., Fiorentini, D., Abraham, E., Eaker, S. S., Yong, T. K., Chan, A., Griffiths, S., Wehn, A. K., Oh, S., and Karnieli, O. A consensus introduction to serum replacements and serum-free media for cellular therapies. Cytotherapy 19, 155, 2017.
9. Eca, L. P., Pinto, D. G., de Pinho, A. M., Mazzetti, M. P., and Odo, M. E. Autologous fibroblast culture in the repair of aging skin. Dermatologic surgery: official publication for American Society for Dermatologic Surgery [et al]38, 180, 2012.
10. Nilforoushzadeh, M. A., Jaffary, F., Siavash, M., Ansari, N., Siadat, A. H., and Heidari, A. Autologous fibroblast suspension for the treatment of refractory diabetic foot ulcer. Indian journal of dermatology, venereology and leprology 82, 105, 2016.
11. Atashi, F., Jaconi, M. E., Pittet-Cuenod, B., and Modarressi, A. Autologous platelet-rich plasma: a biological supplement to enhance adipose-derived mesenchymal stem cell expansion. Tissue engineering Part C, Methods 21, 253, 2015.
12. Alves, R., and Grimalt, R. A Review of Platelet-Rich Plasma: History, Biology, Mechanism of Action, and Classification. Skin appendage disorders 4, 18, 2018.
13. Takashima, A. Establishment of fibroblast cultures. Current protocols in cell biology Chapter 2, Unit 2 1, 2001.
14. Berridge, M. V., Herst, P. M., and Tan, A. S. Tetrazolium dyes as tools in cell biology: new insights into their cellular reduction. Biotechnology annual review 11, 127, 2005.
15. Molinari, B. L., Tasat, D. R., Palmieri, M. A., and Cabrini, R. L. Kinetics of MTT-formazan exocytosis in phagocytic and non-phagocytic cells. Micron 36, 177, 2005.
16. Mehrabani, D., and Manafi, N. Role of cultured skin fibroblasts in aesthetic and plastic surgery. World journal of plastic surgery 2, 2, 2013.
17. Zhao, Y., Wang, J., Yan, X., Li, D., and Xu, J. Preliminary survival studies on autologous cultured skin fibroblasts transplantation by injection. Cell transplantation 17, 775, 2008.
18. Smith, S. R., Munavalli, G., Weiss, R., Maslowski, J. M., Hennegan, K. P., andNovak, J. M. A multicenter, double-blind, placebo-controlled trial of autologous fibroblast therapy for the treatment of nasolabial fold wrinkles. Dermatologic surgery: official publication for American Society for Dermatologic Surgery [et al]38, 1234, 2012.
19. Kakudo, N., Minakata, T., Mitsui, T., Kushida, S., Notodihardjo, F. Z., and Kusumoto, K. Proliferation-promoting effect of platelet-rich plasma on human adipose-derived stem cells and human dermal fibroblasts. Plastic and reconstructive surgery 122, 1352, 2008.
20. Kim, D. H., Je, Y. J., Kim, C. D., Lee, Y. H., Seo, Y. J., Lee, J. H., and Lee, Y. Can Platelet-rich Plasma Be Used for Skin Rejuvenation?Evaluation of Effects of Platelet-rich Plasma on Human Dermal Fibroblast. Annals of dermatology 23, 424, 2011.
21. Liu, Y., Kalen, A., Risto, O., and Wahlstrom, O. Fibroblast proliferation due to exposure to a platelet concentrate in vitro is pH dependent. Wound repair and regeneration: official publication of the Wound Healing Society [and] the European Tissue Repair Society 10, 336, 2002.
22. Nguyen, P. A., and Pham, T. A. V. Effects of platelet-rich plasma on human gingival fibroblast proliferation and migration in vitro. Journal of applied oral science: revista FOB 26, e20180077, 2018.
23. Noh, K. C., Liu, X. N., Zhuan, Z., Yang, C. J., Kim, Y. T., Lee, G. W., Choi, K. H., and Kim, K. O. Leukocyte-Poor Platelet-Rich Plasma-Derived Growth Factors Enhance Human Fibroblast Proliferation In Vitro. Clinics in orthopedic surgery 10, 240, 2018.
24. Ozer, K., Kankaya, Y., and Colak, O. An important and overlooked parameter in platelet rich plasma preparation: The mean platelet volume. Journal of cosmetic dermatology 2018.
25. Atashi, F. S.-B., V.; Nayernia, Z.; Pittet-Cuenod, B. and Modarressi, A. Platelet Rich Plasma Promotes Proliferation of Adipose Derived Mesenchymal Stem Cells via Activation of AKT and Smad2 Signaling Pathways Stem Cell Res Ther 52015.
26. Marx, R. E. Platelet-rich plasma (PRP): what is PRP and what is not PRP?Implant dentistry 10, 225, 2001.
27. Yoshida, R., Cheng, M., and Murray, M. M. Increasing platelet concentration in platelet-rich plasma inhibits anterior cruciate ligamentcell function in three-dimensional culture. Journal of orthopaedic research: official publication of the Orthopaedic Research Society 32, 291, 2014.
28. Graziani, F., Ivanovski, S., Cei, S., Ducci, F., Tonetti, M., and Gabriele, M. The in vitro effect of different PRP concentrations on osteoblasts and fibroblasts. Clinical oral implants research 17, 212, 2006.
29. Cheng, F., Shen, Y., Mohanasundaram, P., Lindstrom, M., Ivaska, J., Ny, T., and Eriksson, J. E. Vimentin coordinates fibroblast proliferation and keratinocyte differentiation in wound healing via TGF-beta-Slug signaling. Proceedings of the National Academy of Sciences of the United States of America 113, E4320, 2016.
30. Chellini, F., Tani, A., Vallone, L., Nosi, D., Pavan, P., Bambi, F., Zecchi Orlandini, S., and Sassoli, C. Platelet-Rich Plasma Prevents In Vitro Transforming Growth Factor-beta1-Induced Fibroblast to Myofibroblast Transition: Involvement of Vascular Endothelial Growth Factor (VEGF)-A/VEGF Receptor-1-Mediated Signaling (dagger). Cells 72018.
31. Omar, N. N., EI-Tawdi, A. H., Tash, R. F., Shoukry, Y., Mahmoud, N. A., and E I Bakly, W. Tumor potential in rat wounds after short- and long-term administration of platelet-rich plasma. Journal of biological regulators and homeostatic agents 31, 889, 2017.
32. Rajamani, K., Li, Y. S., Hsieh, D. K., Lin, S. Z., Harn, H. J., and Chiou, T. W. Genetic and epigenetic instability of stem cells. Cell transplantation 23, 417, 2014.

The invention claimed is:

1. A cross-linked hyaluronic acid hydrogel having a dynamic viscosity of about 1 Pa·s to about 5.2 Pa·s, or <=6 Pa·s., <=5.5 Pa·s., <=5.2 Pa·s., <=5 Pa·s., <=4.5 Pa·s., or <=4 Pa·s, measured at a shear rate of 1 $s^{-1}$, wherein the cross-linked hyaluronic acid hydrogel has a hyaluronic acid concentration between about 0.5% wt/vol to about 10% wt/vol and a degree of crosslinking between about 0.5% to about 10%.

2. The cross-linked hyaluronic acid hydrogel of claim 1, having an elasticity of <=100 Pa·s, <=70 Pa·s, <=60 Pa·s, <=50 Pa·s, <=40 Pa·s, <=30 Pa·s, <=20 Pa·s or <=10 Pa·s.

3. The cross-linked hyaluronic acid hydrogel of claim 1, having a molecular weight between 100 KDa and 6000 KDa, 500 KDa and 2000 KDa, or about 1300 KDa, about 1400 KDa, about 1500 KDa, about 1600 KDa or about 1700 KDa.

4. The cross-linked hyaluronic acid hydrogel of claim 1, having a concentration of cross-linked hyaluronic acid between about 0.5% wt/vol to about 10% wt/vol, between about 1% wt/vol to about 2.5% wt/vol, about 1.5% wt/vol or about 2% wt/vol.

5. The cross-linked hyaluronic acid hydrogel of claim 1, having a degree of crosslinking between about 0.5% to about 10%, between about 1% to about 5%, between about 2% to about 4%, about 2.5%, about 3% or about 3.5%.

6. The cross-linked hyaluronic acid hydrogel of claim 1, having a BDDE content <=2.5 ppm, <=2 ppm, <=1.5 ppm or <=1 ppm.

7. The cross-linked hyaluronic acid hydrogel of claim 1, having a density lower than 1.04 $g/cm^3$.

8. The cross-linked hyaluronic acid hydrogel of claim 1, having a dynamic viscosity <=5.2 Pa·s. and a molecular weight of about 1500 KDa.

9. The cross-linked hyaluronic acid hydrogel of claim 1, having a concentration of cross-linked hyaluronic acid of about 2% wt/vol.

10. The cross-linked hyaluronic acid hydrogel of claim 1, having a concentration of cross-linked hyaluronic acid of about 2% wt/vol, and with a degree of crosslinking of about 3%.

11. The cross-linked hyaluronic acid hydrogel of claim 1, having an elasticity <=60 Pa·s. for use in syringes.

12. The cross-linked hyaluronic acid hydrogel of claim 1 combined with a platelet concentrate and a bone marrow concentrate.

13. A container containing a cross-linked hyaluronic acid hydrogel having a dynamic viscosity of about 1 Pa·s to about 5.2 Pa·s, or <=6 Pa·s., <=5.5 Pa·s., <=5.2 Pa·s., <=5 Pa·s., <=4.5 Pa·s., or <=4 Pa·s, measured at a shear rate of 1 $s^{-1}$, wherein the cross-linked hyaluronic acid hydrogel has a hyaluronic acid concentration between about 0.5% wt/vol to about 10% wt/vol and a degree of crosslinking between about 0.5% to about 10%.

14. The container of claim 13, wherein said container is a tube or syringe.

15. The container of claim 13, further comprising at least one anticoagulant and/or at least one thixotropic gel.

16. The container of claim 13, further containing additives comprising an anticoagulant and a thixotropic gel, wherein the density of said thixotropic gel is selected from about 1.03 to about 1.05 $g/cm^3$ or from about 1.08 to about 1.09 $g/cm^3$.

17. The container of claim 16, wherein said anticoagulant is sodium citrate.

18. The container of claim 13, wherein said container contains only three additives consisting of hyaluronic acid, thixotropic gel, and anticoagulant, and wherein said hyaluronic acid is a first layer from a distal end of said container, followed by a second layer consisting of said thixotropic gel followed by a third layer consisting of said anticoagulant.

19. The container of claim 13, wherein said container is for the preparation of a Thrombin serum (TS), or a platelet concentrate (PC) or a bone marrow concentrate (BMC) or both PC and BMC or any of the preceding compositions in combination with a biomaterial or hyaluronic acid.

* * * * *